United States Patent [19]
Danishefsky et al.

[11] Patent Number: 5,416,225
[45] Date of Patent: May 16, 1995

[54] TOTAL SYNTHESIS OF TAXOL

[75] Inventors: Samuel J. Danishefsky, New Haven, Conn.; William G. Bornmann; Yves Queneau; Thomas V. Magee, all of New York, N.Y.; Walter J. Krol, Wallingford, Conn.

[73] Assignee: Sloan-Kettering Institute for Cancer Research, New York, N.Y.

[21] Appl. No.: 860,792

[22] Filed: Mar. 30, 1992

[51] Int. Cl.$^6$ .............................................. C07D 317/72
[52] U.S. Cl. ...................................... 549/341; 549/342
[58] Field of Search ............................... 549/341, 342

[56] References Cited

U.S. PATENT DOCUMENTS 4,876,399 10/1989 Holton et al. .................... 568/817

OTHER PUBLICATIONS

Andriamialisoa, R. Z, *Tetrahedron*, vol. 40 (21), pp. 4285–4295 (1984); U.K.
Berkowitz, W. F. and Amarasekra, A. S., *Tetrahedron Letters*, vol. 26 (31), pp. 3663–3664 (1985); U.K.
Bonnert, R. V. and Jenkins, P. R., *J. Chem. Soc. Perkin Trans.*, vol. 1, pp. 413–418 (1989); U.K.
Brown, P. A. and Jenkins, P. R., *J. Chem. Soc. Perkin Trans.*, vol. 1, pp. 1303–1309 (1986); U.K.
Blechert, S. and Guenard, D., *The Alkaoids*, vol. 39, pp. 195–238 (1990); U.S.A.
Danishefsky, S., et al., *J. Amer. Chem. Soc.*, vol. 101, pp. 6996–7000 (1979); U.S.A.
Denis, J., et al., *J. Am. Chem. Soc.*, vol. 110, pp. 5917–5919 (1988); U.S.A.
Ettouati, L., et al., *Tetrahedron*, vol. 47, pp. 9823–9838 (1991); U.K.
Holton, R. A., et al., *J. Am. Chem. Soc.*, vol. 110, pp. 6558–6560 (1988); U.S.A.
Kato, T., et al., *Tetrahedron Letters*, pp. 1201–1204 (1978); U.K.
Kende, A. S., et al., *J. Amer. Chem. Soc.*, vol. 108, pp. 3513–3515, (1986); U.S.A.
Kitagawa, I., et al., *Chemistry Letters*, pp. 1001–1004 (1980); Japan.
Lin, J., et al., *J. Org. Chem.*, vol. 52, pp. 3745–3752 (1987); U.S.A.

Ohtsuka, Y. and Oishi, T., *Chem. Pharm. Bull.*, vol. 39 (6) pp. 1359–1364 (1991); Japan.
Patterson, L., et al., *Tetrahedron Letters*, vol. 28, pp. 2753–2756 (1987); U.K.
Sakan, K. and Craven, B. M., *J. Am. Chem. Soc.*, vol. 105, pp. 3732–3734 (1983): U.S.A.
Shea, K. J. and Haffner, C. D., *Tetrahedron Lett.*, vol. 29 (12), pp. 1367–1370 (1988); U.K.
Shea, K. J., et al., *J. Am. Chem. Soc.*, vol. 108, pp. 4953–4956 (1986); U.S.A.
Swindell, C. S., et al., *J. Org. Chem.*, vol. 52, pp. 2346–2355 (1987); U.S.A.
Trost, B. M. and Hiemstra, H., *J. Am. Chem. Soc.*, vol. 104, pp. 886–887 (1982): U.S.A.
Wani, M. C., et al., *J. Am. Chem. Soc.*, vol. 93, pp. 2325–2327 (1971); U.S.A.
Wender, P. A. and Snapper, M. L. *Tetrahedron Lett.*, vol. 28 (20), pp. 2221–2224 (1987); U.K.
Winkler, J. D., et al., *J. Am. Chem. Soc.*, vol. 108, pp. 6425–6427 (1986); U.S.A.
Yadav, J. S. and Ravishankar, R., *Tetrahedron Letters*, vol. 32, (23), pp. 2629–2632 (1991); U.K.

*Primary Examiner*—C. Warren Ivy
*Assistant Examiner*—Ba K. Trinh
*Attorney, Agent, or Firm*—John P. White

[57] ABSTRACT

The present invention provides two basic routes for the total synthesis of taxol having the structure:

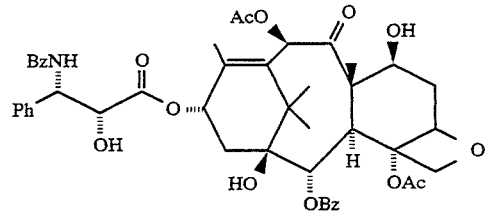

The present invention also provides the intermediates produced in the above processes, processes for synthesizing these intermediates as well as analogs to taxol. Both the intermediates and analogs to taxol may prove to be valuable anticancer agents.

3 Claims, 20 Drawing Sheets

TOTAL SYNTHESIS OF TAXOL

BACKGROUND OF THE INVENTION

Throughout this application, various publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The chemistry and pharmacology of the potent anticancer diterpenoid taxol 1 (1), isolated from the yew tree, *Taxus brevifolia*, has been reviewed extensively (2, 3, 4, 5). Taxol is currently undergoing phase II trials (6) and has shown very encouraging antitumor activity, especially against ovarian and breast cancers (4, 5).

Unfortunately, the natural availability of taxol is extremely limited. The increasing demand of taxol for the treatment of patients and the desirability of analogs to determine the real pathway of its mode of action has made the total synthesis or hemi-synthesis of taxol and its analogs a high priority over the last ten years (2, 3, 7).

Attempts at the hemi-synthesis of taxol have been based on using an extract from the leaves of the yew tree, 10-deacetylbaccatin III, as the starting material (3). Structural modifications of taxol have also been performed using taxol as the starting material itself, or 10-deacetylbaccatin III (3). In addition, there has been limited success in synthesizing the taxane skeleton or framework (2, 3, 7).

However, due to the complex structure of taxol, i.e. the vast functionalities and the buildup of the highly strained middle ring system, the various efforts at the total synthesis of this tetracyclic compound have not been successful (2, 3).

The inventors have overcome the difficulties faced by others and have been able to synthesize taxol via two routes. The present invention provides two basic routes for the total synthesis of taxol, important intermediates produced therein, processes for synthesizing these intermediates as well as analogs to taxol. Both the intermediates and analogs to taxol may prove to be valuable anticancer agents.

SUMMARY OF THE INVENTION

The present invention provides a compound having the structure:

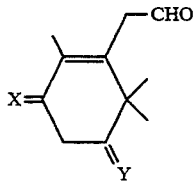

wherein X is H, OH, O, or OSiR$_3$; Y is —OCH$_2$C-H$_2$O—; R is an alkyl or aryl group.

The present invention also provides a compound having the structure:

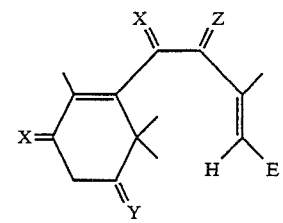

wherein each X is independently the same or different and is H, OH, O or OSiR$_3$; Y is —OCH$_2$CH$_2$O—; Z is OH, O or OTMS; E is H, CN, CO$_2$R, CHO or CH$_2$OR'; R' is H, COR, R or SiR$_3$; and R is an alkyl or aryl group.

The present invention further provides a compound having the structure:

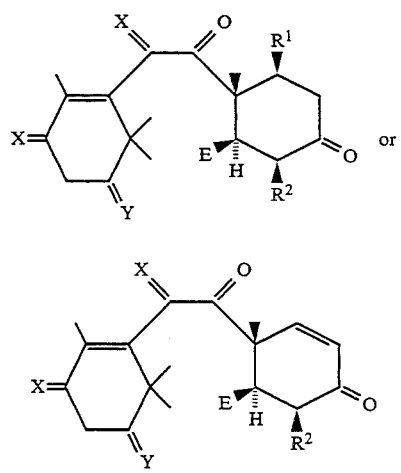

wherein each X is independently the same or different and is H, OH, O, or OSiR$_3$; Y is H, O, or —OCH$_2$C-H$_2$O—; E is H, CN, CO$_2$R, CHO, or CH$_2$OR'; R$^1$ is H, OH, OCOR, OR or OSiR$_3$; and R$^2$ is H, CH$_2$OSiR$_3$, CH$_2$SR, or CH$_2$SOR; wherein R' is H, COR, R, or SiR$_3$ and R is an alkyl or aryl group.

Additionally, the present invention provides a compound having the structure:

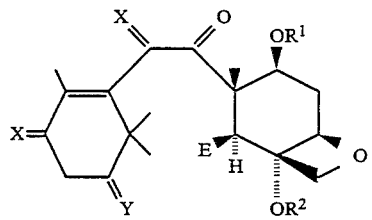

wherein each X is independently the same or different and is H, OH, O, OR or OSiR$_3$; Y is O or —OCH$_2$C-H$_2$O—; E is CN, CO$_2$R, CHO, or CH$_2$OR'; R$^1$ is H, COR, or SiR$_3$; and R$^2$ is H, COR, or SiR$_3$; wherein R' is H, COR, R, or SiR$_3$ and R is an alkyl or aryl group.

The present invention also provides a compound having the structure:

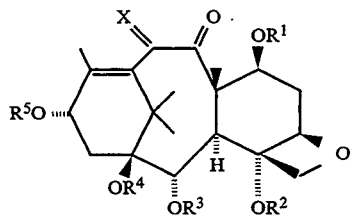

wherein X is H, OH, O, OR, or OSiR$_3$; and R$^1$, R$^2$, R$^3$, R$^4$, and R$^5$ are independently the same or different and are H, COR, SiR$_3$, or R; wherein R is an alkyl or aryl group; with the proviso that X, R$^1$, R$^2$, R$^3$, R$^4$, and R$^5$ are not OAc, H, Ac, COPh, H, and PhCH(BzNH)CH(OH)CO—, respectively.

The present invention also provides processes for synthesizing the compounds above.

In addition, the present invention also provides a process for synthesizing a compound having the structure:

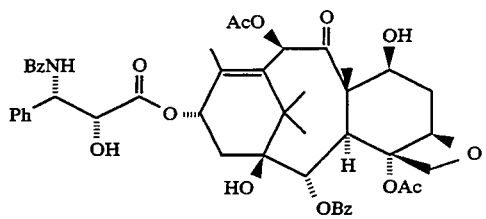

which comprises:

(a) treating a compound having the structure:

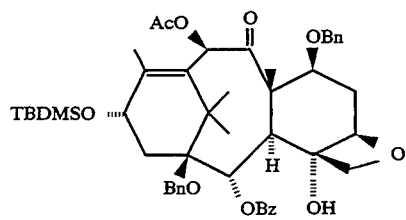

under suitable conditions to form a compound having the structure:

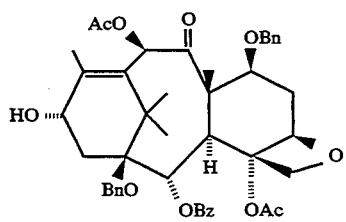

(b) treating the compound formed in step (a) under suitable conditions to form a compound having the structure:

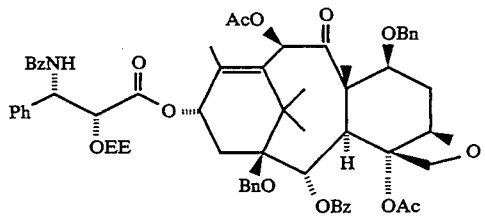

and (c) treating the compound formed in step (b) under suitable conditions to form the compound having the structure:

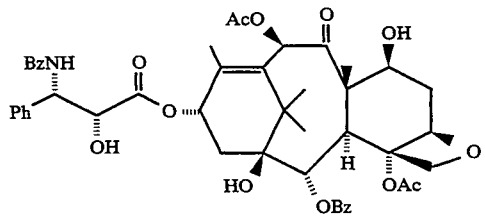

The present invention also provides a compound having the structure:

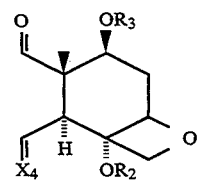

wherein X$_4$ is H, OR, O, —OCH$_2$CH$_2$O—, or —SCH$_2$CH$_2$CH$_2$S—; and R$_2$ and R$_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a compound having the structure:

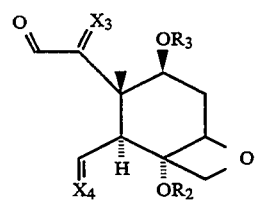

wherein X$_3$ and X$_4$ are independently the same or different and are H, OR, O, —OCH$_2$CH$_2$O—, or —SCH$_2$CH$_2$CH$_2$S—; and R$_2$ and R$_3$ are independently the same or different and are H, acyl, alkyl, aryl, TBS, TES, TMS, or TBDPS; wherein R is H, acyl, alkyl, aryl, TBS, TES, TMS, or TBDPS.

Moreover, the present invention provides a compound having the structure:

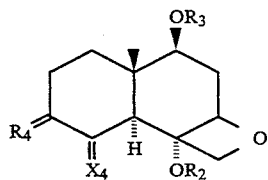

wherein $X_4$ is H, OR, O, —OCH$_2$CH$_2$O—, or —SCH$_2$CH$_2$CH$_2$S—; $R_2$ and $R_3$ are independently the same or different and are H, acyl, alkyl, aryl, TBS, TES, TMS, or TBDPS; and $R_4$ is PhCH(BzNH)CH(OH)-CO—, O, an alkyl, or aryl group; wherein R is H, acyl, alkyl, aryl, TBS, TES, TMS, or TBDPS.

The present invention also provides a compound having the structure:

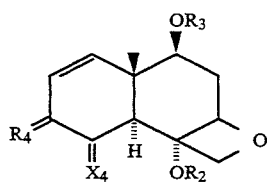

wherein $X_4$ is H, OR, O, —OCH$_2$CH$_2$O—, or —SCH$_2$CH$_2$CH$_2$S—; $R_2$ and $R_3$ are independently the same or different and are H, acyl, alkyl, aryl, TBS, TES, TMS, or TBDPS; and $R_4$ is PhCH(BzNH)CH(OH)-CO—, O, an alkyl, or aryl group; wherein R is H, acyl, alkyl, aryl, TBS, TES, TMS, or TBDPS.

The present invention further provides a compound having the structure:

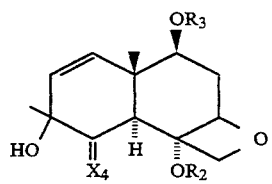

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS.

In addition, the present invention provides a compound having the structure:

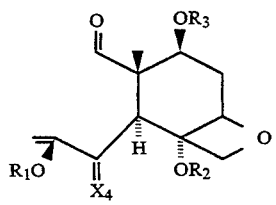

wherein $X_4$ is H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a compound having the structure:

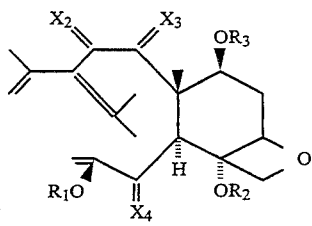

wherein $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a compound having the structure:

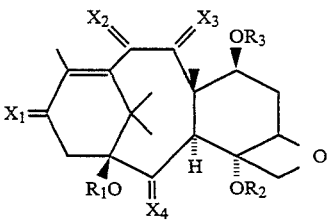

wherein $X_1$, $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a compound having the structure:

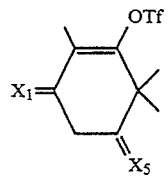

wherein $X_1$ and $X_5$ are independently the same or different and are H, OR, O, —OCH$_2$CH$_2$O—, or —SCH$_2$CH$_2$CH$_2$S—; wherein R is H, acyl, alkyl, aryl, TBS, TES, TMS, or TBDPS.

The present invention further provides a compound having the structure:

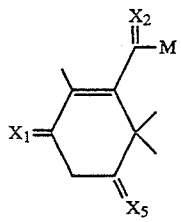

wherein $X_1$, $X_2$, and $X_5$ are independently the same or different and are H, OR, O, —OCH$_2$CH$_2$O—, or —SCH$_2$CH$_2$CH$_2$S—; and M is H or a metal; wherein R is H, acyl, alkyl, aryl, TBS, TES, TMS, or TBDPS.

Additionally, the present invention provides a compound having the structure:

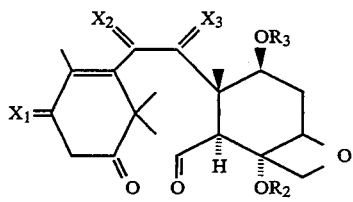

wherein $X_1$, $X_2$, and $X_3$, are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention further provides processes for synthesizing the compounds above.

Finally, the present invention provides a process for synthesizing a compound having the structure:

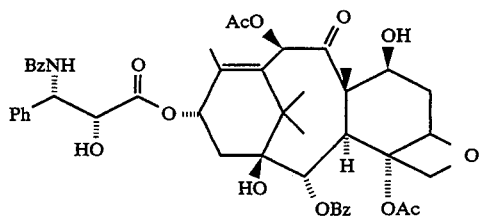

which comprises:

(a) synthesizing a compound having the structure:

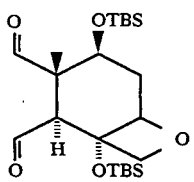

(b) treating the compound formed in step (a) under suitable conditions to form a compound having the structure:

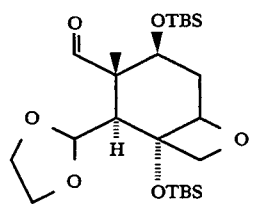

(c) contacting the compound formed in step (b) with lithiodithiane under suitable conditions to form a compound having the structure:

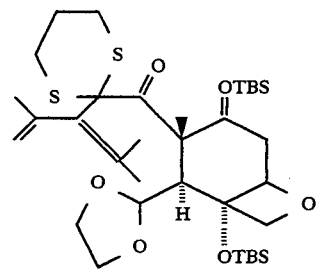

(d) deketalizing the compound formed in step (c) under suitable conditions to form a compound having the structure:

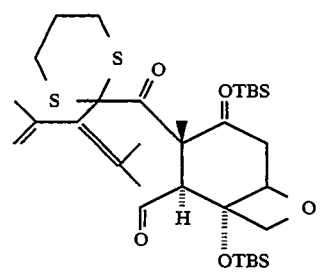

(e) contacting the compound formed in step (d) with methoxyvinyllithium under suitable conditions to form a compound having the structure:

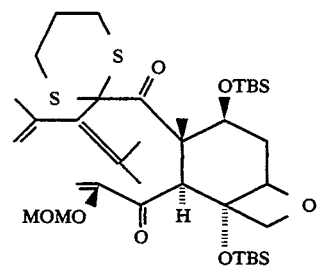

(f) heating the compound formed in step (e) under suitable conditions to form a compound having the structure:

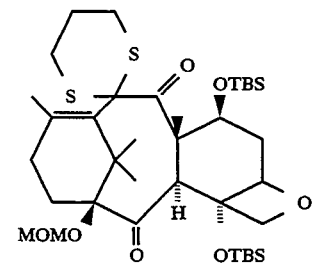

(g) reducing and esterifying the compound formed in step (f) under suitable conditions to form a compound having the structure:

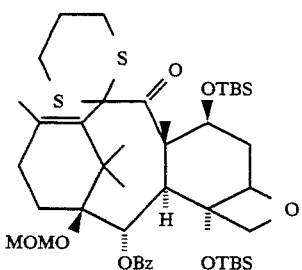

(h) oxidizing the compound formed in step (g) under suitable conditions to form a compound having the structure:

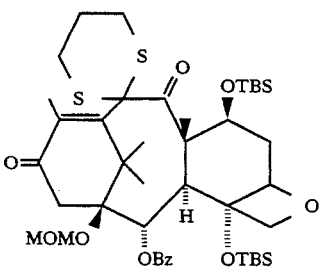

(i) removing the thioketal of the compound formed in step (h) under suitable conditions to form a compound having the structure:

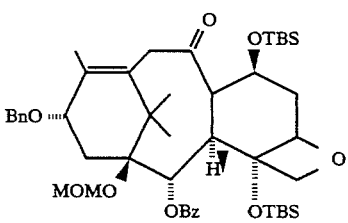

(j) treating the compound formed in step (i) under suitable conditions to form a compound having the structure:

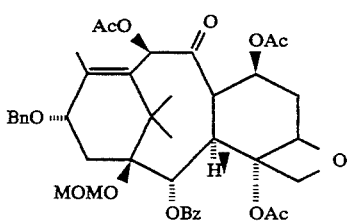

(k) treating the compound formed in step (j) under suitable conditions to form a compound having the structure:

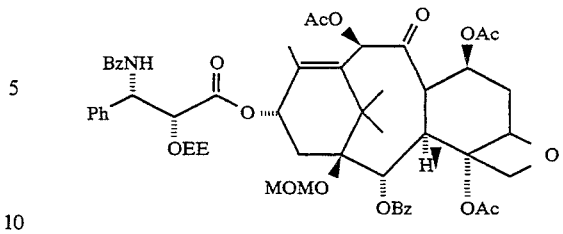

and (l) treating the compound formed in step (k) under suitable conditions to form the compound having the structure:

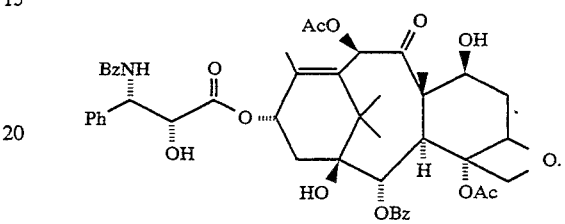

DETAILED DESCRIPTION OF THE INVENTION

Figure 1:
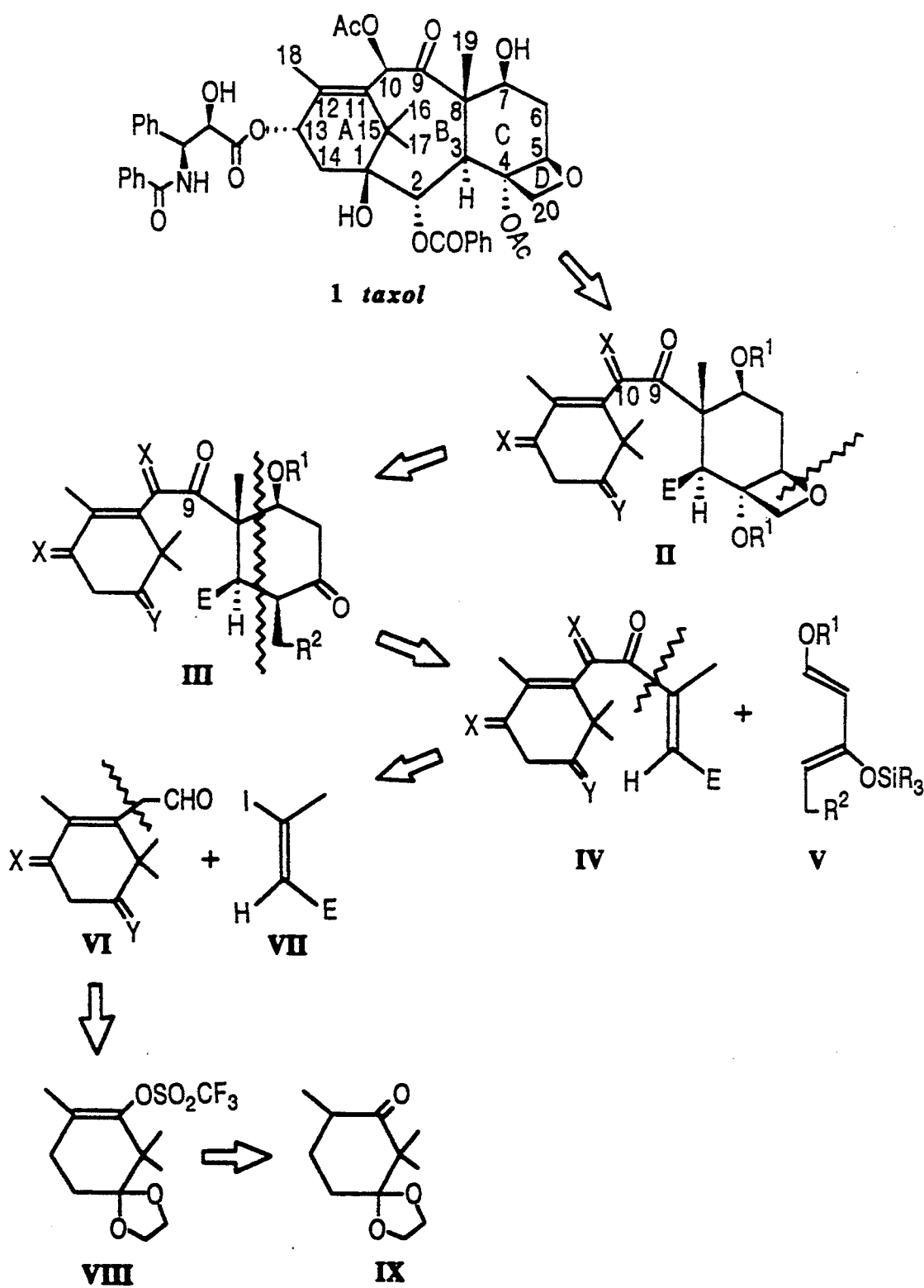
FIG. 1. Retrosynthetic analysis of Route 1 total synthesis of taxol. The functional groups are defined as follows: $R^1$=H, COR, SIR$_3$, or R; $R^2$=OSiR$_3$, SR, or SOR; E=CN, CO$_2$R, CHO, or CH$_2$R'; X=H,H, H,OH, H,OSiR$_3$, or O; Y=O or —OCH$_2$CH$_2$O—; R'=H, COR, SIR$_3$, or R; and R=alkyl, aryl.
Figure 2:
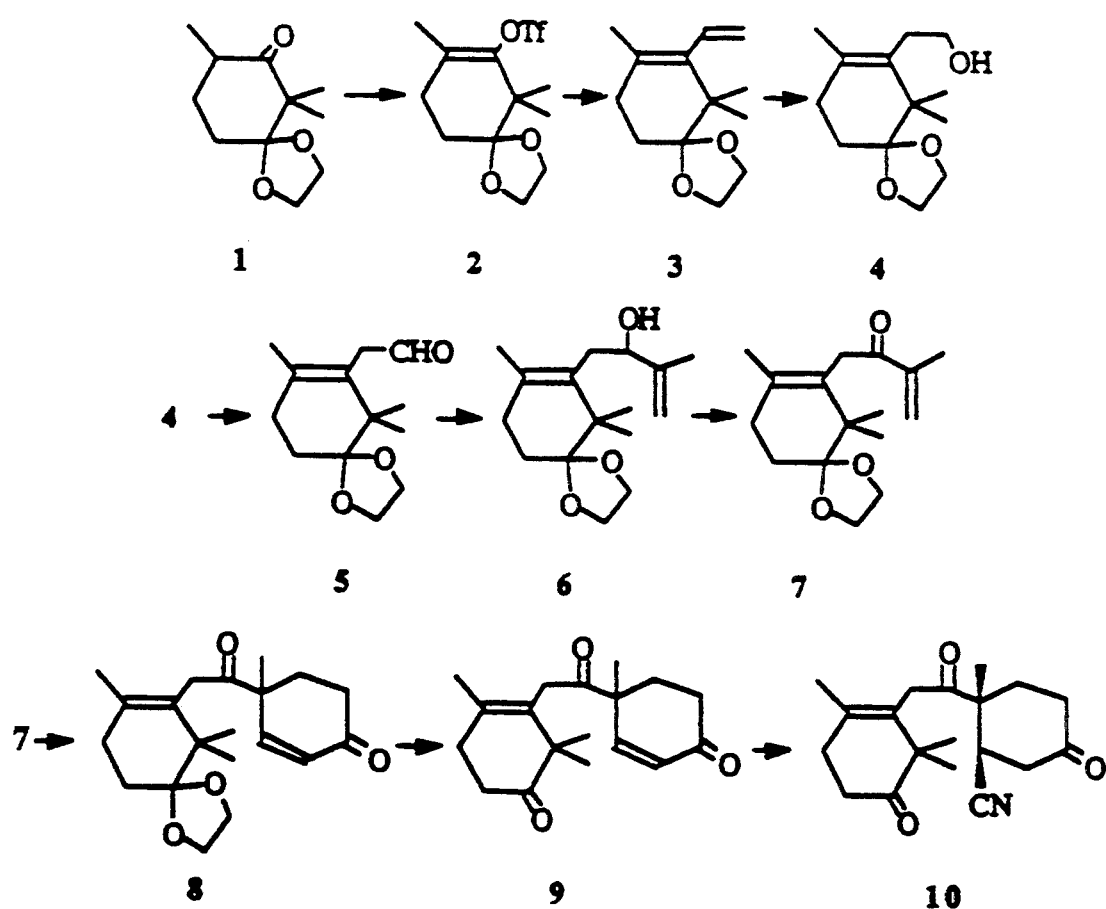
FIG. 2. A-ring synthesis and extension to aldehyde 5; preparation of the dienophile 7; Diels-Alder reaction with model four-carbon diene 1-methoxy-3-trimethylsilyloxy-1,3-butadiene (Danishefsky's diene), and Michael addition of a cyano fragment onto the enone function of the adduct.
Figure 3:
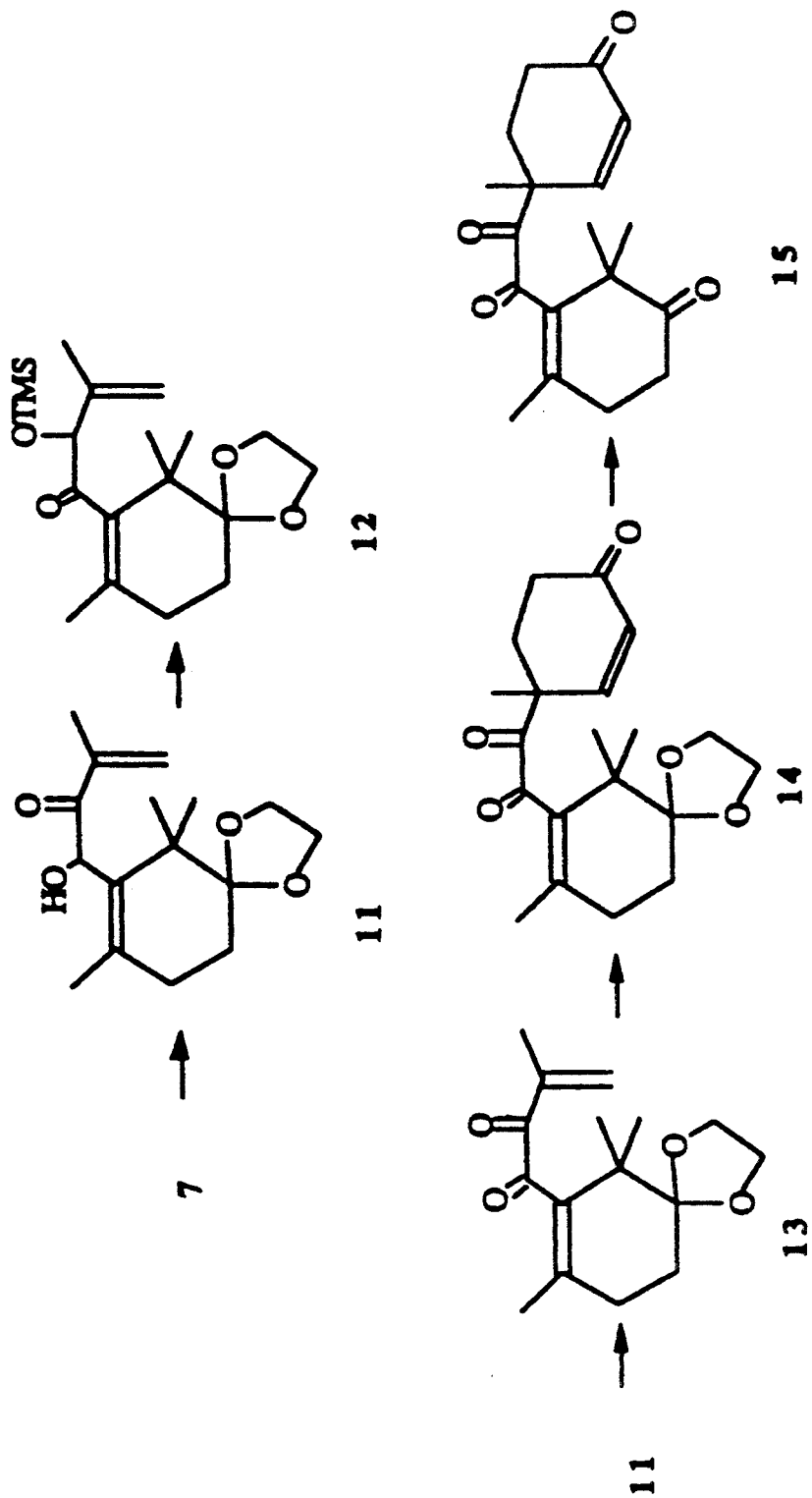
FIG. 3. Oxidation of dienophile 7 leading to dione 13 and Diels-Alder reaction with model four-carbon diene.
Figure 4:
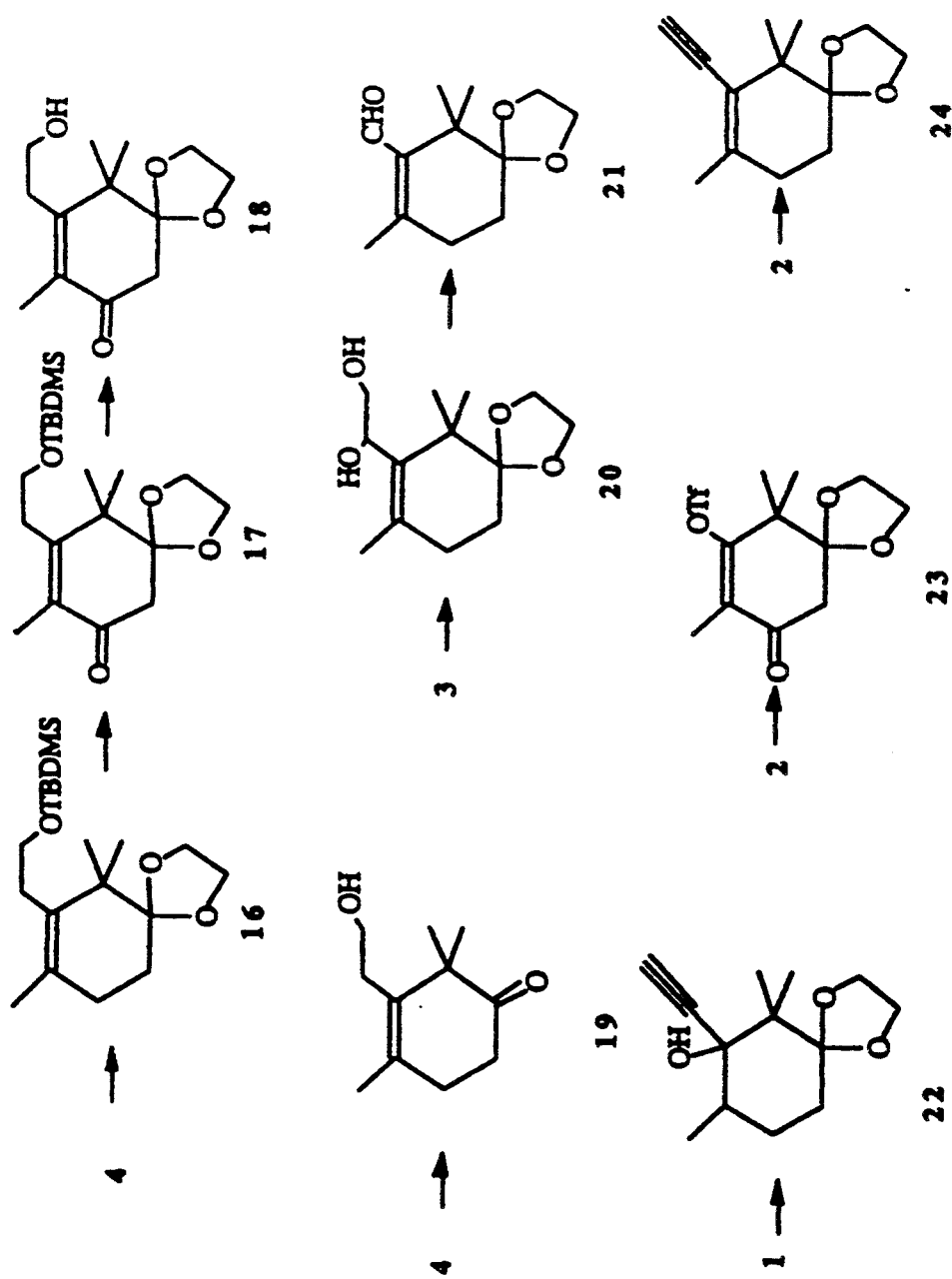
FIG. 4. Allylic oxidation of A-ring (preparation of compounds 17 and 23); deketalization of A-ring (preparation of compound 19); preparation of aldehyde 21 and acetylenic compounds 22 and 24.
Figure 5:
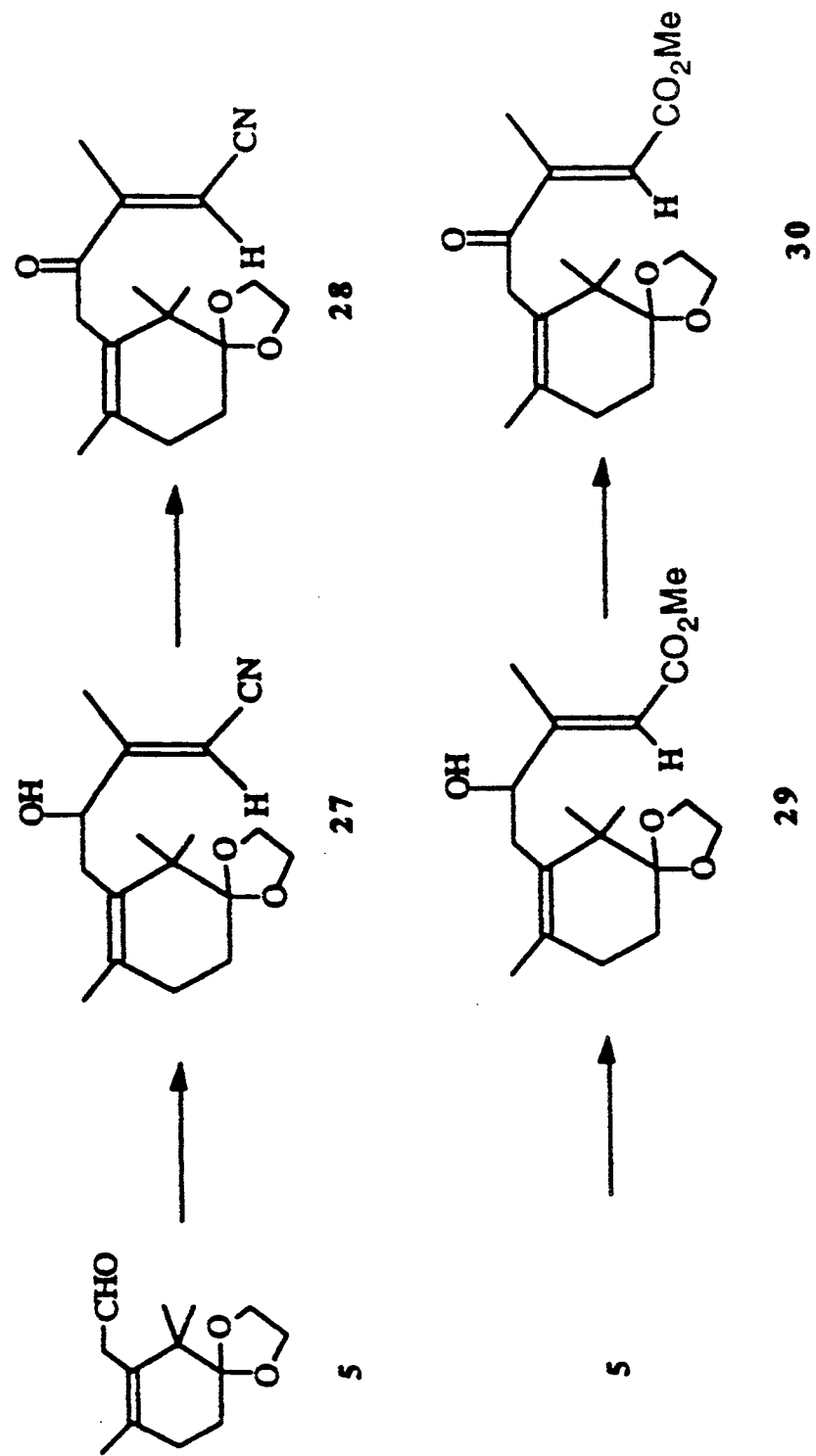
FIG. 5. Extension of aldehyde 5 to the trisubstituted dienophiles 28 and 30.

The present invention provides a compound having the structure:

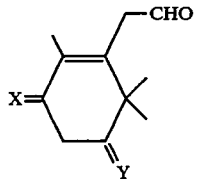

wherein X is H, OH, O, or OSiR₃; Y is —OCH₂CH₂O—; R is an alkyl or aryl group.

The present invention also provides a compound having the structure:

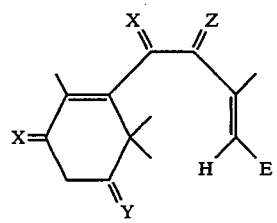

wherein each x is independently the same or different and is H, OH, O or OSiR₃; Y is —OCH₂CH₂O—; Z is OH, O or OTMS; E is H, CN, CO₂R, CHO or CH₂OR'; R' is H, COR, R or SiR₃; R is an alkyl or aryl group.

The present invention further provides a compound having the structure:

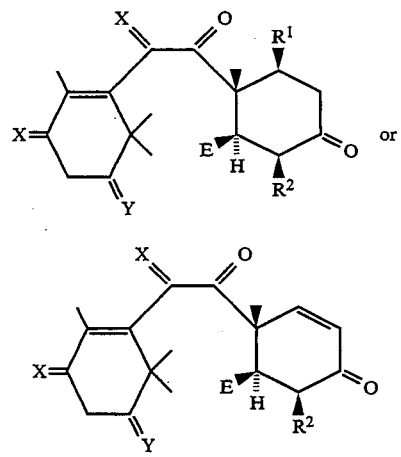

wherein each X is independently the same or different and is H, OH, O, or OSiR₃; Y is H, O, or —OCH₂CH₂O—; E is H, CN, CO₂R, CHO, or CH₂OR'; R¹ is H, OH, OCOR, OR or OSiR₃; and R² is H, CH₂OSiR₃, CH₂SR, or CH₂SOR; wherein R' is H, COR, R, or SiR₃ and R is an alkyl or aryl group.

As used herein, a bond denoted by a solid line juxtaposed to a dashed line represents (a) a double bond if terminated only by O; (b) a single bond if terminated by H, OH or OSiR₃; and (c) two single bonds if terminated by —OH₂CH₂O—.

Additionally, the present invention provides a compound having the structure:

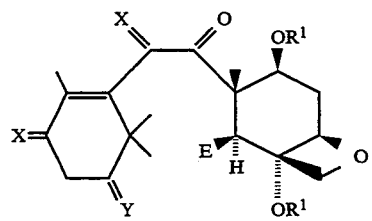

wherein each X is independently the same or different and is H, OH, O, OR or OSiR₃; Y is O or —OCH₂CH₂O—; E is CN, CO₂R, CHO, or CH₂OR'; R¹ is H, COR, or SiR₃; and R₂ is H, COR, or SiR₃; wherein R' is H, COR, R, or SiR₃ and R is an alkyl or aryl group.

The present invention also provides a compound having the structure:

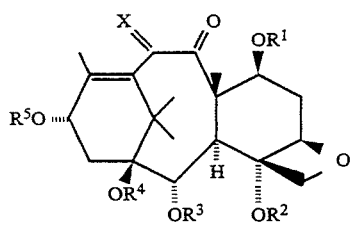

wherein X is H, OH, O, OR, or OSiR$_3$; and R$^1$, R$^2$, R$^3$, R$^4$, and R$^5$ are independently the same or different and are H, COR, SiR$_3$, or R; wherein R is an alkyl or aryl group; with the proviso that X, R$^1$, R$^2$, R$^3$, R$^4$, and R$^5$ are not OAc, H, Ac, COPh, H, and PhCH(BzNH)CH(OH)CO—, respectively.

The present invention also provides a process for synthesizing an aldehyde having the structure:

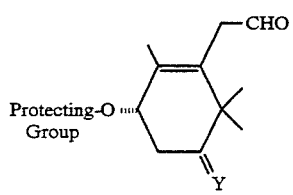

wherein Y is O or —OCH$_2$CH$_2$O—; which comprises:
(a) triflating a ketoketal having the structure:

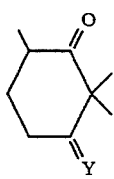

wherein Y is O or —OCH$_2$CH$_2$O—; under suitable conditions to form an enol triflate having the structure:

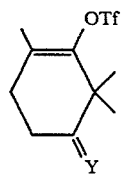

(b) reacting the enol triflate formed in step (a) with vinyltributylstannane under palladium (O) catalysis, under suitable conditions to form a diene having the structure:

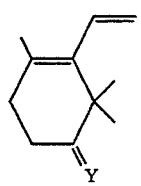

(c) reacting the diene formed in step (b) by hydroboration/oxidation under suitable conditions to form an alcohol having the structure:

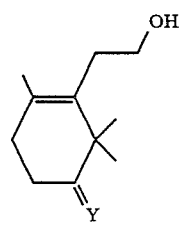

(d) contacting the alcohol formed in step (c) with a first protecting group under suitable conditions to form a protected alcohol having the structure:

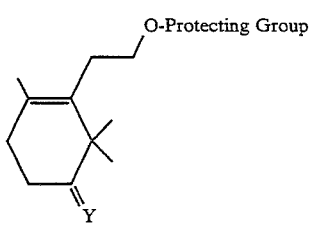

(e) oxidizing the protected alcohol formed in step (d) under suitable conditions to form an enone having the structure:

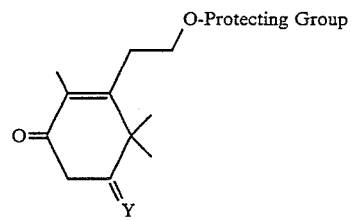

(f) reducing the enone formed in step (e) under suitable conditions to form an allylic alcohol having the structure:

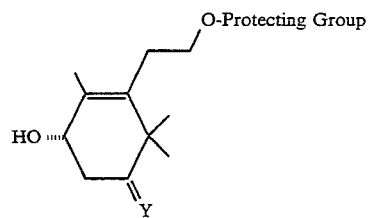

(g) contacting the allylic alcohol formed in step (f) with a second protecting group under suitable conditions to form a protected alcohol having the structure:

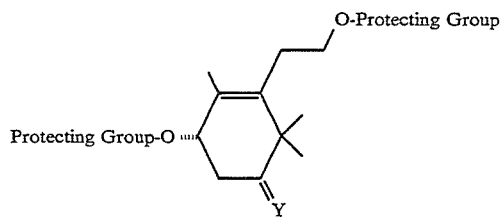

(h) treating the protected alcohol formed in step (g) under suitable conditions to selectively remove the first protecting group to form an alcohol having the structure:

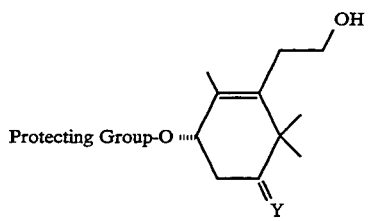

and (i) oxidizing the alcohol formed in step (h) to form the aldehyde having the structure:

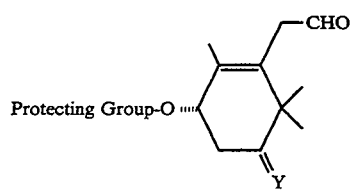

In the above process and the various processes which follow, the suitable conditions necessary for the various reactions and treatments may be found in the Experimental Details Section which follows. However, it is within the confines of the present invention that the specific reactants and solvents provided as well as the specific conditions necessary for reaction or treatment may be substituted with other suitable reactants, solvents and conditions well known to those skilled in the art.

In step (a) above, the "triflating" of the ketoketal is performed by reacting the ketoketal with a suitable triflating agent, preferably, N-phenyl-trifluoromethane sulfonimide. In step (b) above, the enol triflate formed in step (a) is coupled under palladium (O) catalysis with vinyl-tri-n-butylstannane leading to the diene. In step (c), the diene is preferably hydroborated with 9-BBN, to give, after basic hydroperoxide work-up, the alcohol. In step (d), the alcohol is treated with a protecting group, preferably TBDMSCl, or another suitable protecting group to form the protected alcohol. In step (e), the oxidizing of the protected alcohol is preferably performed via 3,5-dimethylpyrazole mediated allylic oxidation in the presence of a chromium trioxide complex. In step (f), the enone is preferably reduced with borane in the presence of a catalytic amount of chiral oxazoborolidine to give the allylic alcohol. In step (g), the alcohol function of the allylic alcohol is preferably protected with a TBDMS group. In step (h), the first protecting group is preferably removed by selective desilylation of the primary hydroxyl. In step (i), the alcohol is preferably oxidized by the method of Swern to form the aldehyde.

The present invention also provides a process for synthesizing a diketo dienophile having the structure:

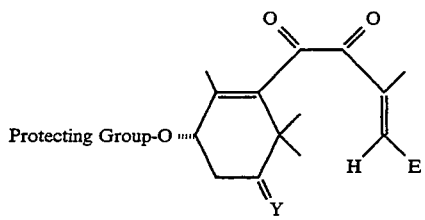

wherein Y is O or —OCH$_2$CH$_2$O—; and E is —CH$_2$OR′, CN, CO$_2$R, or CHO; wherein R′ is H, COR, R, or SiR$_3$ and R is an alkyl or aryl group; which comprises:

(a) synthesizing an aldehyde having the structure:

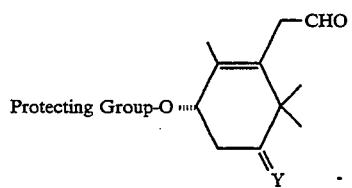

according to the process above;

(b) coupling the aldehyde formed in step (a) with a compound having the structure:

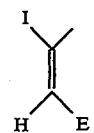

wherein E is —CH$_2$OR′, CN, CO$_2$R, or CHO; wherein R′ is H, COR, R, or SiR$_3$ and R is an alkyl or aryl group; under suitable conditions to form an allylic alcohol having the structure:

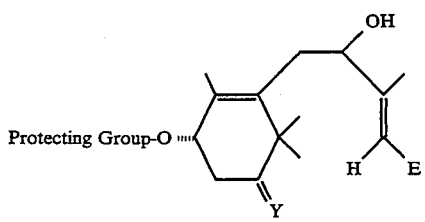

(c) oxidizing the allylic alcohol formed in step (b) under suitable conditions to form an enone having the structure:

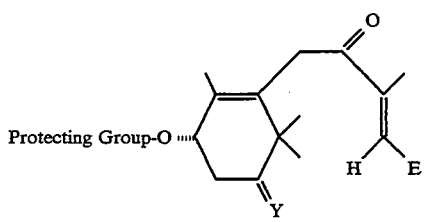

(d) treating the enone formed in step (c) under suitable conditions to form a hydroxyketone having the structure:

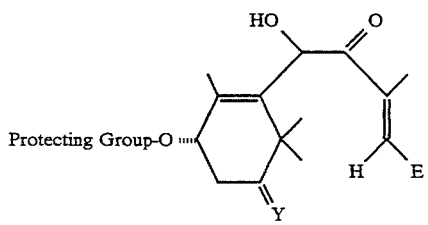

and (e) oxidizing the hydroxyketone formed in step (d) under suitable conditions to form the diketo dienophile having the structure:

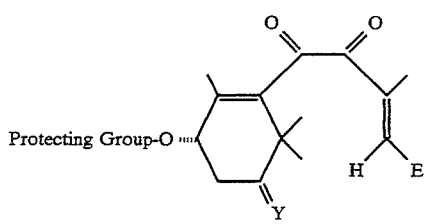

In step (a) above, the aldehyde may be synthesized by the previous process or other processes determinable by those skilled in the art. In step (b), the coupling is preferably performed by a nickel chloride catalyzed chromium (II) chloride promoted coupling of the iodide compound, preferably vinyl iodide, with the aldehyde to afford the allylic alcohol. In step (c), the alcohol is preferably oxidized by Swern oxidation (oxalyl chloride, dimethylsulfoxide, triethylamine, dichloromethane) to form the enone, which is converted in step (d) into the hydroxyketone by preferably adding KHMDS followed by N-phenylsulfonyl-phenyloxaziridine. In step (e), the hydroxyketone is preferably oxidized using oxalyl chloride and DMSO followed by triethylamine to form the diketo dienophile.

The present invention also provides a process for synthesizing a compound having the structure:

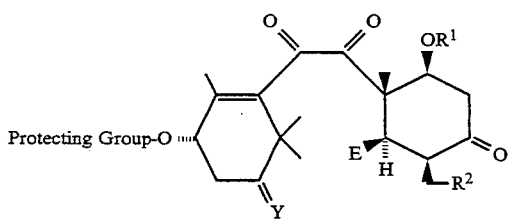

wherein Y is O or —OCH$_2$CH$_2$O—; E is —CH$_2$OR', CN, CO$_2$R, or CHO; R$^1$ is H, COR, R, or SiR$_3$; and R$^2$ is OSiR$_3$, SR, or SOR; wherein R' is H, COR, R, or SiR$_3$ and R is an alkyl or aryl group; which comprises:
  (a) synthesizing a diketo dienophile having the structure:

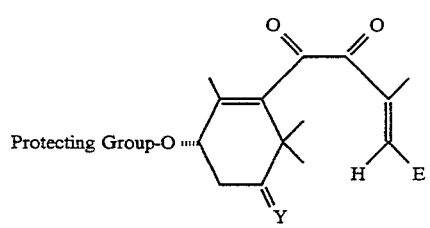

according to the process above;
and (b) coupling the diketo dienophile formed in step (a) with a diene having the structure:

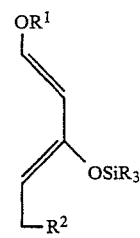

wherein R$^1$ is H, COR, R, or SiR$_3$; and R$^2$ is OSiR$_3$, SR, or SOR; wherein R is an alkyl or aryl group; to form the compound having the structure:

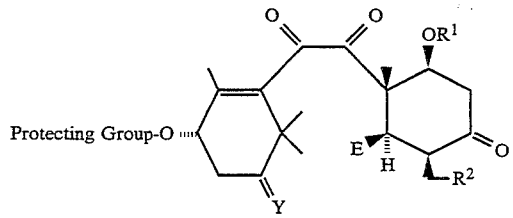

In step (a) above, the diketo dienophile may be synthesized by the previous process or other processes determinable by those skilled in the art. In step (b), Diels-Alder cycloaddition of the diketo dienophile with the diene followed by acidic work-up yields an adduct in which the primary silyl ether is selectively cleaved affording the alcohol. Alternatively, fluoride mediated work-up of the Diels-Alder reaction between the diketo dienophile and the diene produces the compound directly.

The present invention also provides a process for synthesizing a compound having the structure:

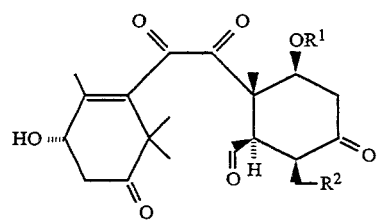

wherein R$^1$ is H, COR, R, or SiR$_3$; and R$^2$ is OSiR$_3$, SR, or SOR; wherein R is an alkyl or aryl group; which comprises:
  (a) synthesizing a compound having the structure:

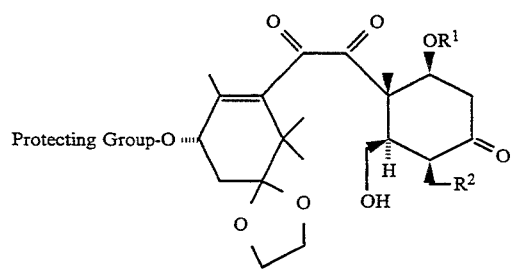

according to the process above;

(b) oxidizing the compound formed in step (a) under suitable conditions to form an aldehyde having the structure:

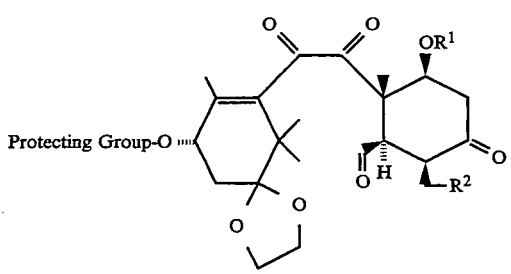

and (c) deketalizing the aldehyde formed in step (b) under suitable conditions to form the compound having the structure:

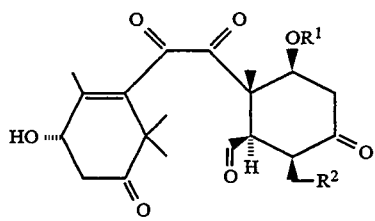

In step (a) above, the compound may be synthesized by the previous process or other processes determinable by those skilled in the art. In step (b), the compound of step (a) is preferably oxidized using oxalyl chloride and DMSO followed by triethylamine to form the aldehyde. In step (c), the deketalizaton preferably involves treating the ketal with p-toluenesulfonic acid in aqueous tetrahydrofuran to form the compound in which the protecting group, preferably the TBDMS ether, is concomitantly removed.

The present invention also provides a process for synthesizing a compound having the structure:

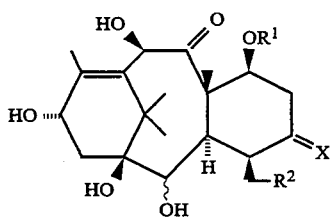

wherein X is OH or O; $R^1$ is H, COR, R, or $SiR_3$; and $R^2$ is $OSiR_3$, SR, or SOR; wherein R is an alkyl or aryl group; which comprises:

(a) synthesizing a compound having the structure:

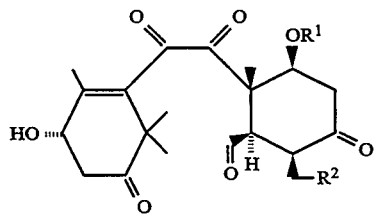

according to the process above;
and (b) coupling the compound formed in step (a) by intramolecular pinacolic coupling under suitable conditions to form a compound having the structure:

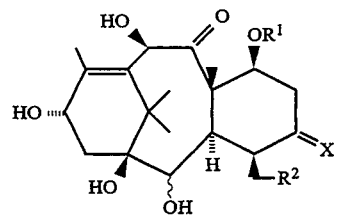

In step (a) above, the compound may be synthesized by the previous process or other processes determinable by those skilled in the art. In step (b), the pinacolic coupling preferably involves the samarium diiodide promoted intramolecular coupling which is assisted by both the presence of the free hydroxyl group at C-13 (numbering refers to the taxol skeleton), and the cyclic enediolate samarium species, formed by the complexation of the diketo system at C-9,10 with excess reagent. Concomitantly, the ketone at C-5 might be reduced.

The present invention also provides a process for synthesizing a compound having the structure:

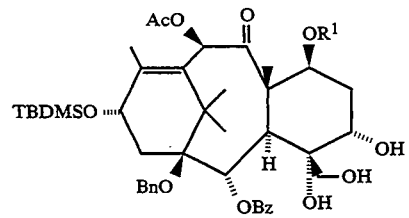

wherein $R^1$ is H, COR, R, or $SiR_3$; wherein R is an alkyl or aryl group; which comprises:

(a) synthesizing a compound having the structure:

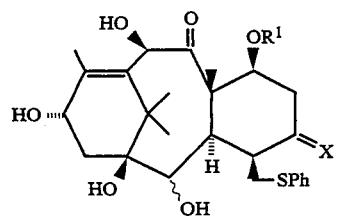

according to the process above;
(b) treating the compound formed in step (a) under suitable conditions to form a compound having the structure:

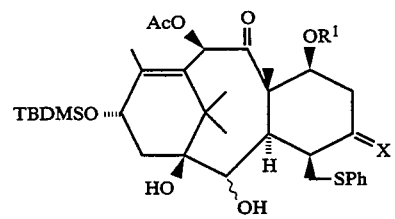

(c) oxidizing the compound formed in step (b) under suitable conditions to form a compound having the structure:

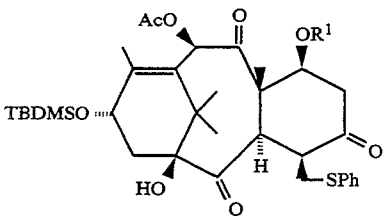

(d) reducing the compound formed in step (c) under suitable conditions to form a compound having the structure:

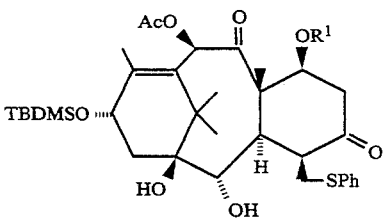

(e) treating the compound formed in step (d) under suitable conditions to form a compound having the structure:

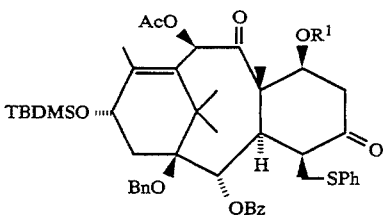

and (f) treating the compound formed in step (e) under suitable conditions to form the compound having the structure:

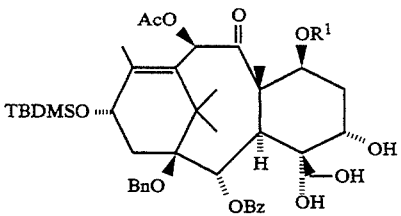

In step (a) above, the compound may be synthesized by the previous process or other processes determinable by those skilled in the art. In step (b), sequential selective protection of the hydroxyl groups, preferably by the addition of $Ac_2O/Py$, $TMSCl/NEt_3$, $TBDMSCl/NEt_3$, and $H^+$, of the compound synthesized in step (a) at C-10, C-1 (temporary) and C-13, leads to the formed compound. In step (c), the compound is preferably oxidized using oxalyl chloride and DMSO followed by triethylamine. In step (d), α-hydroxy at C-2 is preferably stereoselectively reduced using $Zn(BH_4)_2$. In step (e), the compound is sequentially protected, preferably by the addition of $TMSCl/NEt_3$, BzCl/Py, $H^+$, and NaH/BnBr. In step (f), the treating preferably comprises the reduction at C-5, the oxidation of the sulfide at C-20 to the sulfoxide and its elimination upon heating, followed by the osmium tetroxide catalyzed bis-hydroxylation of the allylic alcohol.

The present invention also provides a process for synthesizing a compound having the structure:

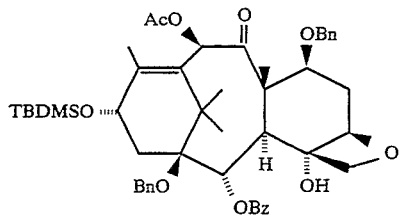

which comprises:

(a) synthesizing a compound having the structure:

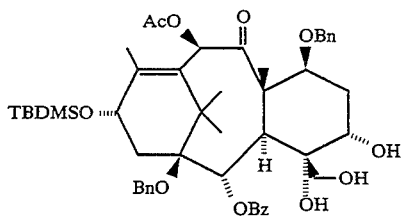

according to the process above;

and (b) treating the compound formed in step (a) under suitable conditions to form the compound having the structure:

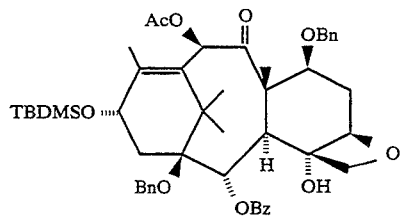

In step (a) above, the compound may be synthesized by the previous process or other processes determinable by those skilled in the art. In step (b), the compound of step (a) is converted to the hydroxy oxetane by known procedures (11,12).

The present invention also provides a process for synthesizing a compound having the structure:

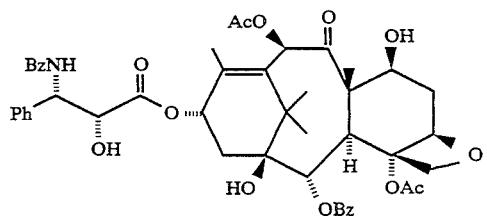

which comprises:

(a) synthesizing a compound having the structure:

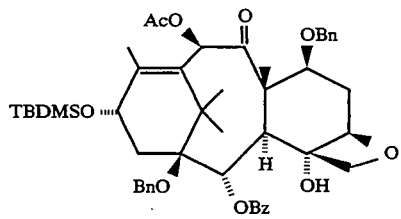

according to the process of above;

(b) treating the compound formed in step (a) under suitable conditions to form a compound having the structure:

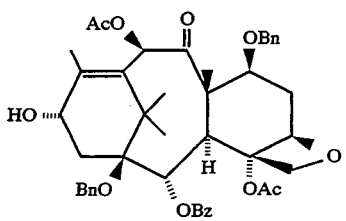

(c) treating the compound formed in step (a) under suitable conditions to form a compound having the structure:

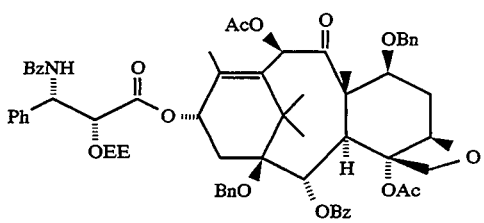

and (d) treating the compound formed in step (c) under suitable conditions to form a compound having the structure:

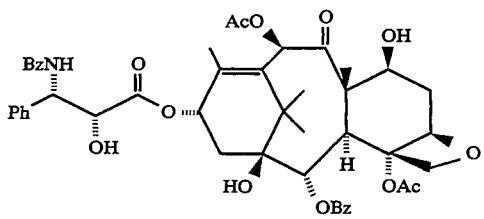

In step (a) above, the compound may be synthesized by the previous process or other processes known to those skilled in the art. In step (b), the hydroxy group at C-4 and the protecting group, TBDMSO, at C-13 are readily converted into corresponding acetoxy and hydroxy groups by the addition of Ac₂O/Py. and TBAF. In step (c), the side chain attachment at C-13 is accomplished by known protocols (49). In step (d), the sequential selective deprotection of hydroxyl groups at C-1 and C-7 by adding H₂/Pd/C produces taxol.

In addition, the present invention also provides a process for synthesizing a compound having the structure:

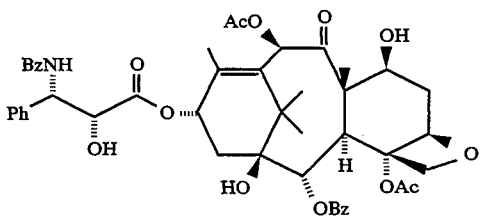

which comprises:

(a) treating a compound having the structure:

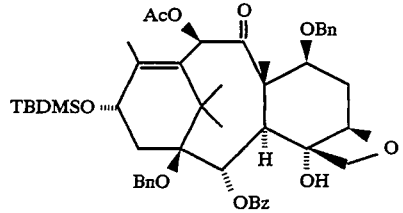

under suitable conditions to form a compound having the structure:

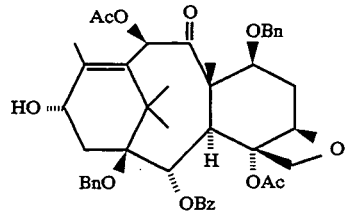

(b) treating the compound formed in step (a) under suitable conditions to form a compound having the structure:

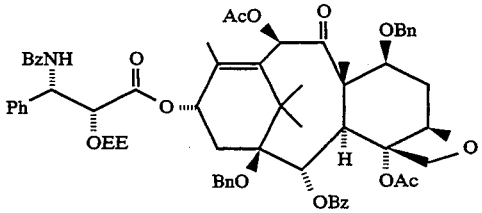

and (c) treating the compound formed in step (b) under suitable conditions to form the compound having the structure:

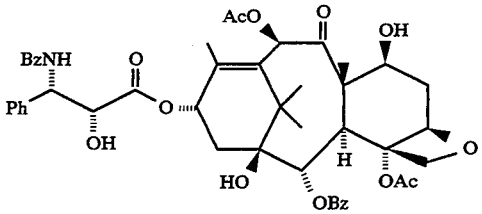

In step (a), the hydroxy group at C-4 and the protecting group, TBDMSO, at C-13 are readily converted into corresponding acetoxy and hydroxy groups by the addition of Ac₂O/Py. and TBAF. In step (b), the side chain attachment at C-13 is accomplished by known protocols (49). In step (c), the sequential selective deprotection of hydroxyl groups at C-1 and C-7 by adding H₂/Pd/C produces taxol.

The present invention also provides a process for synthesizing a compound having the structure:

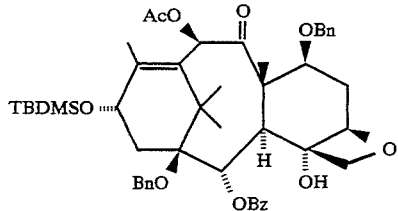

which comprises treating a compound having the structure:

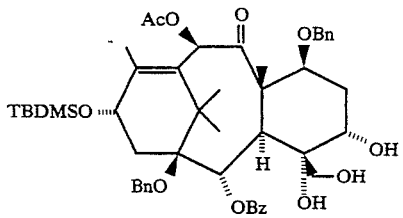

under suitable conditions to form the compound having the structure:

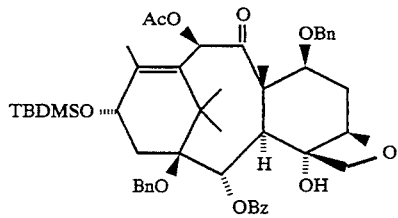

In process above, the starting compound is converted to the hydroxy oxetane by known procedures (11,12).

The present invention also provides a process for synthesizing a compound having the structure:

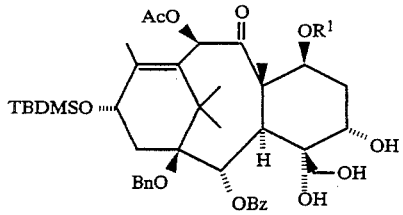

wherein $R^1$ is H, COR, R, or SiR₃; wherein R is an alkyl or aryl group; which comprises:

(a) treating a compound having the structure:

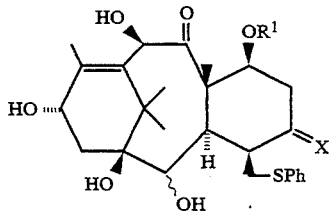

wherein X is O or OH; and $R^1$ is H, COR, R, or SiR₃; wherein R is an alkyl or aryl group; under suitable conditions to form a compound having the structure:

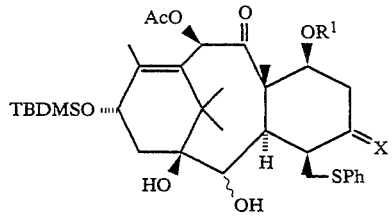

(b) oxidizing the compound formed in step (a) under suitable conditions to form a compound having the structure:

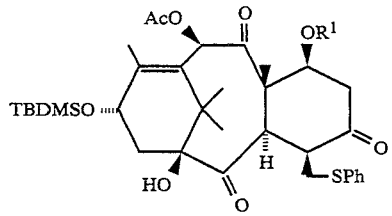

(c) reducing the compound formed in step (b) under suitable conditions to form a compound having the structure:

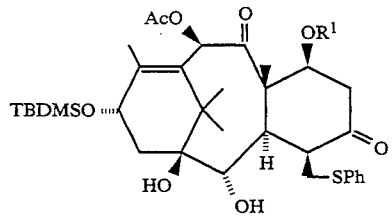

(d) treating the compound formed in step (c) under suitable conditions to form a compound having the structure:

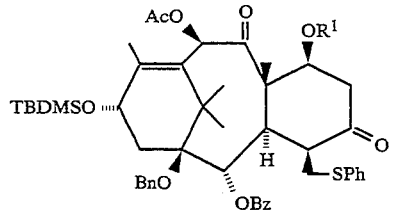

and (e) treating the compound formed in step (d) under suitable conditions to form the compound having the structure:

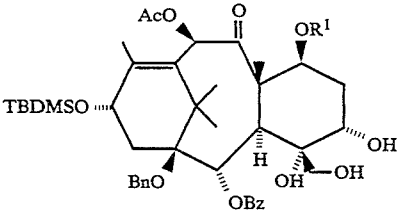

In step (a), sequential selective protection of the hydroxyl groups, preferably by the addition of Ac₂O/Py, TMSCl/NEt₃, TBDMSCl/NEt₃, and H+, of the starting compound at C-10, C-1 (temporary) and C-13, leads to the formed compound. In step (b), the compound is preferably oxidized using oxalyl chloride and DMSO followed by triethylamine. In step (c), α-hydroxy at C-2 is preferably stereoselectively reduced using Zn(BH₄)₂. In step (d), the compound is sequentially protected, preferably by the addition of TMSCl/NEt₃, BzCl/Py, H+, and NaH/BnBr. In step (e), the treating preferably comprises the reduction at C-5, the oxidation of the sulfide at C-20 to the sulfoxide, and its elimination upon heating, followed by the osmium tetroxide catalyzed bis-hydroxylation of the allylic alcohol.

The present invention also provides a process for synthesizing a compound having the structure:

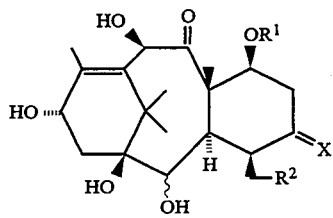

wherein R¹ is H, COR, R, or SiR₃; R² is OSiR₃, SR, or SOR; and X is OH or O; wherein R is an alkyl or aryl group; which comprises coupling a compound having the structure:

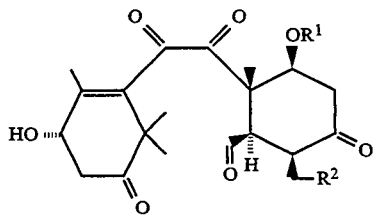

wherein R¹ is H, COR, R, or SiR₃; and R² is OSiR₃, SR, or SOR; wherein R is an alkyl or aryl group; by intramolecular pinacolic coupling under suitable conditions to form a compound having the structure:

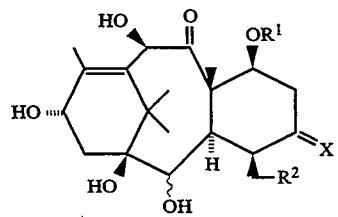

In process above, the pinacolic coupling preferably involves the samarium diiodide promoted intramolecular coupling which is assisted by both the presence of the free hydroxyl group at C-13 (numbering refers to the taxol skeleton), and the cyclic enediolate samarium species, formed by the complexation of the diketo system at C-9,10 with excess reagent. Concomitantly, the ketone at C-5 might be reduced.

The present invention also provides a process for synthesizing a compound having the structure:

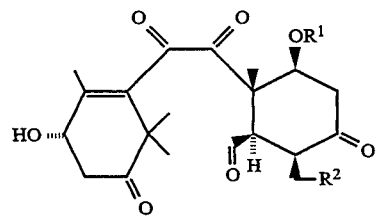

wherein R¹ is H, COR, R, or SiR₃; and R² is OSiR₃, SR, or SOR; wherein R is an alkyl or aryl group; which comprises:

(a) oxidizing a compound having the structure:

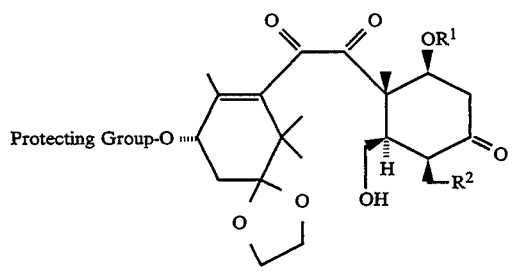

wherein R¹ is H, COR, R, or SiR₃; and R² is OSiR₃, SR, or SOR; wherein R is an alkyl or aryl group; under suitable conditions to form an aldehyde having the structure:

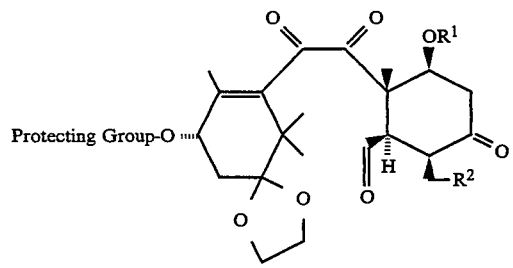

and (b) deketalizing the aldehyde formed in step (a) under suitable conditions to form the compound having the structure:

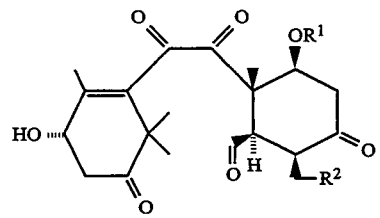

In step (a), the starting compound is preferably oxidized using oxalyl chloride and DMSO followed by triethylamine to form the aldehyde. In step (b), the deketalizaton preferably involves treating the ketal with p-toluenesulfonic acid in aqueous tetrahydrofuran to form the compound in which the protecting group, preferably the TBDMS ether, is concomitantly removed.

The present invention further provides a process for synthesizing a compound having the structure:

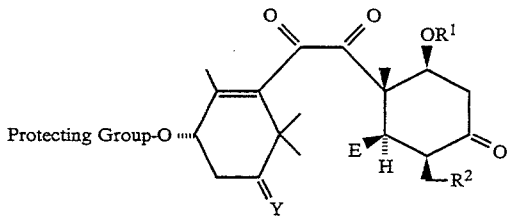

wherein Y is O or —OCH$_2$CH$_2$O—; E is —CH$_2$OR', CN, CO$_2$R or CHO; R$^1$ is H, COR, R, or SiR$_3$; and R$^2$ is OSiR$_3$, SR, or SOR; wherein R' is H, COR, R, or SiR$_3$ and R is an alkyl or aryl group; which comprises coupling a diketo dienophile having the structure:

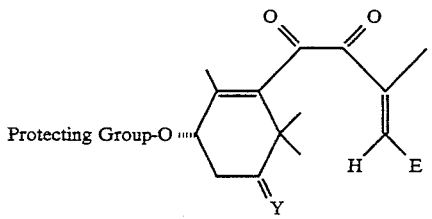

wherein Y is O or —OCH$_2$CH$_2$O—; and E is —CH$_2$OR', CN, CO$_2$R or CHO; wherein R' is H, COR, R, or SiR$_3$ and R is an alkyl or aryl group; with a diene having the structure:

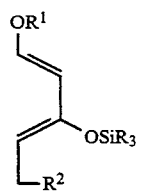

wherein R$^1$ is H, COR, R, or SiR$_3$; and R$^2$ is OSiR$_3$, SR, or SOR; wherein R is an alkyl or aryl group; to form the compound having the structure:

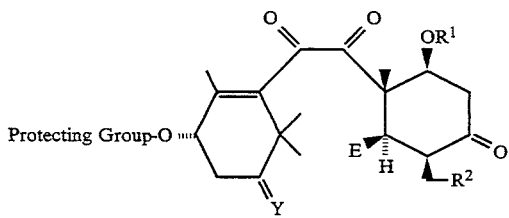

In process above, Diels-Alder cycloaddition of the diketo dienophile with the diene followed by acidic work-up yields an adduct in which the primary silyl ether is selectively cleaved affording the alcohol. Alternatively, fluoride mediated work-up of the Diels-Alder reaction between the diketo dienophile and the diene produces the compound directly.

The present invention also provides a process for synthesizing a diketo dienophile having the structure:

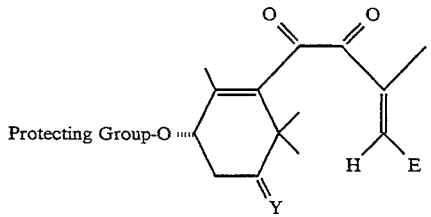

wherein Y is O or —OCH$_2$CH$_2$O—; and E is —CH$_2$OR', CN, CO$_2$R, or CHO; wherein R' is H, COR, R, or SiR$_3$ and R is an alkyl or aryl group; which comprises:

(a) coupling an aldehyde having the structure:

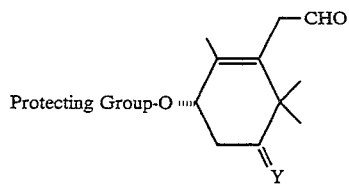

wherein Y is O or —OCH$_2$CH$_2$O—; with a compound having the structure:

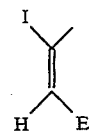

wherein E is —CH$_2$OR', CN, CO$_2$R or CHO; wherein R' is H, COR, R, or SiR$_3$ and R is an alkyl or aryl group; under suitable conditions to form an allylic alcohol having the structure:

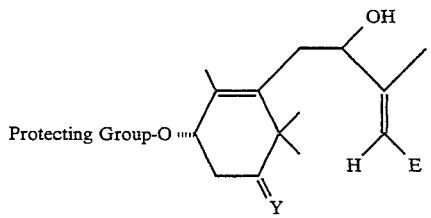

(b) oxidizing the allylic alcohol formed in step (a) under suitable conditions to form an enone having the structure:

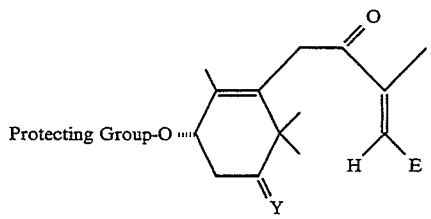

(c) treating the enone formed in step (b) under suitable conditions to form a hydroxyketone having the structure:

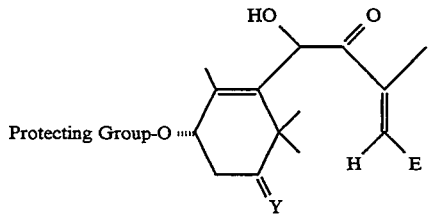

and (d) oxidizing the hydroxyketone formed in step (c) under suitable conditions to form the diketo dienophile having the structure:

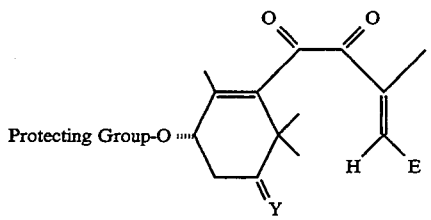

In step (a), the coupling is preferably performed by a nickel chloride catalyzed chromium (II) chloride promoted coupling of the iodide compound, preferably vinyl iodide, with the aldehyde to afford the allylic alcohol. In step (b), the alcohol is preferably oxidized by Swern oxidation (oxalyl chloride, dimethylsulfoxide, triethylamine, dichloromethane) to form the enone, which is converted in step (c) into the hydroxyketone by preferably adding KHMDS followed by N-phenyl-sulfonyl-phenyloxaziridine. In step (d), the hydroxyketone is preferably oxidized using oxalyl chloride and DMSO followed by triethylamine to form the diketo dienophile.

The present invention also provides a process for synthesizing a compound having the structure:

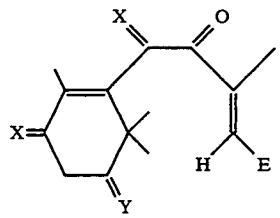

wherein each X is independently the same or different and is H, OH, O, OR, or $OSiR_3$; Y is O or $-OCH_2C-H_2O-$; and E is H, $-CH_2OR'$, CN, $CO_2R$, or CHO; wherein R' is H, COR, R, or $SiR_3$ and R is an alkyl or aryl group; which comprises coupling an aldehyde having the structure:

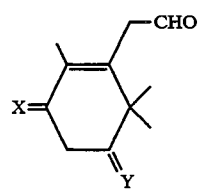

wherein X is H, OH, O, OR, or $OSiR_3$; and Y is O or $-OCH_2CH_2O-$; wherein R is an alkyl or aryl group; with a compound having the structure:

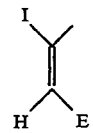

wherein E is $-CH_2OR'$, CN, $CO_2R$, or CHO; wherein R' is H, COR, R, or $SiR_3$ and R is an alkyl or aryl group; under suitable conditions to form the compound having the structure:

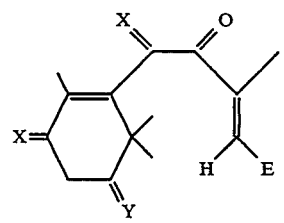

The present invention also provides a process for synthesizing a compound having the structure:

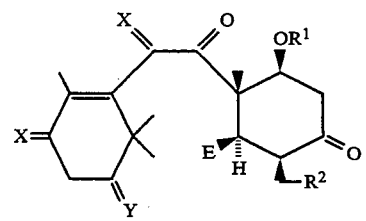

wherein each X is independently the same or different and is H, OH, O, OR, or $OSiR_3$; Y is O or $-OCH_2C-H_2O-$; E is H, $-CH_2OR'$, CN, $CO_2R$, or CHO; $R^1$ is H, COR, R, or $SiR_3$; and $R^2$ is $OSiR_3$, SR, or SOR; wherein R' is H, COR, R, or $SiR_3$ and R is an alkyl or aryl group; which comprises contacting a compound having the structure:

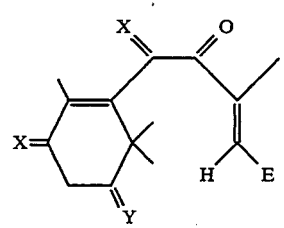

wherein each X is independently the same or different and is H, OH, O, OR, or $OSiR_3$; Y is O or $-OCH_2C-H_2O-$; and E is H, $-CH_2OR'$, CN, $CO_2R$, or CHO; wherein R' is H, COR, R, or $SiR_3$ and R is an alkyl or aryl group; with a compound having the structure:

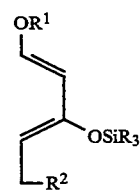

wherein $R^1$ is H, COR, R, or $SiR_3$; and $R^2$ is $OSiR_3$, SR, or SOR; wherein R is an alkyl or aryl group; under suitable conditions to form the compound having the structure:

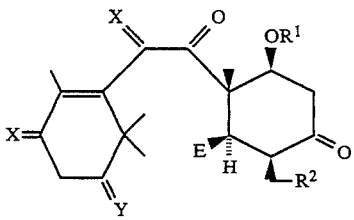

The present invention also provides a process for synthesizing a compound having the structure:

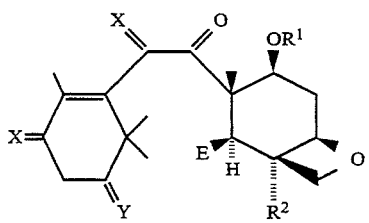

wherein each X is independently the same or different and is H, OH, O, OR, or OSiR$_3$; Y is O or —OCH$_2$CH$_2$O—; E is H, —CH$_2$OR', CN, CO$_2$R, or CHO; R$^1$ is H, COR, or SiR$_3$; and R$^2$ is H, COR, or SiR$_3$; wherein R' is H, COR, R, or SiR$_3$ and R is an alkyl or aryl group; which comprises treating a compound having the structure:

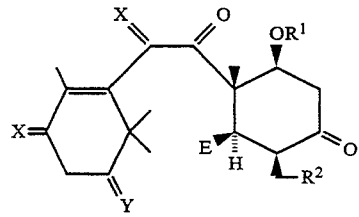

wherein each X is independently the same or different and is H, OH, O, OR, or OSiR$_3$; Y is O or —OCH$_2$CH$_2$O—; E is H, —CH$_2$OR', CN, CO$_2$R, or CHO; R$^1$ is H, COR, R, or SiR$_3$; and R$^2$ is OSiR$_3$, SR, or SOR; wherein R' is H, COR, R, or SiR$_3$ and R is an alkyl or aryl group; under suitable conditions to form the compound having the structure:

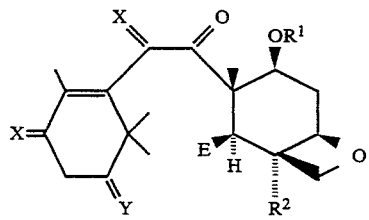

The present invention also provides a process for synthesizing a compound having the structure:

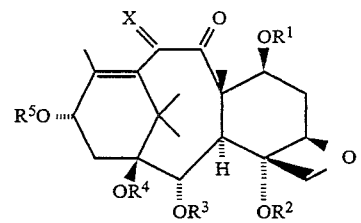

wherein X is H, OH, O, OR, or OSiR$_3$; and R$^1$, R$^2$, R$^3$, R$^4$, and R$^5$ are independently the same or different and are H, COR, SiR$_3$, or R; wherein R is an alkyl or aryl group; which comprises treating a compound having the structure:

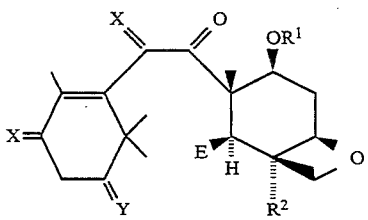

wherein each X is independently the same or different and is H, OH, O, OR, or OSiR$_3$; Y is O or —OCH$_2$CH$_2$O—; E is H, —CH$_2$OR', CN, CO$_2$R, or CHO; R$^1$ is H, COR, or SiR$_3$; and R$^2$ is H, COR, or SiR$_3$; wherein R' is H, COR, R, or SiR$_3$ and R is an alkyl or aryl group; under suitable conditions to form the compound having the structure:

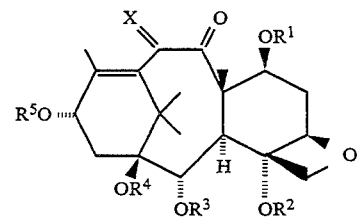

The present invention also provides a compound having the structure:

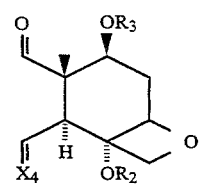

wherein X$_4$ is H, OR, O, —OCH$_2$CH$_2$O—, or —SCH$_2$CH$_2$CH$_2$S—; and R$_2$ and R$_3$ are independently the same or different and are H, acyl, alkyl, aryl, TBS, TES, TMS, or TBDPS; wherein R is H, acyl, alkyl, aryl, TBS, TES, TMS, or TBDPS.

The present invention further provides a compound having the structure:

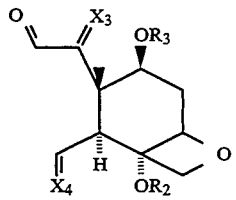

wherein $X_3$ and $X_4$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS.

In addition, the present invention provides a compound having the structure:

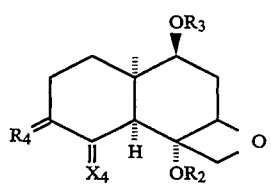

wherein $X_4$ is H, OR, O, —OCH$_2$CH$_2$O—, or —SCH$_2$CH$_2$CH$_2$S—; $R_2$ and $R_3$ are independently the same or different and are H, acyl, alkyl, aryl, TBS, TES, TMS, or TBDPS; and $R_4$ is PhCH(BzNH)CH(OH)CO—, O, an alkyl, or aryl group; wherein R is H, acyl, alkyl, aryl, TBS, TES, TMS, or TBDPS.

The present invention also provides a compound having the structure:

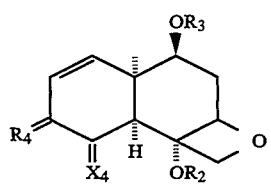

wherein $X_4$ is H, OR, O, —OCH$_2$CH$_2$O—, or —SCH$_2$CH$_2$CH$_2$S—; $R_2$ and $R_3$ are independently the same or different and are H, acyl, alkyl, aryl, TBS, TES, TMS, or TBDPS; and $R_4$ is PhCH(BzNH)CH(OH)CO—, O, an alkyl, or aryl group; wherein R is H, acyl, alkyl, aryl, TBS, TES, TMS, or TBDPS.

The present invention also provides a compound having the structure:

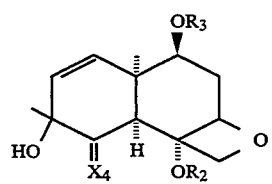

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a compound having the structure:

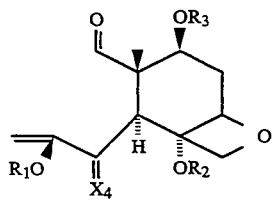

wherein $X_4$ is H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention further provides a compound having the structure:

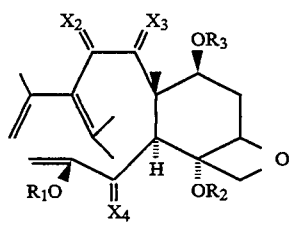

wherein $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS.

Moreover, the present invention provides a compound having the structure:

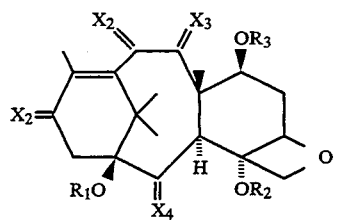

wherein $X_1$, $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a compound having the structure:

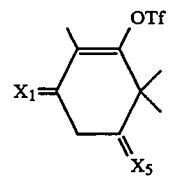

wherein $X_1$ and $X_5$ are independently the same or different and are H, OR, O, —OCH$_2$CH$_2$O—, or —SCH$_2$CH$_2$CH$_2$S—; wherein R is H, acyl, alkyl, aryl, TBS, TES, TMS, or TBDPS.

The present invention also provides a compound having the structure:

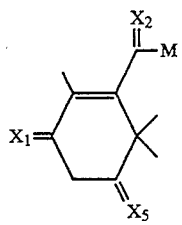

wherein $X_1$, $X_2$, and $X_5$ are independently the same or different and are H, OR, O, —OCH$_2$CH$_2$O—, or —SCH$_2$CH$_2$CH$_2$S—; and M is H or a metal; wherein R is H, acyl, alkyl, aryl, TBS, TES, TMS, or TBDPS.

The present invention further provides a compound having the structure:

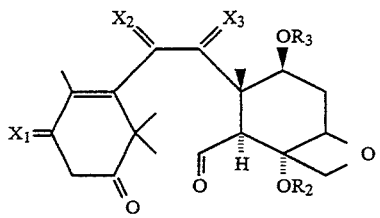

wherein $X_1$, $X_2$, and $X_3$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS.

The present invention also provides a process for synthesizing a compound having the structure:

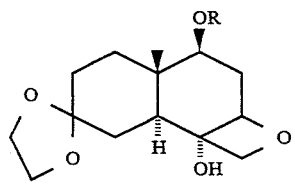

wherein R is H or TBS; which comprises:
(a) treating a compound having the structure:

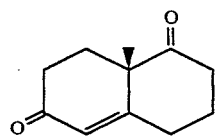

under suitable conditions to form a compound having the structure:

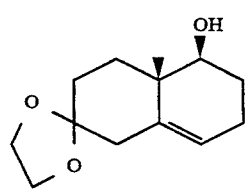

(b) contacting the compound formed in step (a) with TBS under suitable conditions to form a compound having the structure:

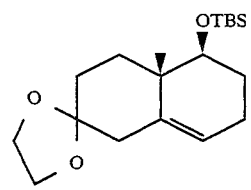

(c) contacting the compound formed in step (b) under suitable conditions to form a compound having the structure:

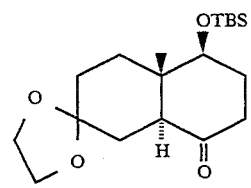

(d) triflating the compound formed in step (c) under suitable conditions to form a compound having the structure:

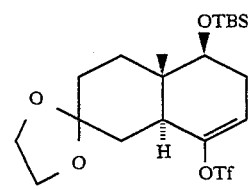

(e) treating the compound, formed in step (d) by carbomethoxylation under suitable conditions to form a compound having the structure:

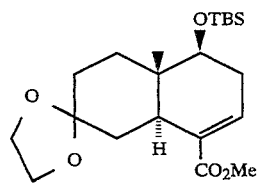

(f) reducing the compound formed in step (e) under suitable conditions to form a compound having the structure:

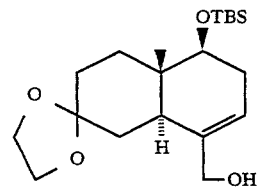

(g) treating the compound formed in step (f) by oxmylation under suitable conditions to form a compound having the structure:

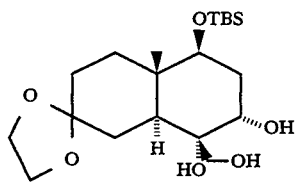

and (h) contacting the compound formed in step (g) under suitable conditions to form the compound having the structure:

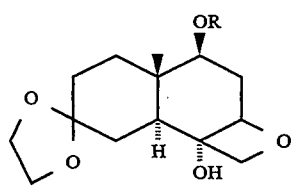

In step (a), the starting compound is treated by deconjugative ketalization and hydroboration/oxidation. In step (b), the equatorial secondary alcohol of the compound formed in step (a) (a pro C-7 hydroxyl in the C-ring of taxol) is protected by treating with t-butyldimethylsilyl (TBS) ether. In step (c), the treating comprises the hydroboration/oxidization of the compound formed in step (b) according to the reported protocol (33), followed by tetrapropylammonium perruthenate catalyzed oxidation (39, 40) to give the cis and trans-fused ketones which converge to the trans compound after base catalyzed equilibration. In step (d), for the purpose of one carbon homologation, the compound formed in step (c) is converted to the enol triflate, preferably by O-sulfonylation of its potassium enolate with N-phenyltrifluoromethane sulfonimide (41, 42, 43). In step (e), the treating comprises palladium catalyzed carbomethoxylation (44) to yield the unsaturated ester. In step (f), this ester is readily reduced with a reducing agent, preferably, DIBAH, to the corresponding allylic alcohol. In step (g), the treating comprises the osmylation of the alcohol under catalytic conditions to yield the triol. In step (h), the triol is converted to the oxetane by preferably treating with TMSCl/pyridine in $CH_2Cl_2$, $Tf_2O$, and ethylene glycol (45). The TBS ether is removed with tetrabutylammonium fluoride.

The present invention also provides a process for synthesizing a compound having the structure:

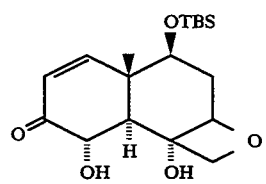

which comprises:
(a) synthesizing a compound having the structure according to the process above;
(b) removing the ketal of the compound formed in step (a) under suitable conditions to form a compound having the structure:

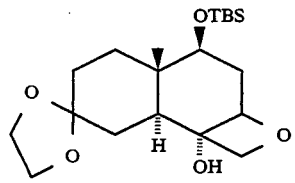

(c) treating the compound formed in step (b) under suitable conditions to form a compound having the structure:

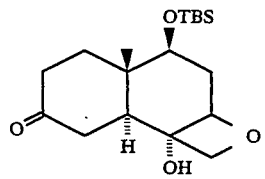

(d) treating the compound formed in step (c) under suitable conditions to form a compound having the structure:

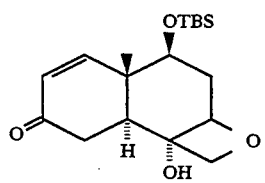

and (e) treating the compound formed in step (d) under suitable conditions to form the compound having the structure:

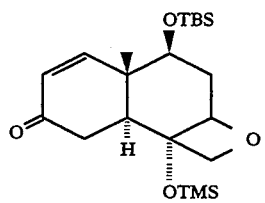

In step (a), the compound is synthesized by the process above or other processes determinable by those skilled in the art. In step (b), the ketal is removed under mildly acidic conditions (collidinium tosylate) to maintain the integrity of both the TBS ether and the oxetane ring. In step (c), the ketone is subsequently converted to the corresponding enone by treating its silyl enol ether (46) with $Pd(OAc)_2$ (47, 48). In step (d), the tertiary alcohol of the compound is protected with TBS by treating with an excess of TBSCl, followed by the treatment of potassium bis(trimethylsilyl) amide in step (e).

The present invention also provides a process for synthesizing a compound having the structure:

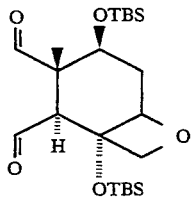

which comprises:

(a) synthesizing a compound having the structure

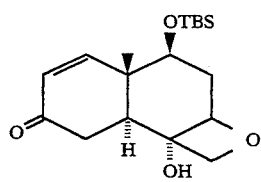

according to the suitable process above;

(b) treating the compound formed in step (a) under suitable conditions to form a compound having the structure:

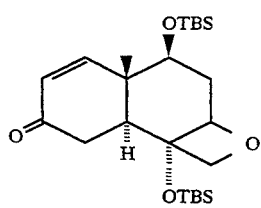

(c) treating the compound formed in step (b) under suitable conditions to form a compound having the structure:

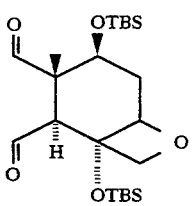

In step (a), the compound is synthesized by the relevant process above or other processes determinable by those skilled in the art. In step (b), the treating is effected by treatment with TBSCl/imidazole/DMF. In step (c), the treating is effected by degradation of the compound formed in step (b) to the dialdehyde by ozonolysis of the trimethylsilyl dienol ether.

The present invention also provides a process for synthesizing a compound having the structure:

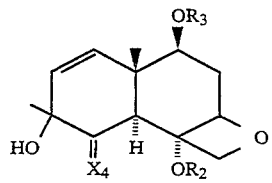

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; which comprises treating a compound having the structure:

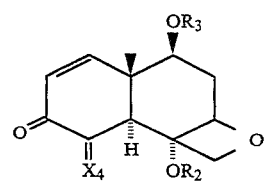

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; under suitable conditions to form the compound having the structure:

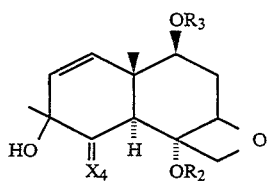

In the process above, the treating comprises methyllithium (Et$_2$O/−78° C.) addition.

The present invention also provides a process for synthesizing a compound having the structure:

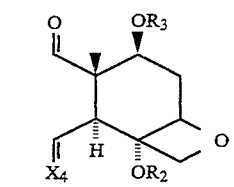

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; which comprises treating a compound having the structure:

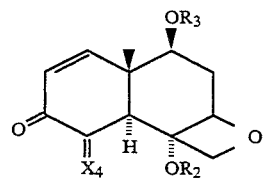

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; under suitable conditions to form the compound having the structure:

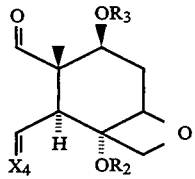

The present invention also provides a process for synthesizing a compound having the structure:

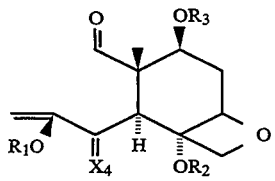

wherein $X_4$ is H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS;
which comprises:
(a) synthesizing a compound having the structure:

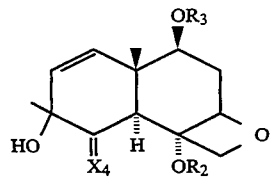

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable process above;
and (b) treating the compound formed in step (a) under suitable conditions to form the compound having the structure:

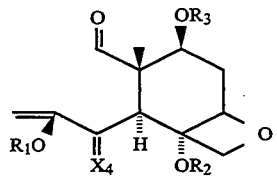

In step (a), the compound may be synthesized by the relevant process above or other processes determinable by those skilled in the art. The treating in step (b) involves degradation by ozonolysis followed by lead tetraacetate.

The present invention also provides a process for synthesizing a compound having the structure:

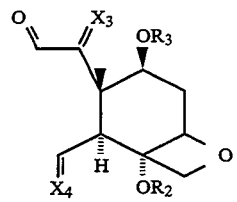

wherein $X_3$ and $X_4$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS;
which comprises:
(a) synthesizing a compound having the structure:

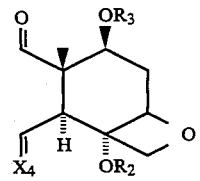

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable process above;
and (b) treating the compound formed in step (a) under suitable conditions to form the compound having the structure:

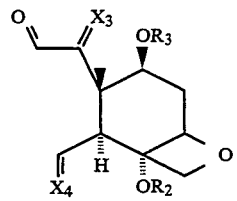

In step (a), the compound may be synthesized by the relevant process above or other processes determinable by those skilled in the art. The treating in step (b) involves homologation by methoxymethylene Wittig followed by oxidation.

The present invention also provides a process for synthesizing a compound having the structure:

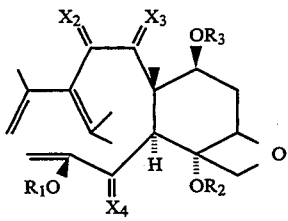

wherein $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS; which comprises:

(a) synthesizing a compound having the structure:

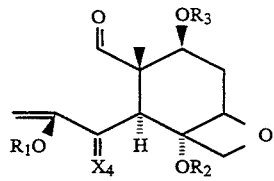

wherein $X_4$ is H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable process above; and (b) contacting the compound formed in step (a) with a compound having the structure:

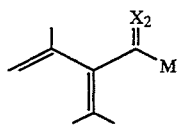

wherein $X_2$ is H, OR, O, —OCH$_2$CH$_2$O—, or —SCH$_2$CH$_2$CH$_2$S—; and M is a metal; wherein R is H, acyl, alkyl, aryl, TBS, TES, TMS, or TBDPS; under suitable conditions to form the compound having the structure:

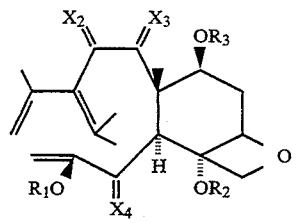

In step (a), the compound may be synthesized by the suitable process above or other processes determinable by those skilled in the art. The contacting in step (b) comprises the nucleophilic attack of the compound synthesized in step (a) with the compound in step (b).

The present invention also provides a process for synthesizing a compound having the structure:

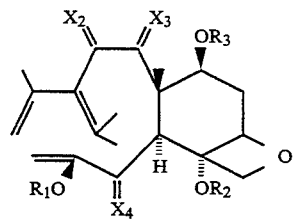

wherein $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS; which comprises:

(a) synthesizing a compound having the structure:

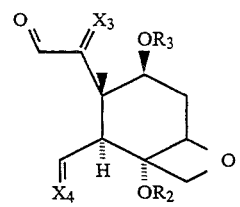

wherein $X_3$ and $X_4$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable process above;

(b) contacting the compound formed in step (a) with a compound having the structure:

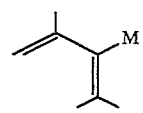

wherein M is a metal; under suitable conditions to form the compound having the structure:

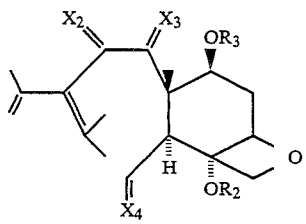

wherein $X_2$, $X_3$, and $X_4$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS;

and (c) contacting the compound formed in step (b) with a compound having the structure:

wherein $R_1$ is H, acyl, alkyl, aryl, TBS, TES, TMS, or TBDPS; and M is a metal; under suitable conditions to form the compound having the structure:

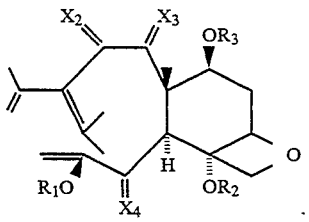

In step (a), the compound may be synthesized by the suitable process above or other processes determinable by those skilled in the art. The contacting in step (b) involves the addition of the metallated diene to the aldehyde function of the compound formed in step (a). The contacting in step (c) involves the addition of the two carbon acyl-anion to the compound formed in step (b).

The present invention also provides a process for synthesizing a compound having the structure:

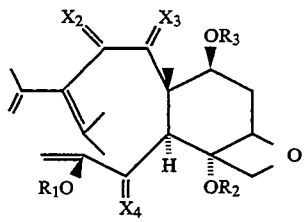

wherein $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS;

which comprises:

(a) synthesizing a compound having the structure:

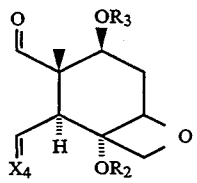

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable process above;

(b) contacting the compound formed in step (a) with a compound having the structure:

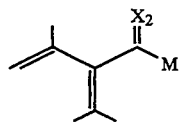

wherein $X_2$ is H, OR, O, —OCH$_2$CH$_2$O—, or —SCH$_2$CH$_2$CH$_2$S—; and M is a metal; wherein R is H, acyl, alkyl, aryl, TBS, TES, TMS, or TBDPS; under suitable conditions to form the compound having the structure:

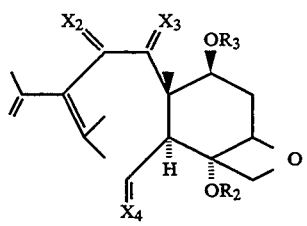

wherein $X_2$, $X_3$, and $X_4$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS;

and (c) contacting the compound formed in step (b) with a compound having the structure:

wherein $R_1$ is H, acyl, alkyl, aryl, TBS, TES, TMS, or TBDPS; and M is a metal; under suitable conditions to form the compound having the structure:

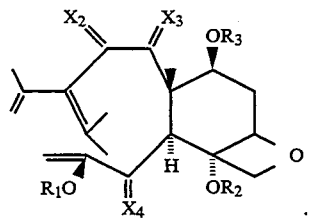

In step (a), the compound may be synthesized by the suitable process above or other processes determinable by those skilled in the art. The contacting in step (b) involves the addition of the metallated diene to the aldehyde function of the compound formed in step (a). The contacting in step (c) involves the addition of the two carbon acyl-anion, preferably, methoxyvinyllithium, to the compound formed in step (b).

The present invention also provides a process for synthesizing a compound having the structure:

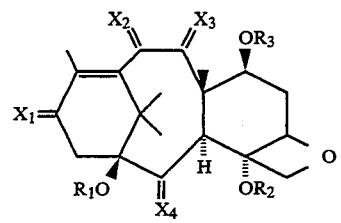

wherein $X_1$, $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS;

which comprises:

(a) synthesizing a compound having the structure:

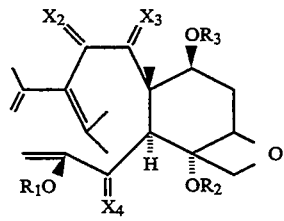

wherein $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS; according to one of the suitable processes above;

and (b) coupling the compound formed in step (a) by intra-molecular coupling under suitable conditions to form the compound having the structure:

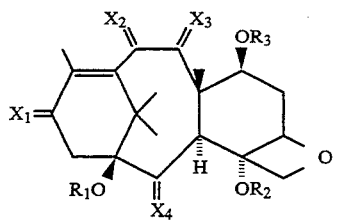

In step (a), the compound may be synthesized by the suitable processes above or other processes determinable by those skilled in the art. In step (b), the contacting comprises the intra-molecular Diels-Alder coupling of the compound formed in step (a) by thermal or Lewis acid catalyzed Diels-Alder cyclization.

The present invention further provides a process for synthesizing a compound having the structure:

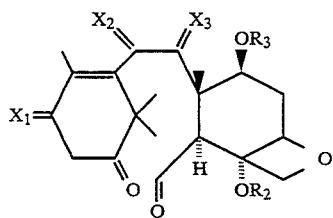

wherein $X_1$, $X_2$, and $X_3$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS;

which comprises:

(a) synthesizing a compound having the structure:

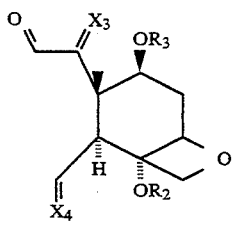

wherein $X_3$ and $X_4$ is H, OR, O, —OCH$_2$CH$_2$O—, or —SCH$_2$CH$_2$CH$_2$S—; and $R_2$ and $R_3$ are the independently the same or different and are H, acyl, alkyl, aryl, TBS, TES, TMS, or TBDPS; wherein R is H, acyl, alkyl, aryl, TBS, TES, TMS, or TBDPS; according to the suitable process above;

and (b) contacting the compound formed in step (a) with a compound having the structure:

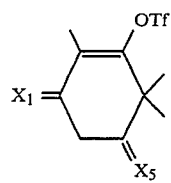

wherein $X_1$ and $X_5$ are independently the same or different and are H, OR, O, —OCH$_2$CH$_2$O—, or —SCH$_2$CH$_2$CH$_2$S—; wherein R is H, acyl, alkyl, aryl, TBS, TES, TMS, or TBDPS; under suitable conditions to form the compound having the structure:

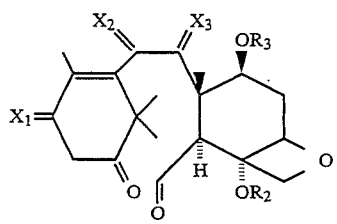

In step (a), the compound may be synthesized by the suitable process above or other processes determinable by those skilled in the art. In step (b), the contacting is performed by Nozaki-Nishi (13,14) coupling of the enol triflate with the compound formed in step (a).

The present invention also provides a process for synthesizing a compound having the structure:

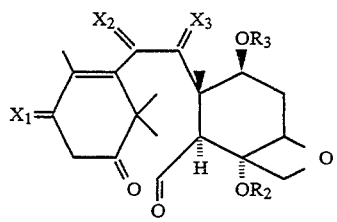

wherein $X_1$, $X_2$, and $X_3$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS;

which comprises:

(a) synthesizing a compound having the structure:

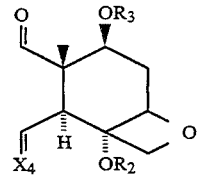

wherein $X_4$ is H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable process above;

and (b) contacting the compound formed in step (a) with a compound having the structure:

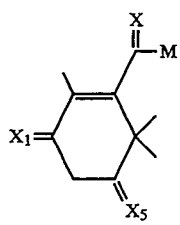

wherein $X_1$, $X_2$, and $X_5$ are independently the same or different and are H, OR, O, —OCH$_2$CH$_2$O—, or —SCH$_2$CH$_2$CH$_2$S—; and M is a metal; wherein R is H, acyl, alkyl, aryl, TBS, TES, TMS, or TBDPS; under suitable conditions to form a compound having the structure:

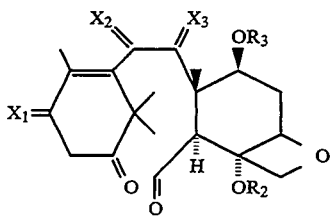

In step (a), the compound may be synthesized by the suitable process above or other processes determinable by those skilled in the art. In step (b), the contacting is performed by nucleophilic addition of the enol to the compound formed in step (a).

The present invention also provides a process for synthesizing a compound having the structure:

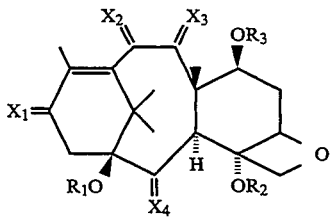

wherein $X_1$, $X_2$, $X_3$, and $X_4$ are independently the same or different and are H, OR, O, —OCH$_2$CH$_2$O—, or —SCH$_2$CH$_2$CH$_2$S—; and $R_1$, $R_2$, and $R_3$ are independently the same or different and are H, acyl, alkyl, aryl, TBS, TES, TMS, or TBDPS; wherein R is H, acyl, alkyl, aryl, TBS, TES, TMS, or TBDPS;

which comprises:

(a) synthesizing a compound having the structure:

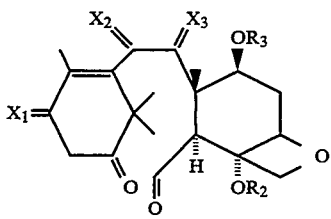

wherein $X_1$, $X_2$, $X_3$, and $X_4$ are independently the same or different and are H, OR, O, —OCH$_2$CH$_2$O—, or —SCH$_2$CH$_2$CH$_2$S—; and $R_2$ and $R_3$ are independently the same or different and are H, acyl, alkyl, aryl, TBS, TES, TMS, or TBDPS; wherein R is H, acyl, alkyl, aryl, TBS, TES, TMS, or TBDPS; according to the suitable processes above;

and (b) reacting the compound formed in step (a) by reductive coupling to form the compound having the structure:

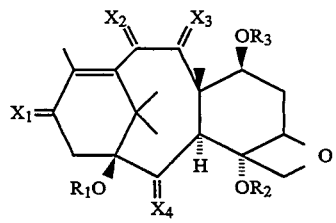

In step (a), the compound may be synthesized by the suitable processes above or other processes determinable by those skilled in the art. In step (b), the reacting is performed by reductive coupling using samarium(II) iodide or titanium(III) chloride.

The present invention also provides a process for synthesizing a compound having the structure:

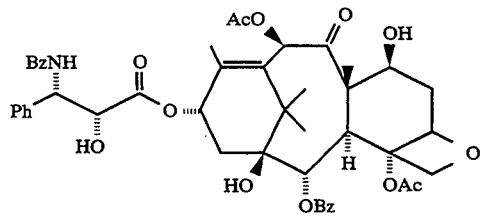

which comprises:

(a) synthesizing a compound having the structure:

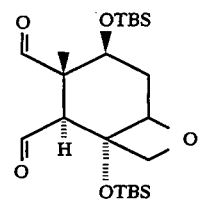

according to the suitable process above;

(b) treating the compound formed in step (a) under suitable conditions to form a compound having the structure:

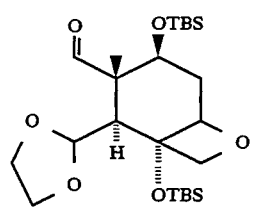

(c) contacting the compound formed in step (b) with lithiodithiane under suitable conditions to form a compound having the structure:

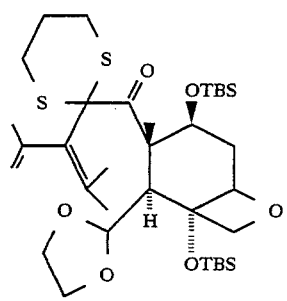

(d) deketalizing the compound formed in step (c) under suitable conditions to form a compound having the structure:

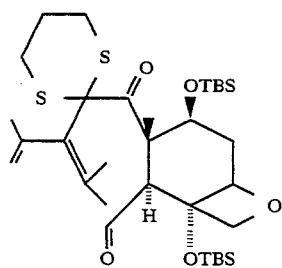

(e) contacting the compound formed in step (d) with methoxyvinyllithium under suitable conditions to form a compound having the structure:

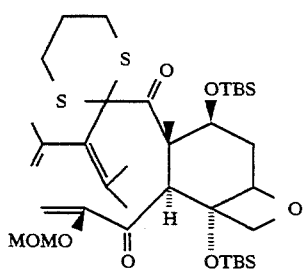

(f) heating the compound formed in step (e) under suitable conditions to form a compound having the structure:

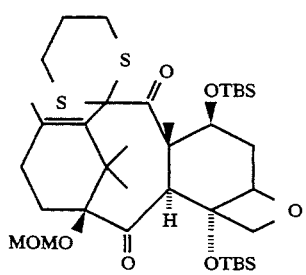

(g) reducing and esterifying the compound formed in step (f) under suitable conditions to form a compound having the structure:

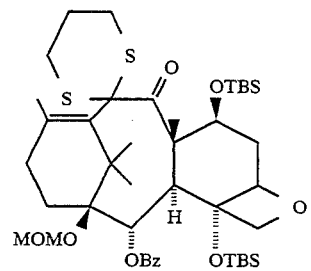

(h) oxidizing the compound formed in step (g) under suitable conditions to form a compound having the structure:

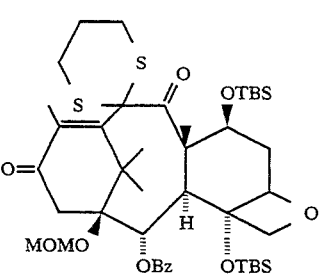

(i) removing the thioketal of the compound formed in step (h) under suitable conditions to form a compound having the structure:

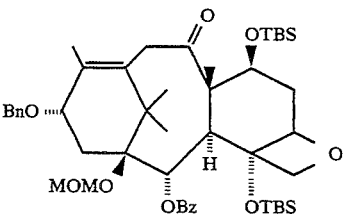

(j) treating the compound formed in step (i) under suitable conditions to form a compound having the structure:

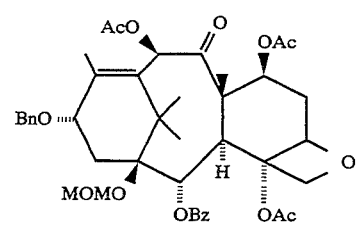

(k) treating the compound formed in step (j) under suitable conditions to form a compound having the structure:

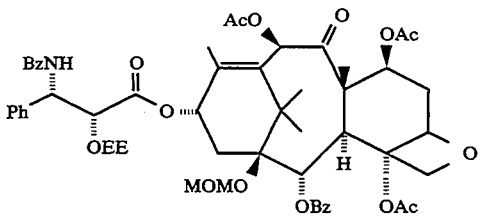

and (l) treating the compound formed in step (k) under suitable conditions to form the compound having the structure:

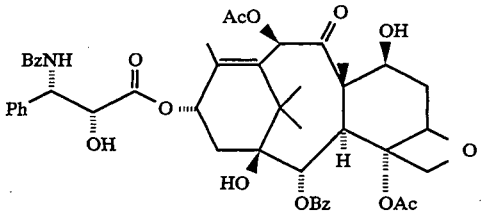

In step (a), the compound may be synthesized by the suitable process above or other processes determinable by those skilled in the art. In step (b), the treating comprises the selective ketalization of the less hindered aldehyde of step (a). In step (c), the contacting comprises the addition of lithiodithiane VII followed by Swern oxidation. In step (d), the contacting comprises deketalizing the compound formed in step (c) by the addition of acetone then PPTS. In step (e), the compound formed in step (d) is contacted with vinyllithium. In step (f), heating will cyclize the compound formed in step (e) to the tricyclic compound. In step (g), the compound formed in step (f) is reduced by stereoselective reduction after benzoylation of the newly generated ($\alpha$) secondary alcohol. In step (h), the compound formed in step (g) is oxidized by Allylic oxidation, followed by Swern oxidation if necessary. In step (i), the thioketal is removed by subsequent benzyl protection and Raney nickel reduction. In step (j), the treating comprises Franklin Davis hydroxylation of the potassium enolate of the compound formed in step (i) to give the corresponding hydroxyketone in which the oxaziridine approaches from the convex face. In step (k), the treating comprises fluoride induced desilyation with TBAF, peracetylation, hydrogenolysis of the benzyl ether and subsequent side chain coupling. In step (l), the treating comprises selectively removing the acetate at C-7, which in turn is doubly deprotected by simultaneous removal of the MOM and EE groups to give taxol.

The following Experimental Details Section is set forth to aid in an understanding of the invention. This section is not intended to, and should not be construed to, limit in any way the invention set forth in the claims which follow thereafter.

Experimental Details Section

General Procedures

All air and moisture sensitive reactions were performed in a flame-dried apparatus under an argon atmosphere unless otherwise noted. Air sensitive liquids and solutions were transferred via syringe or canula. Whenever possible, reactions were monitored by thin-layer chromatography (TLC). Gross solvent removal was performed in vacuo under aspirator on a Buchi rotary evaporator, and traces of solvent were removed on a high vacuum oil pump (0.1–0.5 mmHg).

Physical Data

Melting points (mp) were uncorrected and performed in soft glass capillary tubes using a Electrothermal series IA9100 digital melting point apparatus.

Infrared spectra (IR) were performed with a Perkin-Elmer 1600 series Fourier-Transform (FT). Samples were prepared as neat films on NaCl plates unless otherwise noted. Absorption bands are reported in wavenumbers ($cm^{-1}$), and are described in abbreviations: s=strong; m=medium; w=weak; br=broad. Only relevant, assignable bands are reported.

Proton nuclear magnetic resonance ($^1H$ NMR) spectra were determined using a Bruker AMX-400 spectrometer at 400 MHz. Chemical shifts are reported in parts per million ($\partial$) downfield from tetramethylsilane (TMS: $\partial=0$) using residual $CHCl_3$ as a lock reference ($\partial=7.25$). Resonances are presented in the following form: $\partial$ in ppm (multiplicity, coupling constant=J, integral). Multiplicities are abbreviated in the usual fashion: s=singlet; d=doublet; t=triplet; q=quartet; m=multiplet; br=a descriptor for a multiplicity meaning broad.

Carbon nuclear magnetic resonance ($^{13}C$ NMR) spectra were performed on a Bruker AMX-400 spectrometer at 100 MHz with composite pulse decoupling. Samples were prepared as with $^1H$ NMR and chemical shifts are reported in $\partial$ relative to TMS ($\partial=0$); the residual $CHCl3$ was used as an internal reference ($\partial=77.0$).

All mass spectral analyses were performed at Columbia University at the Department of Chemistry. High resolution mass spectra (HRMS) were determined by electron impact ionization (EI) on a JEOL JMS-DX 303HF mass spectrometer with perfluorokerosene (PFK) as an internal standard. Low resolution mass spectra (MS) were determined by either electron impact ionization (EI) or chemical ionization (CI) using the indicated carrier gas ($NH_3$ or $CH_4$) on a Delsi-Nermag R-10-10 mass spectrometer. For GCMS, a DB-5 fused capillary column (30 m, 0.25 m thickness) was used with helium as the carrier gas. Typical conditions were a temperature program from 60°–250° C. at 40° C./min.

Chromatography

Thin layer chromatography (TLC) was performed using precoated glass plates (silica gel 60, 0.25 mm thickness). Visualization was done by illumination with 254 nm UV lamp, or by immersion in anisaldehyde stain (9.2 mL p-anisaldehyde in 3.5 mL HOAc, 12.5 mL concentrated $H_2SO_4$ and 338 mL 95% EtOH) and heating to colorization.

Flash silica gel chromatography was carried out according to the protocol of Still (8).

Solvents and Reagents

Unless otherwise noted, all solvents and reagents were commercial grade and were used as received from the suppliers indicated in the experimentals. The following are exceptions, and all were distilled under Ar using the drying methods listed in parentheses: $CH_2Cl_2$ ($CaH_2$); PhH ($CaH_2$); THF (Na, PhCOPh as indicator); $Et_2O$ (Na, PhCOPh as indicator); diiopropylamine ($CaH_2$).

| Abbreviations | |
|---|---|
| Ac | acetyl |
| 9-BBN | borobicyclo[3.3.1]nonane |
| Bu | butyl |
| Bz | benzoyl |
| DMSO | dimethylsulfoxide |
| DMF | dimethylformamide |
| DMP | dimethylpyrazole |
| EE | ethoxy ethyl |
| KHMDS | potassium bis(trimethylsilyl)amide |
| LDA | lithium diisopropylamide |
| MOM | methoxy methyl |
| NMO | 4-methylmorpholine N-oxide |
| Ph | phenyl |
| PPTS | pyridinium p-toluenesulfonate |
| Pyr or Py | pyridine |
| TBAF | tetrabutylammonium fluoride |
| TBS or TBDMS | tert-butyldimethylsilyl |
| TBDPS | tert-butyldiphenylsilyl |
| TES | triethylsilyl |
| THF | tetrahydrofuran |
| TLC | thin-layer chromatography |
| TMS | trimethylsilyl |
| Tf | trifluoromethane sulfonate |

Route 1 Synthesis

Preparation of enol triflate 2

A solution of potassium bis(trimethylsilyl)amide (KHMDS, 12.9 g, 64.7 mmol, 1.5 eq) in tetrahydrofuran (anhydrous, 200 mL) was cooled to 0° C. under nitrogen using an ice-bath and was stirred for 15 minutes. To this solution was added dropwise a solution of the known ketoketal 1 (9) (8.546 g, 43.16 mmol, 1.0 eq) in tetrahydrofuran (50 mL) and the mixture was stirred for 2 hours at 0° C. until no more precipitate appeared. Then N-phenyl trifluoromethanesulfonimide (PhNTf$_2$, 25 g, 70 mmol, 1.62 eq) was added portionwise giving immediately a pale brown homogeneous solution. TLC (ethyl acetate/hexanes, 1:4) showed total disappearance of the starting ketoketal and formation of a slightly less polar product as well as N-phenyl trifluoromethanesulfonamide (PhNHTf), the by product derived from the imide. The solution was then warmed to room temperature, diluted with ether (200 mL) and washed with brine (2×100 mL). The aqueous layers were combined and washed with ether (2×200 mL) and the combined organic layers were dried over magnesium sulfate, filtered and concentrated in vacuo. The residue was chromatographed (600 mL of silica gel, 40–65μ, dichloromethane/hexanes, 1:3) to give 11.73 g (82.4%) of the triflate 2 as a pale yellow oil.

$^1$H NMR (CDCl$_3$, 400 MHz): ∂3.99 (s, 4H), 2.22 (brt, J=6.5 Hz, 2H), 1.80 (brt, J=6.5 Hz, 2H), 1.78 (s, 3H), 1.18 (s, 6H).

$^{13}$C NMR, CDCl$_3$, ∂17.42, 20.88, 26.56, 28.11, 44.48, 65.26, 111.42, 113.93, 117.10, 120.28, 123.45, 125.27, 146.77.

HRMS calcd. for C$_{12}$H$_{17}$O$_5$F$_3$S: 330.0749; found: 330.0735.

MS 41(38), 55(35), 69(30), 86(100), 165(56), 180(27), 330(10), 93(38), 99(41), 107(37), 137(25).

IR (neat, thin film, cm$^{-1}$) 2989.1, 2950.8, 2888.5, 1689.9, 1471.2, 1454.6, 1402.3.

R$_f$=0.56 (ethyl acetate/hexanes, 3:7).

Preparation of diene 3

To a solution of triflate 2 (8.43 g, 25.54 mmol, 1 eq), vinyltributylstannane (12.15 g, 11.2 mL, 38.32 mmol, 1.5 eq) and lithium chloride (anhydrous, 3.25 g, 76.64 mmol, 3 eq) in tetrahydrofuran (anhydrous, 150 mL) was added tetrakis(triphenylphosphine)palladium(O) (Pd(PPh$_3$)$_4$, 1.48 g, 1.28 mmol, 5 mol %) and the green mixture was refluxed for 24 hours. The mixture was then cooled to room temperature. Work up A: the mixture was diluted with ethyl acetate (50 mL) and washed with brine (2×100 mL). The aqueous layers were combined and extracted with ethyl acetate (3×50 mL) and the combined organic layers were dried over magnesium sulfate, filtered, concentrated under vacuum and purified by two successive silica gel chromatographies (each time 500 mL of silica gel, 40–65μ, ether/hexanes, 5:95) to give 4.85 g (91.4%) of the diene 3 as a pale yellow oil. To avoid the second chromatography due to the presence of a large quantity of chlorotributylstannane, basic treatment was employed: work up B: the majority of the by-product was removed by adding 1,8-diazabicyclo[5.4.0]undec-7-ene (DBU, 1.5 eq) after cooling the mixture to room temperature. It was then diluted with ether (600 mL) and washed with 1N sodium hydroxide (3×150 mL), brine (200 mL), dried over magnesium sulfate, filtered and concentrated in vacuo. The residue was triturated with ether (3×100 mL) and the combined etheral layers were concentrated in vacuo and found to be devoid of tin by-products. Flash chromatography (same conditions) gave similar yield of diene 3.

$^1$H NMR (CDCl$_3$, 400 MHz): ∂6.15 (m, 1H), 5.27 (dd, J=11.2, 2.6 Hz, 1H), 4.99 (dd, J=17.6, 2.6 Hz, 1H), 2.18 (m, 2H), 1.78 (t, J=6.7, 2H), 1.71 (d, J=0.9 Hz, 3H), 1.05 (s, 6H).

$^{13}$C NMR, CDCl$_3$, ∂20.92, 22.87, 26.70, 30.67, 42.04, 64.94, 112.08, 118.78, 126.98, 135.02, 137.46.

IR (neat, thin film, cm$^{-1}$) 3078.0, 2976.0, 2878.7, 1621.5, 1469.8, 1451.7.

HRMS calcd. for C$_{13}$H$_{20}$O$_2$: 208.1463; found 208.1459.

MS 41(35), 55(30), 86(30), 87(40), 107(100), 122(28), 208(51).

R$_f$=0.45 (ethyl acetate/hexanes 1:4).

Preparation of alcohol 4

A three-necked 500 mL flask was charged with a solution of the diene 3 (23 mmol, 4.79 g) in anhydrous tetrahydrofuran (25 mL), and then with a 9-borabicyclo[3.3.1]nonane (9-BBN, 0.5M solution in tetrahydrofuran, 138.2 mL, 69.1 mmol, 3 eq) and the mixture was immediately refluxed for 1.5 hours. TLC (ethyl acetate/hexanes, 1:1) showed total disappearance of the starting material. The mixture was then cooled to room temperature and ethanol (40 mL) was added, followed by 6N sodium hydroxide (15 mL), then dropwise 30% hydrogen peroxide (28 mL), maintaining a gentle reflux. After one hour, the mixture had cooled to room temperature, diluted with ether (100 mL) and washed with brine (2×200 mL). The aqueous layers were back extracted with ether (3×100 mL) and the combined organic layers were dried over magnesium sulfate, filtered and evaporated. Flash chromatography of the residue (silica gel, 40–65μ, 600 mL, ethyl acetate/hexanes, 1:5, then 1:4, then 1:3, then 1:2) gave pure alcohol 4 (4.886 g, 93.9%) as a pale yellow oil.

$^1$H NMR (CDCl$_3$, 400 MHz): ∂3.947–3.99 (m, 4H), 3.609 (t, J=8 Hz, 2H), 3.609 (t, J=8 Hz, 2H), 2.345 (t, J=8 Hz, 2H), 2.108 (t, J=6.6 Hz, 2H), 1.747 (t, J=6.7 Hz, 2H), 1.677 (s, 3H), 1.058 (s, 6H).

¹³C NMR, CDCl₃, ∂19.82, 22.72, 26.68, 30.60, 32.36, 40.09, 62.27, 64.84, 112.21, 128.43, 132.05.

IR (neat, thin film, cm⁻¹) 3471.5, 2953.2, 2882.3, 1477.1, 1379.6, 1355.5, 1208.4, 1140.6, 1089.2, 1056.0, 949.7, 906.2.

HRMS Calcd. for $C_{13}H_{22}O_3$: 226.1569; found: 226.1568.

MS 43(76), 55(39), 86(100), 87(75), 97(28), 107(28), 125(26), 196(20), 226(15).

$R_f$=0.43 (ethyl acetate:hexanes, 1:1).

Preparation of aldehyde 5

A 50 mL round bottom flask was charged with 5 mL of dichloromethane and 1 mL of a 2M solution of oxalyl chloride in dichloromethane (2 mmol, 2 eq), and the solution was cooled to −60° C. To this cooled solution was added dropwise dimethylsulfoxide (0.71 mL, 781 mg, 10 mmol, 5 eq) and the mixture was stirred 15 minutes at −60° C. A solution of the alcohol 4 (226 mg, 1 mmol, 1 eq) in dichloromethane (2 mL) was added dropwise, and the mixture was stirred at −60° C. for 15 minutes. Triethylamine (1.4 mL, 1.012 g, 10 mmol, 5 eq) was added and the mixture was allowed to warm to room temperature before being diluted with water (10 mL) and ether (10 mL). The aqueous phase was extracted with ether (10 mL) and the combined organic layers were washed with 0.1N hydrochloric acid (10 mL), then brine (10 mL), dried over magnesium sulfate, filtered and evaporated. Flash chromatography of the residue (silica gel, 40–65μ, 100 mL, ether/hexanes 15:85) gave pure aldehyde 5 (210 mg) in 93.7% yield, as a pale yellow oil.

¹H NMR (CDCl₃, 400 MHz): ∂9.535 (t, J=2.4 Hz, 1H), 3.948–4.031 (m, 4H), 3.116 (brs, 2H), 2.213 (t, J=6.6 Hz, 2H), 1.792 (t, J=6.6 Hz, 2H), 1.622 (s, 3H), 1.032 (s, 6H)

¹³C NMR, CDCl₃, ∂19.72, 22.38, 26.57, 30.70, 43.87, 64.79, 111.67, 127.80, 131.18, 200.65.

IR (neat, thin film, cm⁻¹) 2883.1, 2717.3, 1722.1, 1472.2, 1427.2, 1380.5, 1357.1, 1327.3, 1306.4, 1208.5, 1141.0, 1086.7, 1056.4, 991.4, 949.9, 906.2.

HRMS Calcd. for $C_{13}H_{20}O_3$: 224.1412; found: 224.1393.

MS 41(26), 73(20), 86(85), 87(100), 95(18), 224(48).

$R_f$=0.75 (ethyl acetate/hexanes, 1:1).

Preparation of alcohol 6

A dry 100 mL flask equipped with stir bar was charged with a solution of aldehyde 5 (1.0 gm; 4.5 mmol) in tetrahydrofuran (25 mL). The solution was cooled to 0° C., and a solution of the grignard reagent derived from 2-bromopropene (0.64M in tetrahydrofuran; 7.7 mL, 1.1 eq.) was added dropwise over 5 minutes. When the addition was complete the mixture was stirred at 0° C. an additional 30 minutes and then at room temperature for 30 minutes. TLC (ethyl acetate/hexanes, 1:5) indicated that all the starting aldehyde ($r_f$=0.27) had been consumed, and showed the appearance of a new product ($r_f$=0.14). Saturated ammonium chloride (40 mL) was added, and the mixture partitioned between ethyl acetate (100 mL) and water (100 mL). The aqueous phase was decanted and the organic phase washed with brine (2×100 mL), dried over anhydrous magnesium sulfate, filtered and the filtrate concentrated in vacuo. Purification of the residue by flash chromatography (150 mL of silica gel eluted with ethyl acetate/hexanes, 1:5) gave the allylic alcohol 6 (1.1 gm; 4.0 mmol; 89%) as a pale yellow oil.

¹H NMR (CDCl₃, 400 MHz): ∂5.00 (brs, 1H), 4.81 (brs, 1H), 4.22 (dd, J=10.2, 3.6 Hz, 1H), 3.92–4.02 (m, 4H), 2.42 (dd, J=14.2, 10.2 Hz, 1H), 2.08–2.32 (m, 4H), 1.80 (s, 3H), 1.73–1.88 (m, 2H), 1.72 (s, 3H), 1.11 (s, 3H), 1.10 (s, 3H).

¹³C NMR, CDCl₃, ∂17.87, 20.59, 22.73, 22.61, 29.60, 30.79, 35.25, 43.18, 64.89, 74.45, 109.88, 112.31, 130.62, 132.34, 147.71.

IR (neat, thin film, cm⁻¹) 3454.0, 2926.6, 1715.5, 1651.5, 1452.9, 1379.0, 1356.2, 1209.6, 1134.3, 1088.0, 1058.4, 991.6, 901.6.

HRMS Calcd for $C_{16}H_{26}O_3$: 266.1882; found: 266.1886.

MS 87(70), 99(46), 109(23), 168(28), 196(45), 205(24), 235(18), 249(100), 266(4), 267(34).

$R_f$=0.43 (ethyl acetate/hexanes, 1:1).

Preparation of enone 7

A 2M solution of oxalyl chloride in dichloromethane (170 μL, 0.34 mmol, 2 eq) in 1 mL of anhydrous dichloromethane were cooled under nitrogen to −60° C. Dimethylsulfoxide (71 μl, 6 eq) was added, and after 15 minutes, a solution of the alcohol 6 (45 mg, 0.17 mmol, 1 eq) in dichloromethane (1 mL). After 30 minutes, triethylamine (0.5 mL, excess) was added, and the mixture was allowed to warm to room temperature. It was then diluted with ether and water (5 mL each) and the etheral layer was washed with 0.1N hydrochloric acid (10 mL). The aqueous phase was then extracted with ether (2×5 mL) and the combined organic layers were washed with brine, dried over magnesium sulfate, filtered, and evaporated. Flash chromatography of the residue (100 mL of silica gel, 40–65μ, ethyl acetate/hexanes, 1:4) gave 43 mg (96%) of the enone 7 as a pale yellow oil.

¹H NMR (CDCl₃, 400 MHz): ∂6.00 (brs, 1H), 5.74 (brs, 1H), 3.92–4.02 (m, 4H), 3.47 (brs, 2H), 2.20 (brt, J=6.4 Hz, 2H), 1.89 (s, 3H), 1.79 (t, J=6.6 Hz, 2H), 1.49 (s, 3H), 0.97 (s, 6H).

¹³C NMR, CDCl₃, ∂17.94, 20.10, 22.53, 26.76, 30.55, 37.07, 42.98, 64.88, 112.09, 123.27, 129.68, 130.07, 144.82, 199.04.

IR (neat, thin film, cm⁻¹) 2926.5, 1686.1, 1452.0, 1336.0, 1208.5, 1130.1, 1088.6, 1063.6, 902.4.

HRMS Calcd for $C_{16}H_{24}O_3$: 264.1725; found: 264.1719.

MS 69(85), 86(100), 87(51), 99(25), 109(30), 135(25), 150(23), 163(18), 178(24), 221(16), 264(32).

$R_f$=0.65 (ethyl acetate/hexanes, 1:1).

Preparation of adduct 8

A solution of enone 7 (28 mg, 0.106 mmol) and diene (0.424 mmol, 4 eq) in deuterated benzene (0.5 mL) was added into a base washed sealable NMR tube. The extent of the reaction was monitored by studying the disappearance of the starting enone by NMR of the whole mixture. After 2.5 days at 125° C., the pale brown solution did not contain any more starting material and showed a 2:1 ratio of 2 products. The mixture was evaporated to dryness and treated with a 0.1N hydrochloric acid/tetrahydrofuran mixture (1 mL, 1:4 vol) and stirred at room temperature for 30 minutes. The mixture was then poured into a saturated hydrogenocarbonate solution (5 mL) and extracted with dichloromethane (3×10 mL). The combined organic layers were dried over magnesium sulfate, filtered and evaporated. Flash chromatography of the residue (100 mL of silica gel, ethyl acetate/hexanes, 1:2) gave 28.5 mg of enone 8 (81%) as a pale yellow oil.

$^1$H NMR (CDCl$_3$, 400 MHz): $\partial$7.02 (dd, J=10.2, 1.05 Hz, 1H), 6.05 (d, J=10.2 Hz, 1H), 3.92–4.02 (m, 4H), 3.31 (s, 2H), 2.54 (m, 1H), 2.43 (m, 2H), 2.20 (t, J=6.6 Hz, 2H), 1.91 (m, 1H), 1.78 (t, J=6.6 Hz, 2H), 1.43 (s, 3H), 1.42 (s, 3H), 0.94 (s, 3H), 0.93 (s, 3H).

$^{13}$C NMR, CDCl$_3$, $\partial$15.24, 19.96, 22.52, 25.24, 26.68, 30.54, 32.63, 34.79, 38.83, 42.80, 49.95, 64.91, 111.85, 128.60, 129.21, 130.44, 152.24, 198.43, 206.76.

IR (neat, thin film, cm$^{-1}$) 2924.4, 1716.1, 1679.9, 1604.4, 1456.1, 1356.7, 1270.8, 1088.8, 1057.2.

MS 41(18), 55(19), 67(19), 79(22), 81(41), 86(100), 87(53), 109(80), 110(93), 121(40), 137(70), 195(32), 223(40), 289(23), 332(92).

HRMS Calcd for C$_{20}$H$_{28}$O$_4$: 332.1988; found: 332.1960.

R$_f$=0.36 (ethyl acetate/hexanes 1:1).

Preparation of trione 9

The ketal 8 (183 mg, 0.55 mmol) was stirred 3 hours at 45° C. in 4 mL of a 1:1 vol mixture of tetrahydrofuran and water in presence of p-toluenesulfonic acid (104 mg, 0.55 mmol). NMR analysis of aliquots allowed monitoring of the reaction. After three hours, all the starting ketal has disappeared. The mixture was then diluted with ether (20 mL), washed with sodium hydrogenocarbonate (sat., 20 mL). The aqueous layer was extracted with ether (20 mL) and the combined organic layers were washed with brine (20 mL), dried over magnesium sulfate, filtered and evaporated, to give pure deketelized product 9 (141.4 mg, 89.1%), as a colorless oil.

$^1$H NMR (CDCl$_3$, 400 MHz): $\partial$7.04 (dd, J=10.2, 1.2 Hz, 1H), 6.08 (d, J=10.2 Hz, 1H), 3.36 (brs, 2H), 2.50–2.63 (m, 3H), 2.40–2.49 (m, 4H), 1.96 (ddd, J=10.5, 13.2, 5.2 Hz, 1H), 1.53 (s, 3H), 1.53 (s, 3H), 1.45 (s, 3H), 1.054 (s, 3H), 1.047 (s, 3H).

$^{13}$C NMR, CDCl$_3$, $\partial$20.00, 24.13, 24.16, 25.06, 31.38, 32.47, 34.62, 35.80, 38.76, 47.28, 49.87, 128.61, 129.30, 131.64, 151.79, 198.07, 206.62, 214.11.

IR (thin film, cm$^{-1}$) 2968.8, 2927.7, 2871.4, 1712.6, 1682.7, 1605.6, 1463.4, 1415.0, 1377.7, 1323.2, 1228.6, 1091.9, 1032.7, 1018.5, 807.1.

MS 41(28), 43(19), 53(20), 55(18), 67(17), 79(19), 81(50), 110(100), 123(53), 136(5), 151(8), 288(20).

HRMS Calcd for C$_{18}$H$_{24}$O$_3$: 288.1725; found: 288.1716.

R$_f$=0.36 (ethyl acetate/hexanes 1:1).

Preparation of Compound 10

To a solution of enone 9 (45 mg, 0.156 mmol) in benzene (anhydrous 2 mL) was added dropwise at room temperature 1.1 mL of a 1M solution of diethylaluminium cyanide in toluene (7 eq). After 10 minutes at room temperature, 1N sodium hydroxide was added (5 mL) and the mixture was stirred vigorously. Dichloromethane (5 mL) was added, and the aqueous phase was extracted with more dichloromethane (5 mL). The combined layers were washed with brine (10 mL), dried over magnesium sulfate, filtered and evaporated. Crude NMR showed a 3:1 ratio of 2 products as well as a small amount of remaining starting enone 9. Flash chromatography of the residue (50 mL of silica gel, 40–65μ, ethyl acetate/hexanes, 1:4–1:2) gave 3 fractions; starting enone 9 (9 mg, 20%), and two cyanides, trans (9 mg, 19%) and cis (28 mg, 57%) by comparison to the methyl group. Based on starting material recovery, the yield of cyanides products is 96%.

$^1$H NMR (CDCl$_3$, 400 MHz): $\partial$3.50 (d, J=19.1 Hz, 1H—AB system), 3.36 (d, J=19.1 Hz, 1H—AB system), 3.06 (dd, J=15, 10 Hz, 1H), 2.99 (dd, J=10, 4.6, 1H), 2.68 (dd, J=15, 4.6 Hz, 1H), 2.61 (t, J=6.7 Hz, 2H), 2.42–2.51 (m, 4H), 2.30–2.40 (m, 1H), 1.93–2.06 (m, 1H), 1.61 (s, 3H), 1.59 (s, 3H), 1.09 (s, 3H), 1.08 (s, 3H).

$^{13}$C NMR, CDCl$_3$, $\partial$20.16, 23.74, 24.22, 24.37, 31.47, 33.01, 35.88, 36.89, 37.12, 37.24, 40.04, 47.34, 49.39, 118.72, 128.08, 132.32, 204.35, 207.14, 213.96.

IR (neat, thin film, cm$^{-1}$) 2969.8, 2925.0, 2240.5, 1712.2, 1465.0, 1418.8, 1319.3, 1091.9, 1031.6, 1018.9, 916.1, 732.8.

MS 109(4), 123(9), 179(10), 273(15), 299(13), 315(27), 316(100), 317 (17).

HRMS Calcd. for C$_{19}$H$_{25}$O$_3$N: 315.1835; found: 315.1818.

R$_f$=0.18 (ethyl acetate/hexanes 1:1) (trans isomer of 10: 0.38)

Preparation of hydroxy enone 11

To a solution of potassium bis(trimethylsilyl)amide (KHMDS, 66 mg, 0.33 mmol, 3 eq) in tetrahydrofuran (anhydrous, 2 mL) cooled to −78° C. under nitrogen, was added a solution of the enone 7 (29 mg, 0.11 mmol, 1 eq) in tetrahydrofuran (3 mL). After 15 minutes, a solution of N-phenylsulfonyl phenyloxaziridine (86 mg, 0.33 mmol, 3 eq) was added to the green solution which was then decolored. The reaction was stirred 30 minutes at −78° C. before being quenched with saturated solution of ammonium chloride (2 mL) and warmed to room temperature. The mixture was diluted with ether (10 mL) washed with brine (10 mL), dried over magnesium sulfate, filtered and concentrated under reduce pressure. Flash chromatography of the residue (100 mL silica gel, 40–65μ, ethyl acetate/hexanes, 1:2) gave 26.7 mg of the hydroxyenone 11 (87%).

$^1$H NMR (CDCl$_3$, 400 MHz): $\partial$6.07 (s, 1H), 5.77 (brs, 1H), 5.08 (s, 1H), 4.15 (brs, 1H), 3.89–4.00 (m, 4H), 2.19 (t, J=6.6 Hz, 2H), 1.96 (d, J=0.7 Hz, 3H), 1.68–1.86 (m, 2H), 1.63 (s, 3H), 1.21 (s, 3H), 1.05 (s, 3H).

$^{13}$C NMR, CDCl$_3$, $\partial$18.83, 20.23, 22.98, 23.95, 26.54, 31.62, 43.74, 65.01, 74.56, 111.82, 125.95, 133.68, 135.87, 141.43, 204.31.

IR (neat, thin film, cm$^{-1}$) 3447.1, 2884.8, 1664.0, 1067.4, 1571.0, 1451.4, 1376.5, 1298.2, 1208.8, 1162.5, 1136.6, 1087.3, 1058.9, 1034.0, 949.5.

MS 41(100), 43(32), 69(32), 86(58), 107(100), 121(70), 149(43), 167(35), 211(82), 252(3), 280(20).

HRMS Calcd for C$_{16}$H$_{24}$O$_4$: 280.1675; found: 280.1676.

R$_f$=0.54 (ethyl acetate/hexanes, 1:1).

Preparation of compound 12

The glassware was washed with 1N sodium hydroxide, distilled water, and was then dried in the oven (140° C.). A sealable NMR tube containing a mixture of the enone 11 (23 mg, 0.082 mmol) and 1-methoxy-3-trimethylsilyloxy-1,3-butadiene (0.424 mmol, 5.2 eq) in a solution of deuterated benzene was heated 3 hours at 140° C. NMR analysis showed total disappearance of the starting enone, but no evidence of any Diels-Alder adducts were found in the spectrum. The mixture was then directly applied to a column of silica gel (50 mL, silica gel, 40–65μ, ethyl acetate/hexanes, 1:4) and eluted with the same solvent to give 23 mg (80%) of enone 12 as a pale yellow oil.

¹H NMR (CDCl₃, 400 MHz): δ5.07 (m, 1H), 5.05 (m, 1H), 4.74 (s, 1H), 3.92–4.03 (m, 4H), 2.11–2.27 (m, 2H), 1.75–1.92 (m, 2H), 1.79 (s, 3H), 1.61 (s, 3H), 1.21 (s, 3H), 1.035 (s, 3H), 0.14 (s, 9H).

¹³C NMR, CDCl₃, δ0.03, 18.05, 21.33, 22.52, 24.53, 26.69, 30.37, 41.28, 65.13, 83.28, 111.43, 115.79, 130.44, 130.87, 143.02, 207.40.

IR (neat, thin film, cm⁻¹) 2955.9, 1694.8, 1250.4, 1101.9, 889.0, 842.7.

MS 73(8), 87(9), 137(19), 181(22), 209(100), 307(6), 352(2).

HRMS Calcd for C₁₉H₃₂O₄Si: 352.2070; found: 352.2051.

$R_f$=0.71 (ethyl acetate/hexanes, 1:1).

Preparation of Compound 13

Dichloromethane (anhydrous, 2 mL) and oxalyl chloride (0.35 mL of a 2M solution in dichloromethane, 0.7 mmol, 2.3 eq) were cooled under nitrogen at −60° C. Dimethylsulfoxide (0.15 mL, 2.14 mmol, 7 eq) was then added slowly and after 15 minutes, a solution of the alcohol 11 (85 mg, 0.3 mmol, 1 eq in dichloromethane, 2 mL). After 30 minutes at −60°−−50° C., triethylamine (1 ml, excess) was added, and the mixture was allowed to warm to room temperature. Ether (10 mL) and water (10 mL) were added and the organic phase was washed with 0.1N hydrochloric acid (10 mL). The aqueous layers were combined and extracted with ether (2×10 mL). The combined organic layers were washed with brine (20 mL), dried over magnesium sulfate, filtered and concentrated under reduced pressure. Flash chromatography of the residue (50 mL silica gel, 40–65μ, ethyl acetate/hexanes 1:4) gave the dione 13 (58 mg, 69%) as a yellow oil.

¹H NMR (CDCl₃, 400 MHz): δ6.20 (m, 1H), 6.10 (dq, J=0.7, 0.9 Hz, 1H), 3.95–4.02 (m, 4H), 2.30 (brt, J=6.7 Hz, 2H), 1.94 (dd, J=1.4, 0.9 Hz, 3H), 1.82 (t, J=6.7 Hz, 2H), 1.67 (s, 3H), 1.18 (s, 6H).

¹³C NMR, CDCl₃, δ17.18, 21.40, 22.88, 26.34, 31.67, 42.07, 65.10, 111.17, 131.23, 138.44, 139.54, 139.68, 193.76, 197.76.

IR (neat, thin film, cm⁻¹) 2980.0, 2957.7, 2883.8, 1668.7, 1454.4, 1378.0, 1259.9, 1213.0, 1137.4, 1110.6, 1042.9.

MS 41(88), 43(28), 45(30), 67(32), 69(30), 87(29), 137(50), 181(30), 209(100), 278(18).

HRMS Calcd for C₁₆H₂₂O₄: 278.1518; found: 278.1515.

$R_f$=0.58 (ethyl acetate/hexanes 1:1).

Preparation of adduct 14

In a base washed NMR tube with a screwable teflon joint, a solution of enone 13 (48 mg, 0.172 mmol) and diene (0.69 mmol, 4 eq) in deuterated benzene (0.5 mL) was heated at 80° C. After 3 hours, NMR analysis showed that the reaction was complete. The solvent was evaporated and the residue was treated with 0.1N hydrochloric acid/tetrahydrofuran (2 mL, 1:4 vol) for 30 minutes. The mixture was then poured into a saturated solution of sodium hydrogenocarbonate (20 mL) and extracted with dichloromethane (2×20 mL). The combined organic layers were dried over magnesium sulfate, filtered and evaporated to give enone 14 as a yellow oil (crude 95%) which showed satisfactory purity (NMR).

¹H NMR (CDCl₃, 400 MHz): δ7.27 (dd, J=10.2, 1.2 Hz, 1H), 6.00 (d, J=10.2 Hz, 1H), 3.92–4.02 (m, 4H), 2.60 (m, 1H), 2.46 (m, 2H), 2.25 (m, 2H), 1.97 (dt, J=13.6, 8, 8 Hz, 1H), 1.82 (m, 2H), 1.55 (s, 3H), 1.47 (s, 3H), 1.09 (s, 3H), 1.03 (s, 3H).

¹³C NMR, CDCl₃, δ20.92, 22.25, 23.38, 25.22, 26.34, 30.66, 32.59, 34.38, 42.01, 47.98, 65.06, 65.11, 110.75, 129.32, 135.73, 136.37, 151.04, 196.32, 197.91, 198.14.

IR (neat, thin film, cm⁻¹) 2922.9, 2852.6, 1684.9, 1456.0, 1380.1, 1228.1, 1137.1, 1103.1, 1049.1, 992.3, 825.2.

MS 41(20), 55(25), 67(28), 81(27), 86(23), 87(25), 95(20), 137(40), 181(28), 209(100), 346(18).

HRMS Calcd for C₂₀H₂₆O₅: 346.1780; found: 346.1792.

$R_f$=0.40 (ethyl acetate/hexanes, 1:1).

Preparation of Compound 15

The ketal 14 (56 mg, 0.16 mmol) was treated with p-toluenesulfonic acid (30 mg, 0.16 mmol) at 60° C. for 21 hours in a tetrahydrofuran/water mixture (1:1 vol, 2 mL) and the reaction was monitored by NMR analysis of aliquots. The mixture was then diluted with ether (10 mL) and poured into saturated hydrogenocarbonate (5 mL). The aqueous layer was extracted with ether (10 mL) and the combined organic layers were washed with brine (10 mL), dried over magnesium sulfate, filtered and evaporated. Flash chromatography of the residue (50 mL of silica gel 40–65μ, ethyl acetate/hexanes 1:4) gave 2 fractions, remaining starting ketal (5 mg) and tetraone 15 (35.4 mg, 0.117 mmol, 73.3%, 79.4% based on starting material recovery), as a yellow oil.

¹H NMR (CDCl₃, 400 MHz): δ7.25 (dd, J=10.2, 1.1 Hz, 1H), 6.04 (d, J=10.2 Hz, 1H), 2.58–2.68 (m, 3H), 2.40–2.57 (m, 4H), 2.02 (ddd, J=13.4, 10, 5.7 Hz, 1H), 1.60 (s, 3H), 1.58 (s, 3H), 1.23 (s, 3H), 1.17 (s, 3H).

¹³C NMR, CDCl₃, δ21.47, 24.07, 25.02, 25.18, 31.29, 32.51, 34.34, 34.97, 46.07, 48.02, 129.61, 135.77, 138.37, 150.64, 195.04, 197.90, 198.13, 211.80.

IR (thin film, cm⁻¹) 2971.6, 2930.1, 1680–1720, 1461.8, 1379.4, 1230.8, 1210.1, 1127.0, 1033.7, 874.5, 827.8, 803.6.

MS (CH₄) 165(100), 303(79), 304(20).

HRMS. Calcd for C₁₈H₂₂O₄: 302.1518; Calcd for M+H (C₁₈H₂₃O₄): 303.1596. found: 303.1586.

$R_f$=0.44 (ethyl acetate/hexanes, 1:1).

Preparation of Compound 16

A 25 mL flask was charged with a solution of the alcohol 4 (226 mg, 1 mmol) in dichloromethane (5 ml), triethylamine (anhydrous, 121 mg, 1.2 eq), 4-dimethylaminopyridine (12 mg, 0.1 eq), and the mixture was cooled to 0° C. under nitrogen. A solution of t-butylchlorodimethylsilane (166 mg, 1.1 eq) in dichloromethane (3 mL) was added, and the mixture was stirred for 1 hour at room temperature and was then washed with 5% sodium hydrogenocarbonate (10 mL) and brine (10 mL). The aqueous layers were extracted with dichloromethane (10 mL) and the combined organic layers were dried over magnesium sulfate, filtered, and evaporated. Flash chromatography of the residue (100 mL, silica gel, 40–65μ, 5% ether in hexanes) gave 16 (280 mg, 76% yield) as a clear oil.

¹H NMR (CDCl₃, 400 MHz): δ3.94–4.05 (m, 4H), 3.61 (t, J=8.5 Hz, 2H), 2.33 (t, J=8.5 Hz, 2H), 2.12 (t, J=6.6 Hz, 2H), 1.76 (t, J=6.6 Hz, 2H), 1.69 (s, 3H), 1.08 (s, 6H), 0.93 (s, 9H), 0.09 (s, 6H).

¹³C NMR, CDCl₃, δ−5.21, 18.32, 19.76, 22.60, 25.98, 26.67, 30.55, 32.87, 43.05, 62.74, 64.83, 112.11, 127.80, 132.44.

HRMS Calcd for C$_{19}$H$_{36}$O$_3$Si: 340.2434; found: 340.2447.

MS 73(50), 75(53), 86(50), 165(95), 197(100), 239(27), 283(25), 297(12), 325(10), 340(13).

IR (neat, thin film, cm$^{-1}$) 2952.9, 1253.8, 1079.1, 835.5, 774.4.

R$_f$=0.59 (ethyl acetate/hexanes 1:4).

Preparation of enone 17

Chromium trioxide (275 mg, 2.76 mmol, 20 eq) was suspended in anhydrous dichloromethane (4 mL) and cooled to −23° C. (carbon tetrachloride/solid carbon dioxide bath). After 10 minutes, 3,5-dimethylpyrazole (265 mg, 2.76 mmol, 20 eq) was added in one portion. The suspension then became a red-brown solution. After 20 minutes of stirring at −23° C., a solution of the olefin 16 (47 mg, 0.13 mmol, 1 eq) in dichloromethane (3 mL) was added and the mixture was then stirred one hour between −20° and −10° C. Sodium hydroxide of (6N, 1 mL) was added and the mixture was stirred 30 minutes at 0° C. After dilution with water and dichloromethane, the aqueous phase was re-extracted with dichloromethane (5 mL) and the combined organic layers were washed with 0.1N hydrochloric acid, then brine, and were then dried over magnesium sulfate. Filtration, evaporation, and flash chromatography (60 mL, silica gel, 40–65μ, ethyl acetate/hexanes 1:4) gave 23.3 mg (48%) of enone 17 as a pale yellow oil.

$^1$H NMR (CDCl$_3$, 400 MHz): ∂3.93–4.03 (m, 4H), 3.71 (t, J=8 Hz, 2H), 2.74 (s, 2H), 2.61 (t, J=8 Hz, 2H), 1.85 (s, 3H), 1.24 (s, 6H), 0.92 (s, 9H), 0.09 (s, 6H).

$^{13}$C NMR, CDCl$_3$, ∂−5.29, 11.94, 18.28, 21.72, 25.90, 34.52, 43.93, 45.78, 61.26, 65.23, 111.71, 131.73, 159.03, 196.57.

IR (neat, thin film, cm$^{-1}$) 2928.0, 2881.6, 2856.1, 1673.3, 1611.4, 1471.7, 1335.1, 1252.3, 1130.9, 1073.7, 836.1, 776.5.

MS 43(26), 73(73), 75(70), 89(46), 179(78), 253(49), 268(100), 297(20), 354(4), 355(18).

HRMS Calcd for C$_{19}$H$_{34}$O$_4$Si: 354.2227; found: 354.2225.

R$_f$=0.23 (ethyl acetate/hexanes, 1:4).

Preparation of Compound 18

The enone 17 (5.4 mg, 0.0153 mmol) was stirred in acetone (1 mL) in the presence of p-toluenesulfonic acid (19 mg, 0.1 mmol) and water (50 μl). After 4 hours at room temperature, TLC showed that all the starting material has disappeared. The mixture was then diluted with 2 mL of ether, washed with 2 mL of saturated aqueous solution of sodium hydrogenocarbonate. The organic phase was then washed with 2 mL of brine, dried over magnesium sulfate filtered and evaporated to give alcohol 18 (3 mg, 82%).

$^1$H NMR (CDCl$_3$, 400 MHz): ∂3.92–4.02 (m, 4H), 3.77 (t, J=7.8 Hz, 2H), 2.73 (s, 2H), 2.65 (t, J=7.8 Hz, 2H), 1.85 (s, 3H), 1.24 (s, 6H).

MS (CH$_4$) 87(58), 179(50), 211(20), 223(22), 241(M+1, 100), 269(M+1+28, 24), 281(M+1+40, 11).

HRMS Calcd for C$_{13}$H$_{20}$O$_4$: 240.1362; found: 240.1382.

Preparation of Compound 19

Heating the ketal 4 (44 mg, 0.195 mmol) in 2 mL of a 1:1 (vol) mixture of water and tetrahydrofuran at 45° C. gave, after dilution with ether, washing with saturated sodium hydrogenocarbonate then brine, drying over magnesium sulfate, filtration and evaporation, the pure ketone 19 as a colorless oil. TLC did not allow monitoring of the outcome of the reaction. NMR analysis of aliquots indicated that 2 hours were sufficient for completion of the hydrolysis which was quantitative.

$^1$H NMR (CDCl$_3$, 400 MHz): ∂3.64 (t, J=8.1 Hz, 2H), 2.53 (t, J=7 Hz, 2H), 2.40 (t, J=8.1 Hz, 2H), 2.35 (t, J=7 Hz, 2H), 2.08 (brs, 1H), 1.76 (s, 3H), 1.18 (s, 6H).

$^{13}$C NMR, CDCl$_3$, ∂19.87, 24.54, 31.57, 32.45, 35.93, 47.82, 62.16, 129.70, 132.48, 215.34.

IR (neat, thin film, cm$^{-1}$) 3409.7, 2969.5, 2929.3, 1712.2, 1471.1, 1446.0, 1378.3, 1357.6, 1039.5.

MS 41(45), 55(40), 81(56), 96(42), 107(44), 124(100), 137(18), 149(20), 182(30).

HR Calcd for C$_{11}$H$_{18}$O$_2$: 182.1307; found: 182.1318.

R$_f$=0.43 (ethyl acetate/hexanes 1:1).

Preparation of diol 20

A solution of the diene 3 (214 mg, 1.03 mmol) and N-methylmorpholine-N-oxide (NMO, 127 mg, 1.08 mmol, 1.05 eq) was stirred in an acetone-water mixture (8:1 vol, 5 mL) while bubbling nitrogen through the solution. Then a 0.1M solution of osmium tetroxide in t-butanol (1 mL, 0.1 mmol, 0.097 eq) was added and stirring and nitrogen bubbling was continued 3 hours until TLC (ethyl acetate/hexanes, 1:1 vol) showed total disappearance of the starting diene leading to a much more polar product. The reaction was then quenched with saturated sodium hydrogenosulfite (10 mL) then diluted with ethyl acetate (10 mL) and water (15 mL). The aqueous phase was extracted (4×20 mL ethyl acetate) and the combined organic layers were dried over magnesium sulfate, filtered and evaporated to give quantitatively pure diol 20 which crystallized when refrigerated.

$^1$H NMR (CDCl$_3$, 400 MHz): ∂4.38 (dd, J=10, 3 Hz, 1H), 3.90–4.02 (m, 4H), 3.88 (dd, J=11.7, 10 Hz, 1H), 3.51 (dd, J=11.7, 3 Hz, 1H), 3.45 (brs, 2H), 1.92–2.23 (m, 2H), 1.84 (s, 3H), 1.60–1.80 (m, 2H), 1.18 (s, 3H), 1.02 (s, 3H).

$^{13}$C NMR, CDCl$_3$, ∂20.93, 21.50, 23.26, 26.34, 31.61, 42.78, 64.73, 64.87, 65.60, 72.23, 111.87, 132.17, 135.12.

HRMS Calcd for C$_{13}$H$_{22}$O$_4$: 242.1518; found: 242.1518.

MS 86(100), 87 (62), 107(25), 125(44), 150(18), 167(15), 211(52), 212(38), 242(15).

IR (chloroform, cm$^{-1}$) 3617, 3455.3, 2960.1, 2887.0, 1708.1, 1472.7, 1453.6, 1428.1, 1381.6, 1356.2, 1207.9, 1139.8, 1055.1.

R$_f$=0.26 (ethyl acetate/hexanes, 1:1).

Melting point: 100°–101° C.

Preparation of aldehyde 21

To a stirred solution of diol 20 (51 mg, 0.21 mmol) and N-methylmorpholine-N-oxide (NMO, 27 mg, 0.23 mmol) was added molecular sieves (4 angstroms, powdered) and tetrapropylammonium perruthenate (TPAP, 7.4 mg, 0.1 eq, 0.021 mmol). After 10 minutes, the green color turned to a grey-black color. The mixture was applied to a silica gel column (70 mL, silica gel, 40–65μ, ethyl acetate/hexanes, 1:4) which was eluted with the same solvent to give 24.5 mg (56%) of the aldehyde 21.

$^1$H NMR (CDCl$_3$, 400 MHz): ∂10.08 (s, 1H), 3.99 (brs, 4H), 2.40 (t, J=6.6 Hz, 2H), 2.11 (s, 3H), 1.80 (t, J=6.6 Hz, 2H), 1.26 (s, 6H).

$^{13}$C NMR, CDCl$_3$, ∂18.88, 21.83, 26.17, 33.62, 41.41, 65.67, 111.54, 139.30, 153.88, 192.00.

IR (neat, thin film, cm$^{-1}$) 2883.0, 1725.8, 1673.6, 1614.0, 1463.9, 1379.0, 1266.5, 1210.4, 1144.7, 1096.3, 1050.9.

HRMS Calcd for $C_{12}H_{18}O_3$: 210.1256; found: 210.1253.

MS 49(100), 51(27), 83(20), 86(30), 87(40), 181(3), 182(3), 183(3), 209(3), 210(4), 211(5).

$R_f$=0.70 (ethyl acetate/hexanes, 1:1).

Preparation of Compound 22

To a room temperature solution of ketoketal 1 (9) (3.972 g, 20.06 mmol) in tetrahydrofuran (anhydrous, 50 mL) was added a solution of sodium acetylide in xylene and mineral oil (18% wt, 10.7 mL, d=0.884, 35 mmol, 1.75 eq) and the mixture was stirred for 5 hours under nitrogen. It was then diluted with ether (100 mL), washed with brine (3×100 mL). The aqueous layers were back extracted (3×100 mL of ether) and the combined organic layers were dried over magnesium sulfate, filtered and evaporated. Flash chromatography of the residue (150 mL, silica gel, 40–65μ, ethyl acetate/hexanes, 1:4) gave 3.365 g (74.9%) of white crystals of tertiary alcohol 22.

$^1$H NMR (CDCl$_3$, 400 MHz): ∂3.89–4.03 (m, 4H), 2.40 (s, 1H), 1.93–2.04 (m, 1H), 1.78 (m, 1H), 1.39–1.58 (m, 3H), 1.24 (s, 3H), 1.16 (s, 3H), 1.12 (d, J=8.8 Hz, 3H).

$^{13}$C NMR, CDCl$_3$, ∂16.25, 16.93, 22.15, 26.03, 29.81, 35.78, 45.51, 64.02, 65.48, 72.20, 78.23, 84.73, 112.51.

HRMS Calcd for $C_{13}H_{20}O_3$: 224.1412; found: 224.1409.

MS 53(38), 55(38), 86(20), 99(48), 207(100), 224(16).

IR (chloroform, cm$^{-1}$) 3489.6, 3306.7, 2981.4, 2936.9, 2891.2, 1452.0, 1390.1, 1379.6.

$R_f$=0.38 (ethyl acetate/hexanes, 1:4).

Melting point 107°–108° C. (hexanes).

Preparation of compound 23

Chromium trioxide (1 g, 10 mmol, 20 eq) was suspended in dichloromethane (10 mL) and cooled to −23° C. 3,5-Dimethylpyrazole (DMP, 0.96 g, 20 eq) was then added and the mixture was stirred 20 minutes at −23° C. The enol triflate 2 (165 mg, 0.5 mmol) was dissolved in dichloromethane (2 mL) and the solution was added to the red-brown solution of CrO$_3$-DMP complex. After being stirred at room temperature, a pale new spot appeared on the TCL, but the mixture was mostly composed of the remaining triflate 2. No further disappearance of starting material was observed even after 2 days of reflux. The mixture was then cooled to room temperature; 3 mL of 6N sodium hydroxide was added and the mixture was stirred at 0° C. for 30 minutes. After dilution with water (20 mL) and dichloromethane (20 mL), the aqueous phase was extracted with dichloromethane (20 mL), and the combined organic layers were washed with 0.1N hydrochloric acid (2×20 mL), brine (20 mL), dried over magnesium sulfate, filtered and concentrated in vacuo. Flash chromatography (60 mL, silica gel, 40–65μ, ethyl acetate/hexanes, 1:5) gave 2 fractions, starting triflate (79 mg, 48%) and a fraction constituted with 2 products (62 mg, 36%) having one of them being the desired enone 23 constituting half of the fraction.

$^1$H NMR (CDCl$_3$, 400 MHz): ∂3.95–4.04 (m, 4H), 2.81 (s, 2H), 1.91 (s, 3H), 1.33 (s, 6H).

HRMS Calcd for $C_{12}H_{15}O_6F_3$: 344.0541; found: 344.0512.

$R_f$=0.34 (ethyl acetate/hexanes, 1:4).

Preparation of enyne 24

A solution of the triflate 2 (180 mg, 0.546 mmol), ethynyltributylstannane (1.092 mmol, 344 mg, 0.316 mL, 2 eq), lithium chloride (anhydrous, 69 mg, 1.63 mmol, 3 eq) and tetrakis(triphenylphosphine) palladium(O), (Pd(PPh$_3$)$_4$, 63 mg, 0.1 eq) in anhydrous THF (3 mL) was refluxed 1 day. After being cooled to room temperature, the mixture was diluted with ethyl acetate (30 mL) and washed with brine (2×50 mL). The aqueous layer was extracted with ethyl acetate (2×30 mL) and the combined organic layers were dried over magnesium sulfate, filtered and evaporated. Flash chromatography of the residue (100 ml, silica gel, 40–65μ, 5% ether in hexanes) gave the enyne 24 as a pale yellow oil (77 mg, 69%).

$^1$H NMR (CDCl$_3$, 400 MHz): ∂3.97 (brs, 4H), 3.03 (s, 1H), 2.23 (t, J=6.6 Hz, 2H), 1.90 (s, 3H), 1.76 (t, J=6.6 Hz, 2H), 1.16 (s, 6H).

$^{13}$C NMR, CDCl$_3$, ∂22.00, 23.19, 26.62, 30.35, 41.69, 64.98, 80.20, 81.76, 111.17, 125.60, 141.15.

HRMS Calcd for $C_{13}H_{18}O_2$: 206.1307; found: 206.1325.

MS 41(50), 42(50), 43(55), 49(76), 51(48), 86(100), 87(25), 105(29), 119(24), 134(26), 163(12), 206(24).

IR (neat, thin film, cm$^{-1}$) 3302.9, 2978.4, 1466.9, 1380.8, 1356.5, 1212.0, 1143.8, 1085.8, 1057.6, 992.0, 949.0, 907.2.

$R_f$=0.59 (ethyl acetate/hexanes, 1:4).

General procedure for Nozaki-Kishi couplings. Preparation of allylic alcohols 25, 26, 27 and 29 and enones 28 and 30

To a 1M solution of anhydrous chromium chloride (4–6 eq.) containing 0.1% (wt) of nickel chloride in anhydrous dimethylformamide, was added a 1M solution of either aldehyde 5 or benzaldehyde (1 eq.) and the iodoolefin (2–3 eq.) in anhydrous dimethylformamide. Reactions involving E-iodocrotonitrile had to be heated at 80° C. while methyl E-iodocrotonate reacted at room temperature. After 12 to 16 hours, water was added and the mixture was extracted with ether. After washings with water and brine, drying over magnesium sulfate and evaporation of the solvent, flash chromatography (ethyl acetate/hexanes, 1:2) gave allylic alcohols 25 (25), 26, 27 and 29 in 59 to 66% yield.

Regular Swern oxidation (oxalyl chloride, dimethylsulfoxide, triethylamine, dichloromethane) of allylic alcohols 27 and 29 gave enones 28 and 30 respectively in 82% and 88% yield after flash chromatography (ethyl acetate/hexanes, 1:4).

Data for allylic alcohol 25 (25)

$^1$H NMR, 400 MHz, CDCl$_3$, TMS, ∂1.86 (s, 3H), 5.12 (s, 1H), 5.81 (brs, 1H), 7.27–7.40 (m, 5H).

$^{13}$C NMR, CDCl$_3$, ∂17.92, 76.97, 94.87, 117.03, 126.88, 128.89, 128.97, 139.76, 164.01.

IR (neat, thin film) 3443.3, 3064.2, 3030.5, 2920.8, 2856.1, 2220.7, 1633.3, 1493.9, 1061.4, 1019.4.

MS 51(40), 68(53), 77(86), 79(61), 105(59), 107(42), 130(36), 144(22), 158(26), 172(30), 173(100).

HRMS Cacd. for $C_{11}H_{11}ON$: 173.0841; found: 173.0838.

$R_f$=0.5 (ethyl acetate/hexanes, 1:1).

Data for allylic alcohol 26

$^1$H NMR, 400 MHz, CDCl$_3$, TMS, ∂1.97 (d, J=1.1 Hz, 3H), 3.71 (s, 3H), 5.11 (s, 1H), 6.26 (rs, 1H), 7.31-7.35 (m, 5H).

$^{13}$C NMR, CDCl$_3$, ∂15.52, 51.05, 78.38, 114.63, 126.89, 128.30, 128.67, 140.63, 158.75, 167.30.

IR (neat, thin film) 3463.9, 3028.4, 2949.6, 1718.9, 1653.9, 1493.3, 1435.6, 1219.6, 1150.2.

MS 69(15) 85(16), 101(100), 129(20), 145(21), 188(15), 206(10).

HRMS Cacd. for C$_{12}$H$_{14}$O$_3$: 206.0943; found: 206.0941.

R$_f$=0.53 (ethyl acetate/hexanes, 1:1).

Data for allylic alcohol 27

$^1$H NMR (CDCl$_3$, 400 MHz): ∂5.60 (brs, 1H), 4.28 (dd, J=10.2, 4.1 Hz, 1H), 3.91-4.01 (m, 4H), 2.11-2.47 (m, 5H), 2.08 (d, J=0.8 Hz, 3H), 1.72-1.86 (m, 2H), 1.68 (s, 3H), 1.10 (s, 3H), 1.08 (s, 3H).

13C NMR, CDCl$_3$,∂17.63, 20.68, 22.57, 23.94, 26.55, 30.83, 34.83, 43.22, 64.99, 65.04, 72.78, 93.92, 112.13, 117.29, 130.95, 132.84, 165.58.

IR (neat, thin film) 3461.6, 2956.5, 2884.1, 2218.0, 1632.9, 1475.9, 1442.8, 1381.2, 1356.3, 1210.2, 1134.1, 1088.3, 1058.0.

MS 86(100), 109(40), 168(22), 196(60), 276(6), 291(8).

HRMS Cacd. for C$_{17}$H$_{25}$O$_3$N: 291.1835; found: 291.1812.

R$_f$=0.54 (ethyl acetate/hexanes, 1:1).

Data for allylic alcohol 29

$^1$H NMR (CDCl$_3$, 400 MHz): ∂6.04 (brs, 1H), 4.25 (dd, J=9.9, 4.6 Hz, 1H), 3.93-4.01 (m, 4H), 3.71 (s, 3H), 2.11-2.47 (m, 5H), 2.19 (s, 3H), 1.73-1.86 (m, 2H), 1.71 (s, 3H), 1.11 (s, 3H), 1.10 (s, 3H).

13C NMR, CDCl$_3$, ∂15.20, 20.71, 22.82, 23.82, 26.64, 30.91, 35.14, 43.28, 50.92, 65.00, 65.04, 74.75, 112.23, 113.58, 131.59, 132.10, 160.68, 167.49.

IR (neat, thin film) 3455.9, 2951.0, 1717.7, 1650.1, 1434.2, 1380.5. 1355.0, 1218.4, 1147.3, 1087.8, 1057.5.

MS 86(87), 87(86), 109(58), 134(41), 168(61), 196(100), 293(28), 324(17).

HRMS Cacd. for C$_{18}$H$_{28}$O$_5$: 324.1937; found: 324.1929.

R$_f$=0.56 (ethyl acetate/hexanes, 1:1).

Data for enone 28

$^1$H NMR (CDCl$_3$, 400 MHz): ∂6.17 (q, J=1.1 Hz, 1H), 3.92-4.01 (m, 4H), 3.42 (s, 2H), 2.25 (d, J=1.1 Hz, 3H), 2.21 (t, J=6.7 Hz, 2H), 1.79 (t, J=6.7 Hz, 2H), 1.48 (s, 3H), 0.95 (s, 6H).

13C NMR, CDCl$_3$, ∂16.90, 20.16, 22.55, 26.64, 30.54, 38.23, 42.88, 64.95, 105.4, 111.74, 115.60, 128.77, 130.92, 156.41, 196.39.

IR (neat, thin film) 2964.0, 2884.2, 2220.4, 1694.3, 1609.6, 1471.8, 1359.5, 1209.9, 1143.0, 1130.8, 1088.4, 1080.4.

MS 66(48), 86(100), 87(83), 94(58), 99(90). 109(93), 190(67), 203(22), 246(21), 289(100).

HRMS Calcd. for C$_{17}$H$_{23}$O$_3$N: 289.1678; found: 289.4692.

R$_f$=0.72 (ethyl acetate/hexanes, 1:1).

Data for enone 30

$^1$H NMR (CDCl$_3$, 400 MHz): ∂6.58 (q, J=1.4 Hz, 1H), 3.94-4.04 (m, 4H), 3.80 (s, 3H), 3.46 (s, 2H), 2.27 (d, J=1.4 Hz, 3H), 2.21 (t, J=6.6 Hz, 2H), 1.79 (t, J=6.6 Hz, 2H), 1.48 (s, 3H), 0.95 (s, 6H).

$^{13}$C NMR, CDCl$_3$, ∂13.88, 20.14, 22.54, 26.72, 30.55, 38.07, 42.93, 51.74, 64.94, 111.92, 123.81, 129.39, 130.77, 151.60, 166.67, 199.51.

IR (neat, thin film) 2951.5, 2883.0, 1726.5, 1692.5, 1639.9, 1435.1, 1356.1, 1216.0, 1087.9, 1060.0.

MS 86(100), 87(40), 99(43), 109(40), 127(42), 223(42), 236(20), 279(12), 322(30).

HRMS Calc. for C$_{18}$H$_{26}$O$_5$: 322.1780; found: 322.1779. R$_f$=0.82 (ethyl acetate/hexanes, 1:1).

Discussion

A retrosynthetic analysis of taxol I total synthesis given in FIG. 1 involves the following key steps:

1. Formation of the B-ring is achieved through an intramolecular ketyl radical cyclization of II. This cyclization might be assisted by cyclic reductive protection of the α-dione (C$_9$-C$_{10}$, numbering refers to taxol structure), deprotection of which would lead to the hydroxy ketone functionality needed in the target.
2. Construction of the D-ring involves an intramolecular oxetane formation via the triol (11, 12) which can be obtained from III through an elimination—reduction process.
3. Formation of the C-ring is achieved by the Diels-Alder reaction between dienophile IV and diene V. The regioselectivity of the cycloaddition is controlled by the carbonyl group at C$_9$ on the dienophile and both oxygenated functions of the diene.
4. Dienophile IV is obtained via Nozaki-Kishi (13, 14) coupling of iodoolefin VII and aldehyde VI followed by oxidation.
5. Preparation of aldehyde VI involves palladium (O) catalyzed coupling (15) of vinyltributylstannane and triflate VIII prepared from the known ketotetal IX (16).

In the context of this general scheme, the following steps are set forth in FIGS. 2–5:

1. A-ring synthesis and extension to the aldehyde 5 (cf. FIG. 2).
2. Preparation of the dienophile 7, Diels-Alder reaction with model four-carbon diene 1-methoxy-3-trimethylsilyloxy-1,3-butadiene (Danishefsky's diene), and Michael addition of a cyano fragment onto the enone function of the adduct (cf. FIG. 2).
3. Further oxidation of dienophile 7 leading to dione 13 and Diels-Alder reaction with model four-carbon diene (cf. FIG. 3).
4. Allylic oxidation of A-ring (preparation of compounds 17 and 23, cf. FIG. 4).
5. Deketalization of A-ring (preparation of compound 19, cf. FIG. 4).
6. Preparation of aldehyde 21 and acetylenic compounds 22 and 24 which may be valuable intermediates in other synthetic schemes toward taxol (cf. FIG. 4).
7. Extension of aldehyde 5 to the trisubstituted dienophiles 28 and 30 (cf. FIG. 5).

Results

Figure 6:
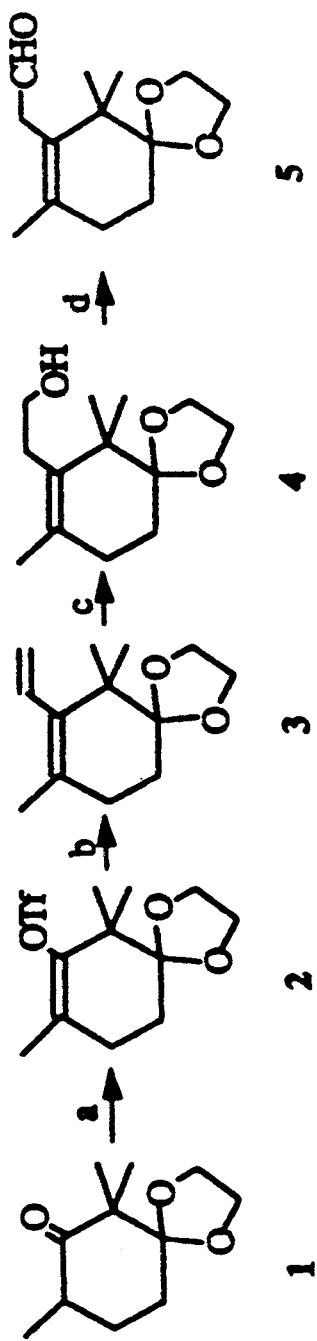
FIG. 6. Preparation of aldehyde 5. (a) KHMDS, PhNTf$_2$, THF, 82%; (b) Bu$_3$SnCH=CH$_2$, cat. Pd(PPh$_3$)$_4$, THF, 91%; (c) 9-BBN, THF, 94%; (d) Swern, 94%.

The first important intermediate is the aldehyde 5 (cf. FIG. 6) which contains all the functionalities needed in the A-ring except the oxygen atom at C-13 which can be introduced later through an allylic oxidation process (vide infra). Treatment of the known ketoketal 1 (16) with potassium bis(trimethylsilyl)amide and N-phenyl trifluoromethanesulfonimide gave the enol triflate 2

(82%) which reacted with vinyltributylstannane under palladium (O) catalysis (15) leading to the diene 3 in 91% yield. Hydroboration of diene 3 (9-borabicyclo[3.3.1]nonane, 94%) gave alcohol 4 which was oxidized (Swern, 94%) to the aldehyde 5. TPAP oxidation (17) of 4 gave 5 in only 71% yield.

Figure 7:
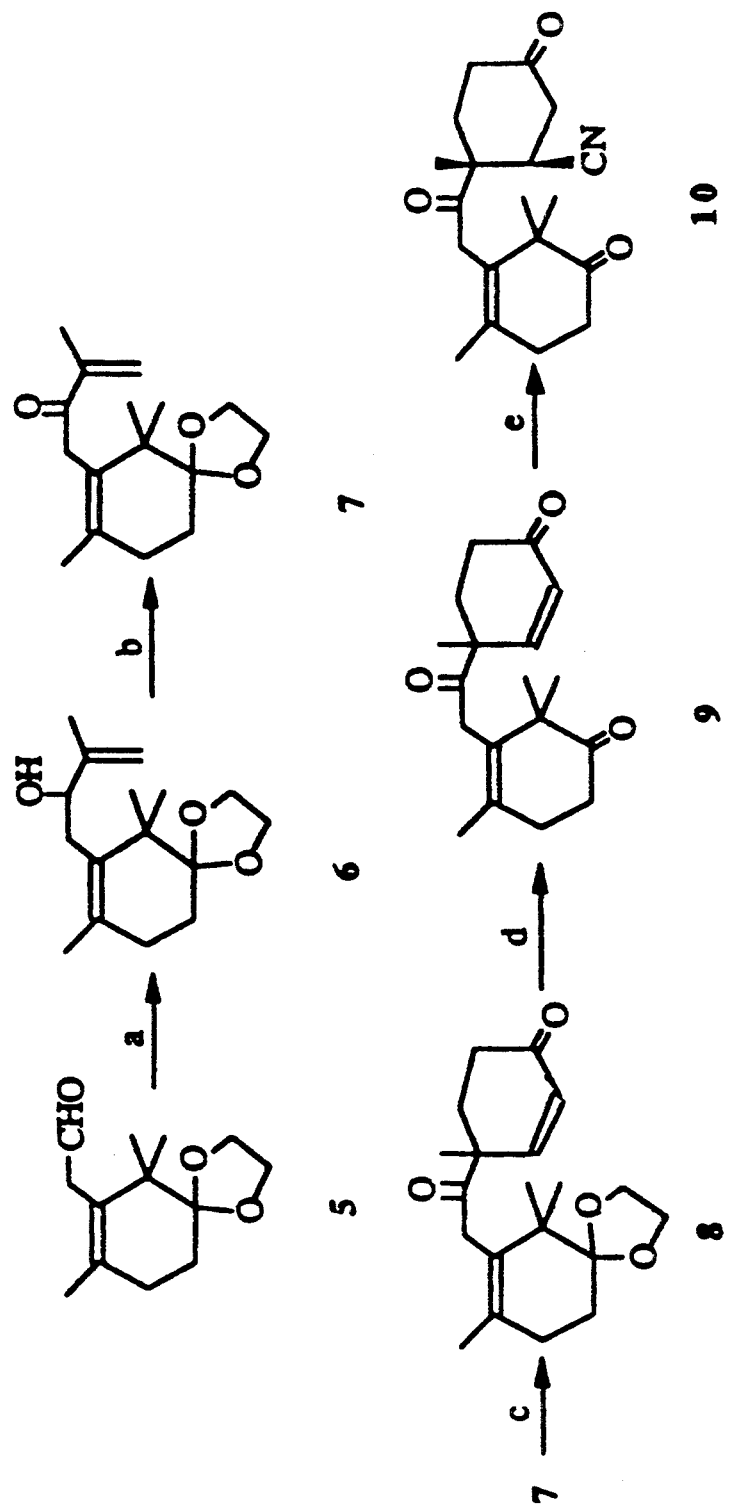
FIG. 7. Preparation of compounds 7 and 10. (a) BrMgC(Me)=CH$_2$, THF, 89%; (b) Swern, 96%; (c) Danishefsky's diene, then H$^+$, 81%; (d) p-TsOH, THF-water, 89%; (e) Et$_2$AlCN, benzene, 72%.

In order to study the Diels-Alder reaction for the construction of the C-ring, aldehyde 5 was extended to the disubstituted dienophile 7 (cf. FIG. 7). Grignard derivative of 2-bromopropene addition onto aldehyde 5 gave the allylic alcohol 6 (89%). Addition of either the lithio or the cerio derivative gave 6 in low yields. Swern oxidation of the alcohol 6 gave the enone 7 in 96% yield.

Cycloaddition of 7 with 1-methoxy-3-trimethylsilyloxy-1,3-butadiene (Danishefky's diene) (18) in benzene (2.5 days, 125° C.) gave after acidic work-up the enone 8 (81%) which was deketalized (p-toluenesulfonic acid, tetrahydrofuran, water, 89%) to the ene trione 9. Hydrocyanation of the enone functionality of 9 with diethylaluminium cyanide (19) gave, besides a small amount of starting material, the desired cis cyanoketone 10 and its trans isomer in a 3:1 ratio in a 96% overall yield. Compound 10 contains 19 out of the 20 carbon atoms of the target. Trapping of the enolate during the Michael addition of the cyanide anion by a carbon electrophile might be an alternative to the use of a five-carbon diene for the introduction of the carbon atom at position 20.

Introduction of the oxygen atom at C-10 was tried starting from diene 3 after bis-hydroxylation to diol 20 (vide infra) without success. Attempted selective oxidation under regular or modified Swern conditions (oxalyl chloride or trifluoroacetic anhydride, addition of triethylamine at various temperatures) (20, 21) gave the undesired hydroxy ketone. This lead us to study the oxidation of the enone 7.

Figure 8:
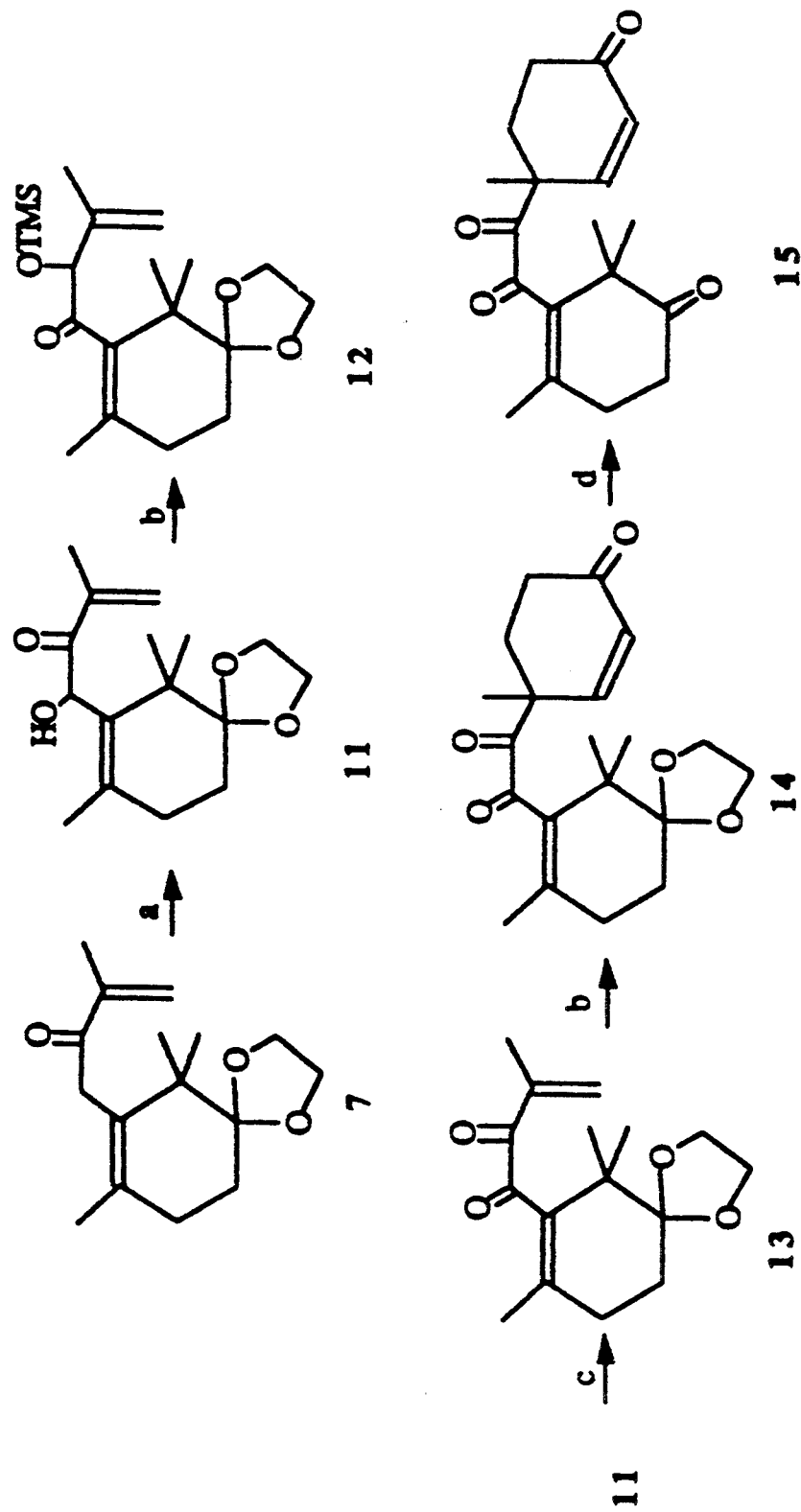
FIG. 8. Preparation of compounds 12 and 15. (a) KHMDS, F. Davis oxaziridine, 87%; (b) Danishefsky's diene, then H$^+$, 95%; (c) Swern, 69%; (d) H$^+$, p-TsOH, THF-water, 79%.

Treatment of the enone 7 with potassium bis(trimethylsilyl)amide and N-(phenylsulfonyl) phenyloxaziridine (22, 23) gave the hydroxy ketone 11 (87%) which did not cyclize (cf. FIG. 8) with 1-methoxy-3-trimethylsilyloxy-1,3-butadiene (Danishefky's diene) (18) but lead to the transposed silylated hydroxy ketone 12 (80%). Further oxidation of the hydroxy ketone 11 (Swern, 69%) gave the α-dione 13 which showed a much higher reactivity toward the same diene as above, giving in only 3 hrs at 80° C. and after acidic work-up the adduct 14 in 95% yield. Deketalization of trione 14 gave the tetraone 15 (p-toluenesulfonic acid, tetrahydrofuran, water, 79%).

Figure 9:
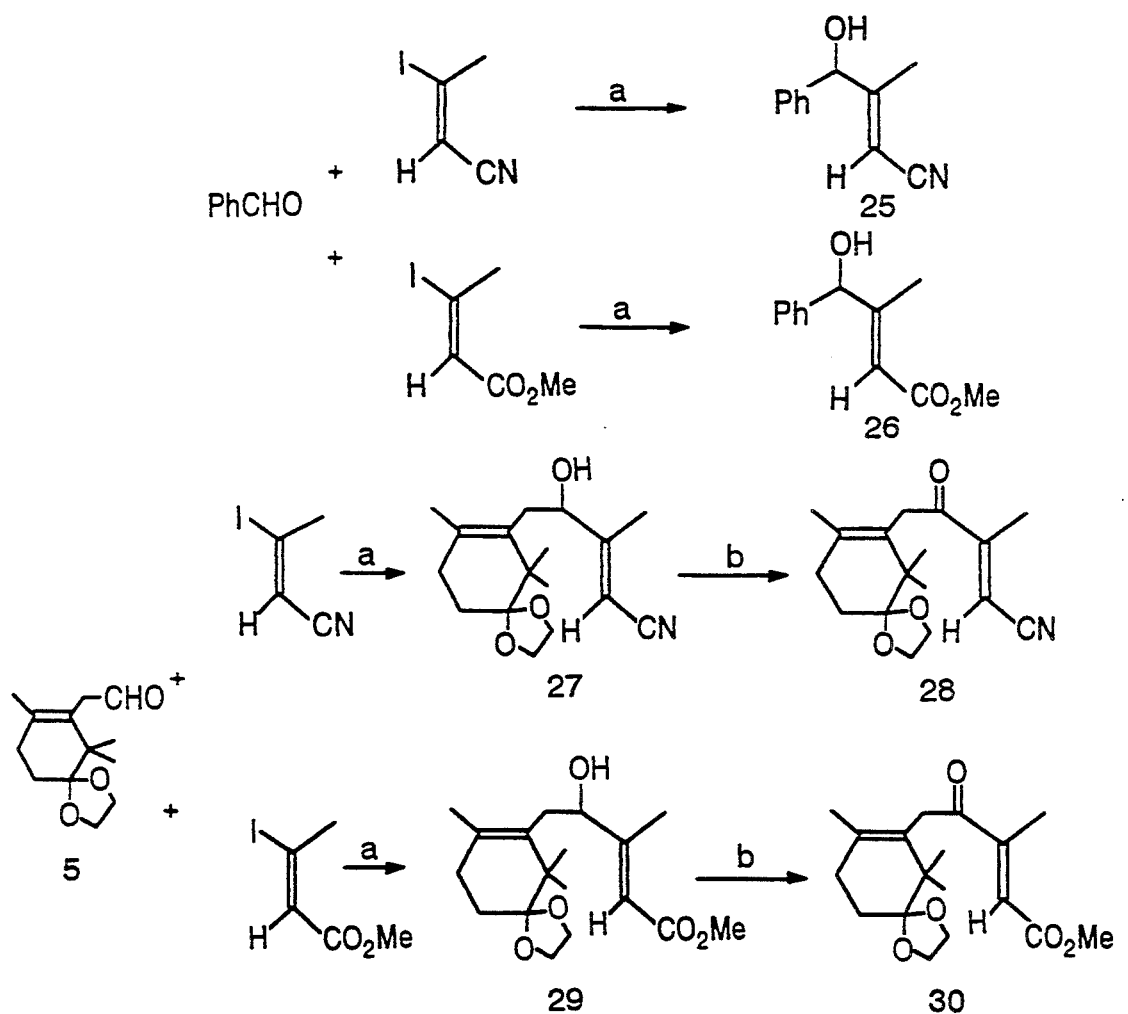
FIG. 9. Preparation of compounds 25, 26, 28, and 30. (a) CrCl$_2$, cat. NiCl$_2$, DMF, 60–70%; (b) Swern, 82–88%.

Unfortunately, the α-dione functionality did not survive an attempted hydrocyanation of compound 15. Protection of the hydroxy ketone 11 with t-butyldimethylsilyl group gave a dienophile which showed a much lower reactivity than the simple enone 7. Thus, we studied the extension of the aldehyde 5 to trisubstituted dienophiles. Since the Nozaki-Kishi coupling (13, 14) of iodocrotonitrile or iodocrotonate had never been described, a preliminary study of this chromium chloride promoted reaction catalyzed by nickel chloride was done with benzaldehyde (cf. FIG. 9), giving allylic alcohols 25 and 26 is about 70% yield. This coupling is a new route for the preparation of Y-hydroxy-α,β-unsaturated esters and nitriles (24, 25). Allylic alcohols 27 and 29 were obtained in comparable yield from aldehyde 5. These compounds were then oxidized to the enones 28 and 30 respectively in 82% and 88% yield. We are currently studying the behavior of these enones in Diels-Alder reactions as well as the further oxidation to the corresponding diones.

Figure 10:
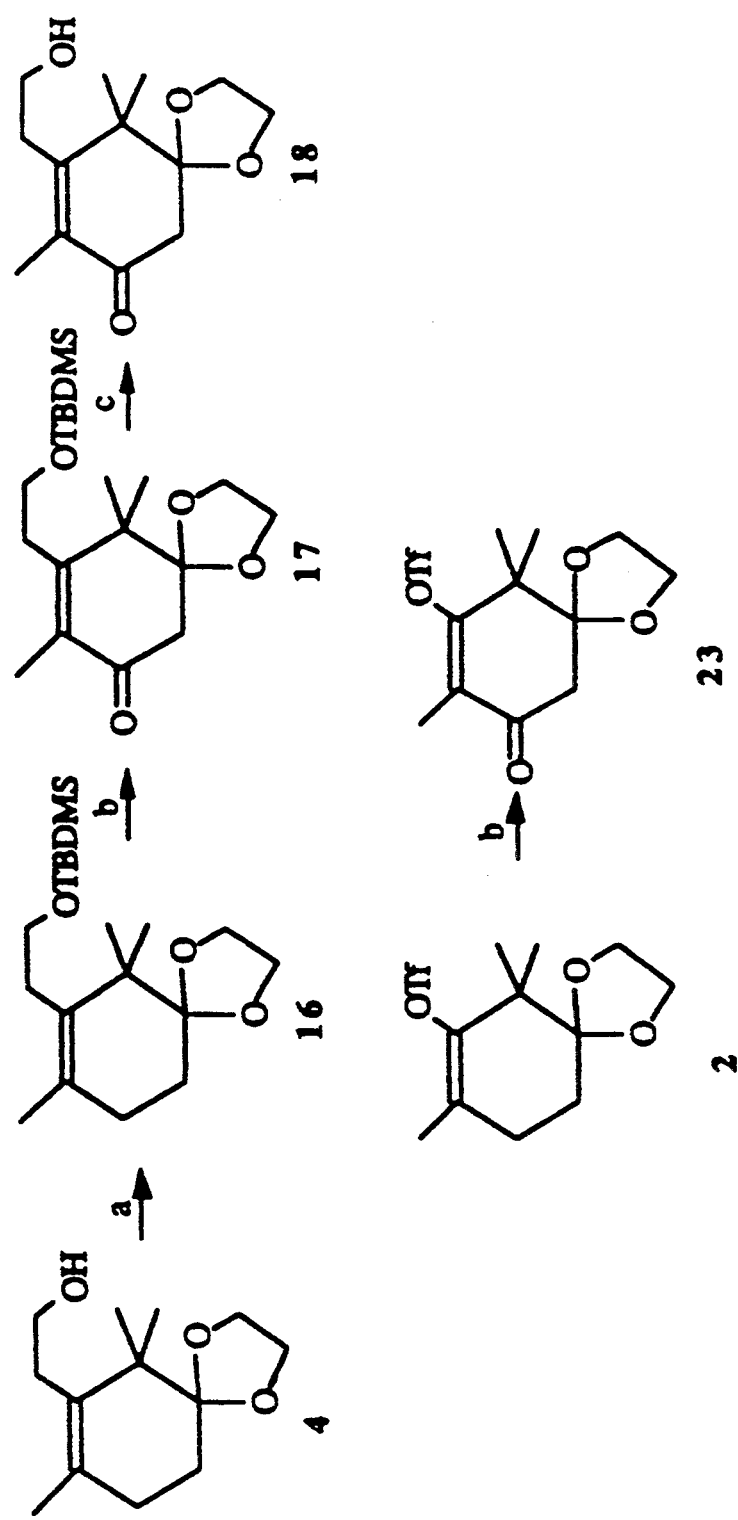
FIG. 10. Preparation of compounds 18 and 23. (a) TBDMSCl, NEt$_3$, CH$_2$Cl$_2$, 76%; (b) CrO$_3$-3,5-DMP, CH$_2$Cl$_2$, 37–48%; (c) p-TsOH, Me$_2$CO, water, 82%.

Besides the straightforward route to taxol skeleton described to this point, various functionalizations in which the most important is the allylic oxidation of the A-ring have been achieved. The presence of the side chain at position 13 is known to be indispensable for any biological activity. A model reaction has been studied on the protected alcohol Alcohol 4 was silylated (t-butylchlorodimethylsilane, triethylamine, 76%) to compound 16 which was oxidized to the enone 17 (48%) by action of the complex formed with chromium trioxide and 3,5-dimethylpyrazole (10, 26). Desilylation of the enone 17 (p-toluenesulfonic acid, acetone, water, 82%) gave the hydroxy enone 18. The same conditions as above for the allylic oxidation of 16 were applied to the enol triflate 2 which gave compound 23 in 37% yield (cf. FIG. 10).

Figure 11:
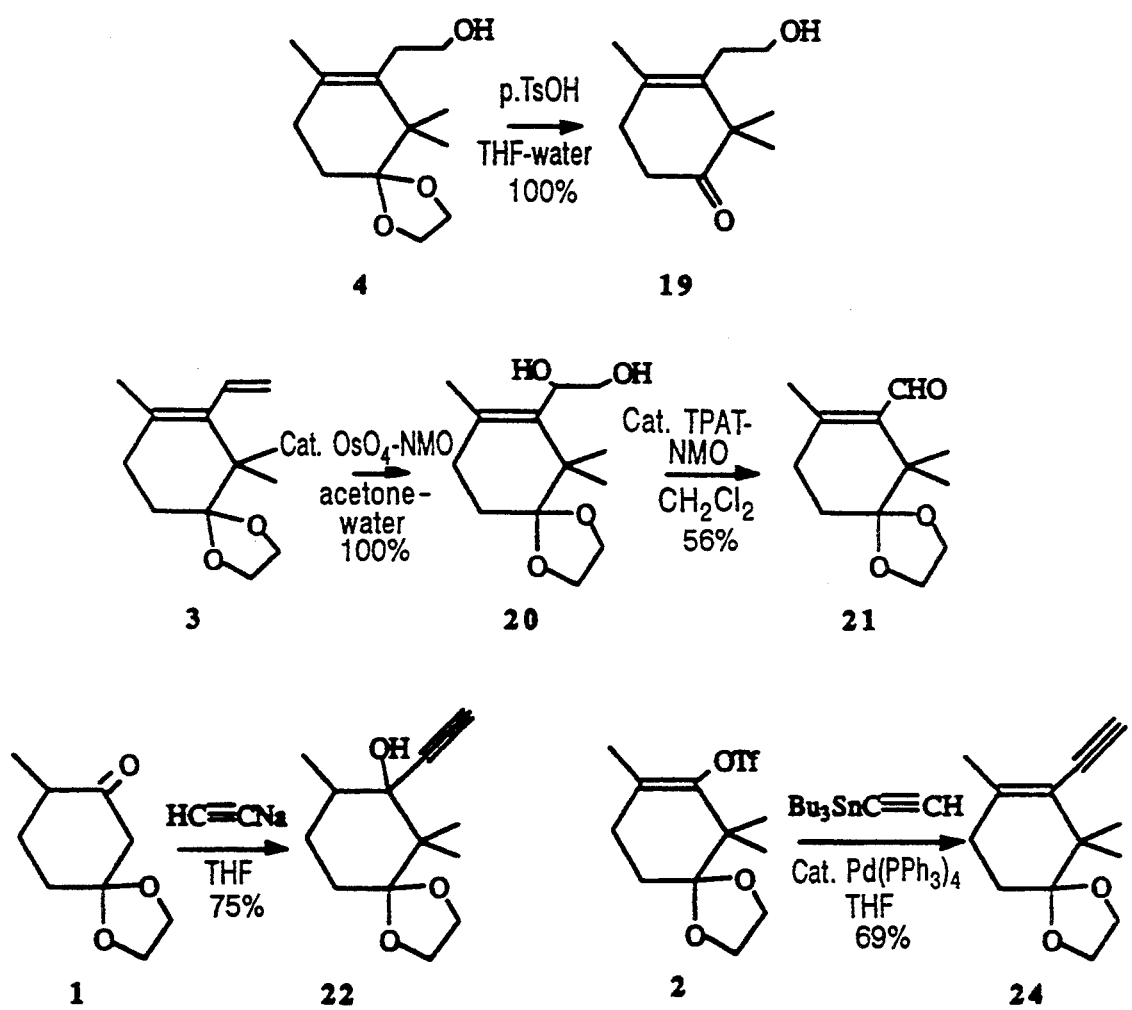
FIG. 11. Preparation of compounds 19, 21, 22, and 24.
Figure 12A:
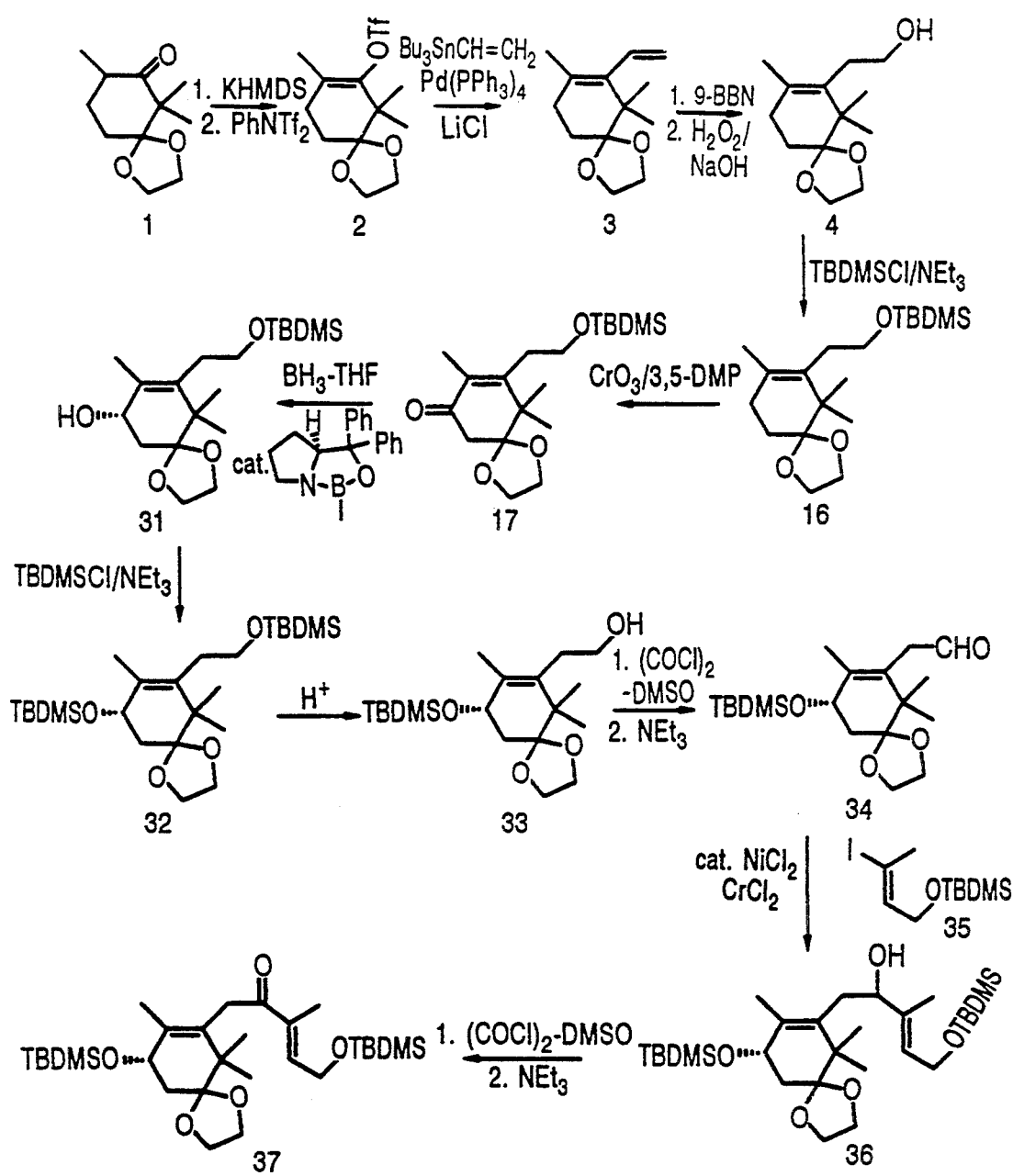
FIG. 12A–12D. Total synthesis of Taxol.
Figure 12B:
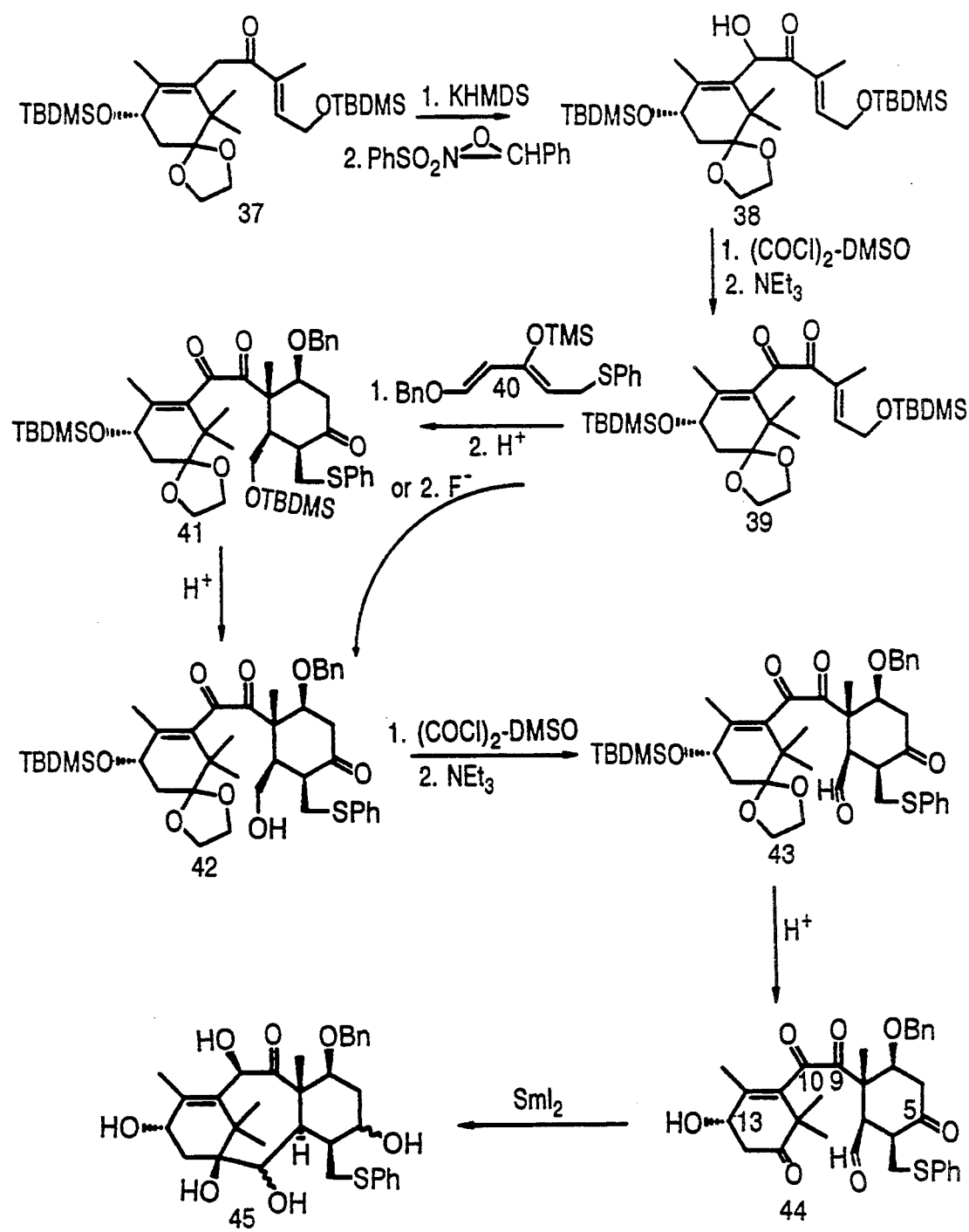
Figure 12C:
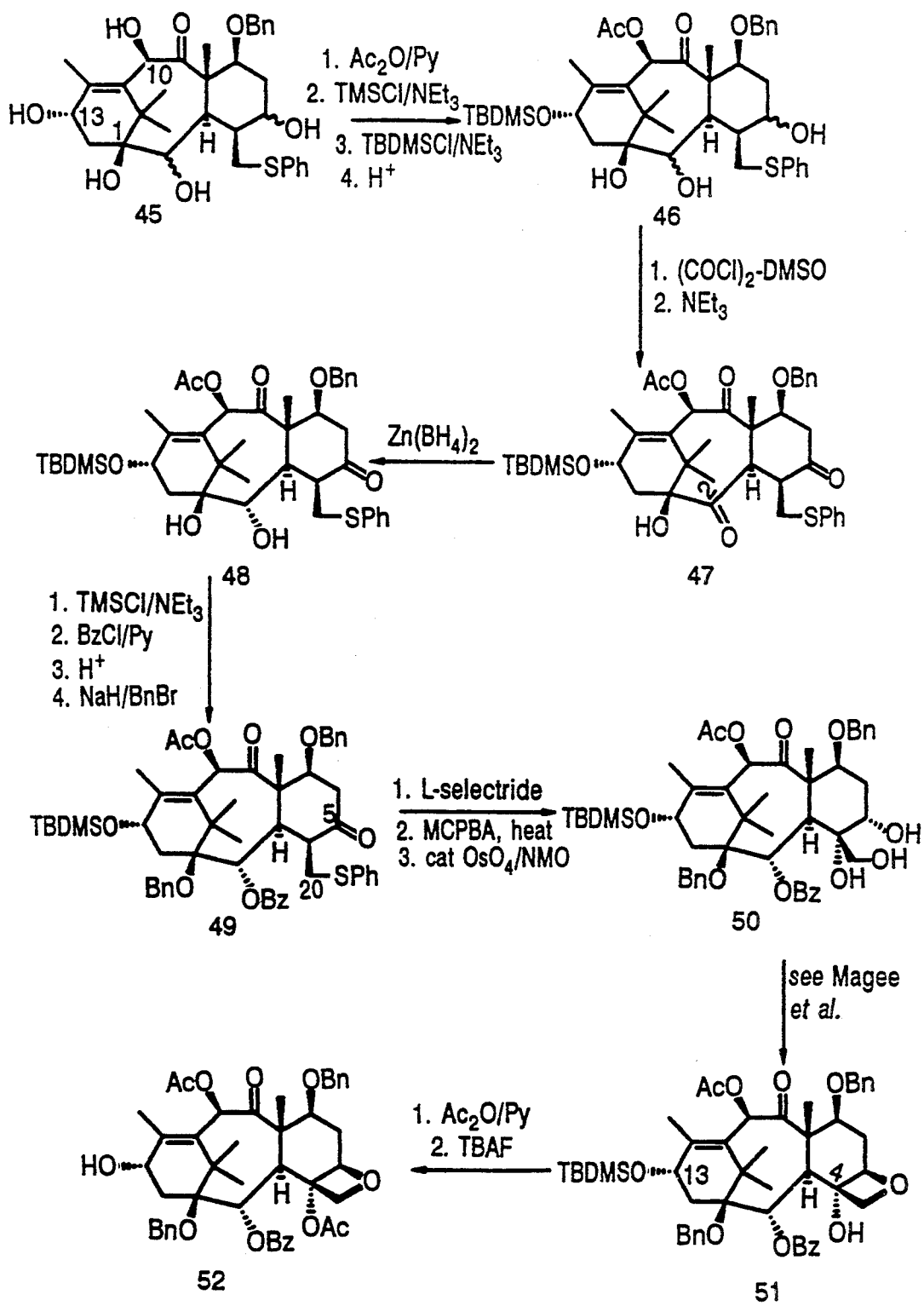
Figure 12D:
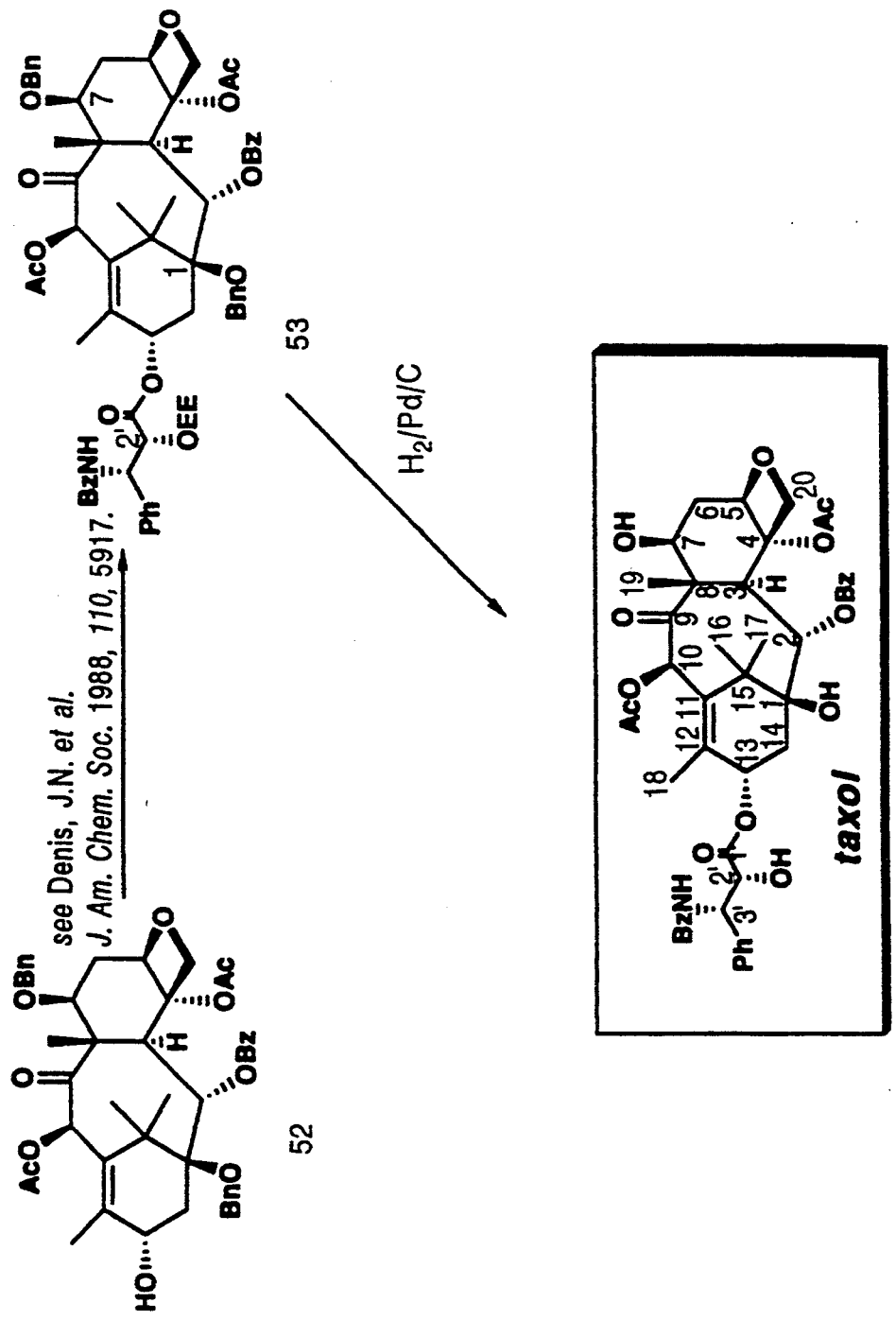

The ketal on A-ring showing fairly strong resistance to weak acids, a model reaction for the deketalization was studied on alcohol 4 which upon treatment with p-toluenesulfonic acid (tetrahydrofuran, water) gave the hydroxy ketone 19 in quantitative yield (cf. FIG. 11).

In order to obtain intermediates similar to aldehyde 5 but containing an extra oxygen atom at C-10, bis-hydroxylation of the diene 3 (catalytic osmium tetroxide, N-methyl morpholine N-oxide, 98%) gave diol 20. Attempted selective oxidation of this diol was unsuccessful either under Swern conditions (vide supra) either upon treatment with catalytic tetrapropylammonium perruthenate (17) and N-methyl morpholine N-oxide. In the later case, cleavage of the diol was observed giving aldehyde 21 in 56% yield (cf. FIG. 11).

Finally, in order to study how various acetylenic intermediates could be linked to an preformed A-ring, the two following reactions were achieved. Addition of sodium acetylide to the ketoketal 1 gave the tertiary alcohol 22 in 75% yield. Eneyne 24 was obtained in 69% yield from the enol triflate 2 via palladium (O) catalyzed coupling with ethynyltributylstannane (15).

Total Synthesis of Taxol as Depicted in FIG. 12

Summary: The strategy of the total synthesis of taxol depicted in FIG. 12 is based on the following key steps or sequences.

1. Extension of the ketoketal 1 to the aldehyde 34 correctly oxidized at C-13, and further extension to the α-diketo dienophile 39.
2. Diels-Alder between 39 and diene 40.
3. Intramolecular pinacolic coupling of 44 giving 45, containing the ABC subskeleton of taxol.
4. Elaboration of the triol 50 and its conversion to the hydroxy oxetane 51 (11,12).

Potassium enolate of ketoketal 1 was treated with N-Phenyl trifluoromethane sulfonimide to give the enol triflate 2 which was coupled under palladium (O) catalysis with vinyl-tri-n-butylstannane leading to diene 3. Hydroboration of 3 with 9-BBN gives after basic hydroperoxide work-up the alcohol 4 which upon treatment with TBDMSCl is converted to the protected alcohol 16. Chromium trioxide complex with 3,5-dimethylpyrazole mediated allylic oxidation of 16 gives enone 17 which is reduced with borane in the presence of a catalytic amount of chiral oxazoborolidine to give the allylic alcohol 31. Protection of the alcohol function of 31 with a TBDMS group followed by selective desilyation of the primary hydroxyl gives alcohol 33 which is oxidized to the aldehyde 34. Nickel chloride catalyzed chromium chloride promoted coupling of vinyl iodide 35 with aldehyde 34 affords the allylic alcohol 36 which is oxidized to the enone 37 and further oxidized to the diketo dienophile 39. Diels-Alder cycloaddition of 39 with diene 40 followed by acidic work-up yields adduct 41 in which the primary silyl ether is selectively cleaved affording alcohol 42. Alternatively, fluoride mediated work-up of the Diels-Alder reaction between 39 and 40 produces 42 directly. Oxidation of 42 to the aldehyde 43 followed by deketalizaton affords 44 in which the TBDMS ether is concomitantly removed. Samarium diiodide promoted intramolecular coupling is assisted by both the presence of the free hydroxyl group at C-13 (numbering refers to the taxol skeleton) and the cyclic enediolate samarium species formed by complexation of the diketo system at C-9,10 with excess reagent. Concomitantly, the ketone at C-5 is also reduced leading to 45. Sequential selective protection of the hydroxyl groups of 45 at C-10, C-1 (temporary) and C-13, leads to triol 46 which upon oxidation produces 47. Stereoselective α-hydroxy directed reduction of the ketone at C-2 of 47 leads to 48 which is sequentially protected to give 49. Reduction at C-5, oxidation of the sulfide at C-20 to the sulfoxide and its elimination upon heating, followed by the osmium tetroxide catalyzed bis-hydroxylation of the intermediate allylic alcohol produces the triol 50. Accordingly to the known procedures (11,12), 50 is converted to the hydroxy oxetane 51 in which the free hydroxyl group at C-13 is released after acetylation of the tertiary alcohol at C-4 and desilylation. Side chain attachment according to known protocols followed by sequential selective deprotection of hydroxyl groups at C-1 and C-7 produces taxol.

Route 2 Synthesis

Synthesis of Compound 55

The alcohol 54 (33) (13.0 g, 58.0 mmol) was dissolved in anhydrous $CH_2Cl_2$ (80 mL) and the resulting solution cooled to 0° C., whereupon 2,6-lutidine (19.0 mL, 17.5 g, 163 mmol) was added followed by dropwise addition of tert-butyldimethylsilyl trifluoromethanesulfonate (17.0 mL, 19.6 g, 74.0 mmol). The solution was maintained at 0° C. for 30 minutes before addition of $H_2O$ (100 mL), and the mixture allowed to come to room temperature. The layers were separated and the aqueous phase repeatedly extracted with $CH_2Cl_2$ (3×75 mL). The combined organic phases were washed with 10% $CuSO_4$ (aq), then dried over $MgSO_4$ and the solvent removed in vacuo. The resulting oil was chromatographed (5% $Et_2O$ in hexanes) to yield 55 (19 g, 56 mmol, 97%).

TLC (20% EtOAc in hexanes): RF=0.55.

HRMS m/z (M+) for $C_{19}H_{34}O_3Si$ calcd. 338.2275, found 338.2282.

IR (film): 1665(w), 1251(s), 1106(s), 1090(s), 1071(s), 812(m), 801(m) cm$^{-1}$.

$^1$H NMR (CDCl$_3$, 400 MHz): ∂5.27 (brs, 1H), 3.99–3.88 (m, 4H), 3.55 (dd, J=11.9, 3.7 Hz, 1H), 2.49 (dq, J=14.0, 3.1 Hz, 1H), 2.14 (dd, J=14.0, 2.9 Hz, 1H), 2.20–2.10 (m, 1H), 2.03–1.97 (m, 1 H), 1.88 (dt, J=13.3, 3.4 Hz, 1H), 1.76 (qd, J=13.7, 4.2 Hz, 1H), 1.71–1.66 (m, 2H), 1.61–1.53 (m, 1H), 1.32 (td, J=13.5, 4.3 Hz, 1H), 1.05 (s, 3H), 0.88 (s, 9H), 0.04 (s, 3H), 0.03 (s, 3H).

$^{13}$C NMR (CDCl$_3$, 100 MHz): ∂139.4, 121.4, 109.5, 78.1, 64.4, 64.2, 41.3, 39.6, 35.7, 30.9, 27.6, 25.9, 24.8, 18.0, 17.0, −4.0, −4.8.

Synthesis of Compound 56

The alkene 55 (1.964 g, 5.81 mmol) was dissolved in anhydrous THF: (20 mL) and cooled to 0° C., whereupon 1.0M BH$_3$ THF (5.9 mL, 5.9 mmol) was added dropwise to the stirred mixture. The mixture was allowed to come to room temperature and stirred overnight. After cooling to 0° C., $H_2O$ (0.2 mL) was added dropwise, followed immediately by 2.5 ml of 3M NaOH and subsequently 2.5 mL of 30% $H_2O_2$ (aq). The ice bath was removed and the mixture stirred for 3.5 h. After addition of $Et_2O$ (100 mL) and $H_2O$ (100 mL), the layers were separated. The aqueous layer was extracted repeatedly with $Et_2O$ (4×50 mL), and the combined organic layers washed with brine. After concentration in vacuo to a viscous oil, the crude product was dissolved in undistilled $CH_2Cl_2$ (100 mL) and treated with powdered 4 A molecular sieves (9 g; Aldrich), 4-methylmorpholine N-oxide (2.7 g), and tetrapropylammonium perruthenate catalyst (120 mg) while under $N_2$. After 2 hours, the mixture was filtered through Celite and concentrated in vacuo to a dark green oil. The crude product was dissolved in MeOH (100 mL) and treated with 20 mL of 3% NaOMe in MeOH for 10 h. After concentration in vacuo, the resulting oil was dissolved in $Et_2O$ (100 mL) and washed with $H_2O$ (2×100 mL) and brine. The $Et_2O$ layer was dried (MgSO$_4$), concentrated in vacuo, and chromatographed (30% $Et_2O$ in hexanes) to give trans-fused ketone 56 as the major product (1.571 g, 4.43 mmol, 76% from the alkene).

TLC (20% EtOAc in hexanes): Rf=0.34.

HRMS m/z (M+) for $C_{19}H_{34}O_4Si$ calcd. 354.2226, found 354.2214.

IR (film): 1716(s), 1110(s), 1093(s), 1051(s) cm$^{-1}$.

$^1$H NMR (CDCl$_3$, 400 MHz): ∂3.97–3.87 (m, 4H), 3.78 (dd, J=11.1, 5 Hz, 1H), 2.46 (dd, J=12.3, 3.7 Hz, 1H), 2.41–2.27 (m, 2H), 2.00–1.58 (m, 7H), 1.42 (td, J=13.4, 4.9 Hz, 1H), 0.88 (s, 9H), 0.78 (s, 3H), 0.07 (s, 6H).

$^{13}$C NMR (CDCl$_3$, 100 MHz): ∂210.4, 109.0, 77.2, 64.3, 64.2, 52.2, 42.4, 38.9, 35.1, 30.7, 30.5, 29.6, 25.8, 18.0, 10.6, −4.1, −4.8.

Synthesis of Compound 57

The ketone 56 (6.00 g, 16.9 mmol) was dissolved in anhydrous THF (100 mL) and cooled to −78° C. Solid potassium bis(trimethylsilyl)amide (4.2 g, 21 mmol; Aldrich) was weighed out separately under a $N_2$ atmosphere, dissolved in anhydrous THF (50 mL), and transferred via cannula to the cooled ketone solution. After 30 min, solid N-phenyltrifluoromethanesulfonimide (6.68 g, 18.7 mmol) was added in one portion. The mixture was maintained at −78° C. for 1 h, after which $H_2O$ (40 mL) was added and the resulting mixture was allowed to come to room temperature. Upon addition of $Et_2O$ (100 mL), the layers were separated. The aqueous layer was re-extracted with $Et_2O$ (5×80 mL). The combined organic layers were washed with brine, dried over MgSO$_4$, and concentrated in vacuo. The resulting oil was chromatographed (1:1 $CH_2Cl_2$: hexanes) to give pure enol triflate 57 (6.68 g, 13.74 mmol, 81%).

TLC (1:1 $CH_2Cl_2$: hexanes ): Rf=0.37.

HRMS m/z (M+) for $C_{20}H_{33}O_6SF_3Si$ calcd. 486.1719, found 486.1735.

IR (film): 1686 (w), 1420(s), 1210(s), 1143(s), 878(s), 838(s) cm$^{-1}$.

¹HNMR (CDCl₃, 400 MHz): $\delta$5.61 (td, J=5.1, 2.9 Hz, 1H), 3.99–3.91 (m, 4H), 3.54 (dd, J=9.4, 6.4 Hz, 1H), 2.67 (d quintet, J=13.5, 3.1 Hz, 1H), 2.35 (dtd, J=17.8, 6.0, 2.8 Hz, 1H), 2.14 (dqd, J=17.9, 4.5, 2.8 Hz, 1H), 1.84–1.76 (m, 3H), 1.67 (d quintet, J=13.5, 2.5 Hz, 1H), 1.59 (t, J=13.3 Hz, 1H), 1.24 (td, J=14.7, 4.6 Hz, 1H), 0.88 (s, 3H), 0.87 (s, 9H), 0.04 (s, 3H), 0.03 (s, 3H).

¹³CNMR (CDCl₃, 100 MHz): $\delta$149.0, 130.0, 116.2, 108.4, 74.3, 64.5, 64.2, 42.7, 39.1, 33.0, 31.3, 30.9, 30.6, 25.8, 18.0, 9.0, −4.1, −4.8.

Synthesis of Compound 58

The enol triflate 57 (2.865 g, 5.895 mmol) was dissolved in anhydrous DMF (25 mL) and to this solution was added N, N-diisopropylethylamine (2.8 mL, 2.1 g, 16 mmol) and powdered 4 A molecular sieves (1.1 g). To this slurry was added anhydrous MeOH (10 mL, 7.91 g, 247 mmol). The system was purged with carbon monoxide for 5 min, whereupon triphenylphosphine (240 mg, 0.916 mmol) and Pd(OAc)₂ (102 mg, 0.454 mmol) were added. The purging was discontinued, and the system was kept under ca. 2 psi of CO for 3–4 hours. The slurry was filtered through Celite and H₂O (50 mL) was added to the filtrate, followed by Et₂O (65 mL) (The crude ¹H NMR showed the presence of a minor product, thought to be the cis-fused isomer). After separation, the aqueous layer was re-extracted with Et₂O (4×30 mL). The combined organic layers were washed with brine, dried over MgSO₄, and concentrated in vacuo. Chromatography (15% Et₂O in hexanes) yielded pure methyl ester 58 (1.702 g, 4.298 mmol, 73%).

TLC (40% EtOAc in hexanes): Rf=0.76 (UV active).

HRMS m/z (M+) for C₂₁H₃₆O₅Si calcd. 396.2332, found 396.2345.

IR (film): 1718 (s), 1637(w), 1250(s), 1110(s), 1071(s) cm⁻¹.

¹H NMR (CDCl₃, 400 MHz): $\delta$6.54 (quintet, J=2.6 Hz, 1H), 4.03–3.91 (complex, 4H), 3.68 (s, 3H), 3.50 (dd, J=9.6; 6.4 Hz, 1H), 2.54 (d quintet, J=13.3, 2.9 Hz, 1H), 2.32 (m, 2H), 2.14 (m, 1H), 1.82 (m, 2H), 1.68 (m, 1H), 1.40 (t, J=7.2 Hz, 1H), 1.25 (m, 1H), 0.89 (s, 9H), 0.82 (s, 3H), 0.02 (s, 6H).

¹³C NMR (CDCl₃, 100 MHz): $\delta$167.8, 136.5, 132.9, 109.1, 74.8, 64.3, 64.1, 51.4, 41.1, 37.7, 33.4, 33.1, 31.5, 31.0, 25.8, 20.7, 18.0, 9.0, −4.1, −4.8.

Synthesis of Compound 59

The methyl ester 58 (3.97 g, 10.0 mmol) was dissolved in anhydrous hexanes (50 mL) with gentle warming. The solution was cooled to −78° C. and treated with 30 mL of 1.0M DIBAL in hexanes (Aldrich). After 1.5 h, the reaction mixture was quenched with H₂O (60 mL) followed by 1N HCl (40 mL) and allowed to warm to room temperature. The mixture was extracted repeatedly with EtOAc (4×100 mL). The organic layer was washed with brine (2×50 mL), dried over MgSO₄, and concentrated in vacuo to a semi-crystalline product. Chromatographic purification (5% MeOH in CH₂Cl₂) led to the allylic alcohol 57 (3.66 g, 9.95 mmol, 99%) as a white solid (mp=92°–94° C.).

TLC (5% MeOH in CH₂Cl₂): Rf=0.32.

HRMS m/z (M+) for C₂₀H₃₆O₄Si calcd. 368.2383, found 368.2377.

IR (film): 3416(s), 1472 (m), 1360(m), 1250(m), 1106 (s), 1072(s), 872(m), 836(s), 774(s) cm⁻¹.

¹HNMR (CDCl₃, 400 MHz): $\delta$5.57 (m, 1H), 4.03–3.92 (complex, 6H), 3.53 (dd, J=9.8, 6.5 Hz, 1H), 2.49 (br d, 1H), 2.23 (br d, 1H), 2.02 (m, 1H), 1.90 (dt, J=12.9, 2.5 Hz, 1H), 1.83 (dq, J=13.0, 2.5 Hz, 1H), 1.75 (dd, J=13.7, 4.7 Hz, 1H), 1.67 (d quintet, J=13.8, 2.5 Hz, 1H), 1.56 (t, J=13.2 Hz, 1H), 1.21 (td, J=12.8, 4.5 Hz, 1H), 0.87 (s, 9H), 0.79 (s, 3H), 0.02 (s, 6H).

¹³CNMR (CDCl₃, 100 MHz): $\delta$137.9, 123.1, 109.4, 75.8, 65.1, 64.3, 64.2, 41.7, 37.4, 33.3, 33.2, 32.2, 30.8, 25.8, 18.0, 8.9, −4.0, −4.8.

Synthesis of Compound 60

The allylic alcohol 59 (3.56 g, 9.67 mmol) was dissolved in 200 mL of acetone/H₂O (8/1), and to this solution was 4-methylmorpholine N-oxide (2.4 g, 20 mmol). The system was purged with N₂ for 10 minutes before 5 mL of a 0.1M solution of OsO₄ in tert-butyl alcohol was added. After stirring for 12 h at room temperature the reaction flask was cooled to 0° C. and 50 mL of 10% NaHSO₃ (aq) was added. The resulting brown slurry was extracted with EtOAc (5×100 mL). The combined extracts were washed with brine, dried over MgSO₄ and concentrated in vacuo to a light brown solid. ¹HNMR analysis of the crude product, showed a 4:1 mixture of triols. Chromatography (5% MeOH in CH₂Cl₂) gave the major triol 60 (2.56 g, 6.36 mmol, 66%) as a white crystalline powder (mp=117°–118° C.).

TLC (10% MeOH in CH₂Cl₂): Rf=0.39 (Rf of minor triol=0.32).

IR (film): 3441(s), 1256(m), 1102(s), 864(m), 835(m) cm⁻¹.

HRMS m/z (M+) for C₂₀H₃₈O₆Si calcd. 402.2438, found 402.2447.

¹H NMR (CDCl₃, 400 MHz): $\delta$4.00 (br s, 1H), 3.98–3.90 (m, 4H), 3.77 (dd, J=11.5, 5.5 Hz, 1H), 3.56 (m, 2H), 2.06 (dd, J=14.7, 2.7 Hz, 1H), 1.87 (m, 2H), 1.80–1.70 (M, 2H), 1.62 (m, 2H), 1.52 (t, J=13.2 Hz, 1H), 1.29 (td, J=12.6, 6.4 Hz, 1H), 0.87 (s, 9H), 0.82 (s, 3H), 0.06 (s, 3H), 0.04 (s, 3H).

¹³C NMR (CDCl₃, 100 MHz): $\delta$109.3, 73.7, 69.4, 64.3, 64.2, 62.0, 42.5, 38.8, 38.0, 34.8, 30.9, 30.1, 25.9, 18.0, 12.3, −4.0, −4.8.

Synthesis of Compound 61

The triol 60 (536 mg, 1.33 mmol) was dissolved in CH₂Cl₂ (45 mL) and anhydrous pyridine (1.15 mL, 14.2 mmol) and the resulting solution was cooled to −78° C., whereupon freshly distilled chlorotrimethylsilane (0.236 mL, 1.86 mmol) was added and the mixture allowed to come to room temperature for 1 h. TLC monitoring (40% EtOAc in hexanes) revealed the presence of what was presumed to be the primary trimethylsilyl ether intermediate (Rf=0.54) along with a trace amount of the disilyl ether byproduct (Rf=0.86; primary and secondary alcohols etherified). The mixture was cooled to −78° C. and treated with trifluoromethanesulfonic anhydride (5.75 mL of a 1.0M stock solution in CH₂Cl₂) and allowed to come to room temperature for 1 h. TLC monitoring (40% EtOAc in hexanes) indicated complete conversion of the initial intermediate to its triflate (Rf=0.85). The mixture was finally treated with ethylene glycol (6 mL) and refluxed for 12 h. Water (20 mL) and brine (20 mL) were added and the layers were separated. The aqueous layer was extracted repeatedly with CH₂Cl₂ (6×15 mL). The combined organic layers were washed with brine, dried over Na₂SO₄, and concentrated in vacuo. ¹HNMR analysis of the crude yellow oil showed the desired oxetane 61 to be the major product by a 6:1 margin over the migration byproduct 62. The mixture was chromatographed (gradient elution of 40% to 60% EtOAc in hexanes) to obtain pure 61 (353 mg, 0.919 mmol, 69%) as a white solid.

TLC (40% EtOAc in hexanes): Rf of 61=0.17; Rf of 62=0.30.

HRMS of 61 m/z (M$^+$+1) for $C_{20}H_{37}O_5Si$ calcd. 385.2410, found 385.2410. HRMS of 62 m/z (M$^+$) for $C_{20}H_{36}O_5S$; calcd. 384.2332, found 384.2323.

IR (film) of 61: 3416(br), 1094(s), 859(s), 836(s), 774(s) cm$^{-1}$. IR (film) of 62: 3456(br), 1710(s), 1253(s), 1094 (vs), 863(s), 836(s), 775(s) cm$^{-1}$.

$^1$H NMR of 61 (CDCl$_3$, 400 MHz): ∂4.78 (dd, J=9.1, 2.2 Hz, 1H), 4.46 (d, J=7.6 Hz, 1H), 4.26 (d, J=7.6 Hz, 1H), 3.96-3.89 (m, 4H), 3.44 (dd, J=10.6, 7.24 Hz, 1H), 2.27 (ddd, J=16.3, 9.2, 7.1 Hz, 1H), 1.88 (ddd, J=15.1, 10.7, 2.4 Hz, 1H), 1.83-1.72 (m, 2H), 1.68-1.55 (m, 5H), 1.21 (s, 3H), 0.87 (s, 9H), 0.02 (s, 6H).

$^{13}$NMR of 61 (CDCl$_3$, 100 MHz): ∂108.8, 88.1, 76.4, 74.0, 64.4, 64.3, 46.7, 37.6, 36.5, 30.9, 30.2, 29.7, 25.8, 18.0, 9.5, −4.0, −4.8.

$^1$H NMR of 62 (CDCl$_3$, 400 MHz): ∂3.95-3.81 (m, 4H), 3.63-3.56 (m, 2H), 2.58-2.48 (m, 3H), 1.91 (quintet, J=5.0 Hz, 1H), 1.81-1.60 (m, 5H), 1.40 (td, J=13.0, 5.3 Hz, 1H), 0.85 (s, 9H), 0.72 (s, 3H), 0.05 (s, 6H).

$^{13}$C NMR of 62 (CDCl$_3$, 100 MHz): ∂213.0, 108.9, 64.3, 64.2, 62.1, 52.3, 49.1, 42.9, 35.0, 33.7, 30.1, 29.4, 25.7, 17.9, 10.6, −4.1, −4.8.

Synthesis of Compound 63

Oxetane 61 (20 mg, 0.052 mmol) was dissolved in anhydrous THF (2 mL) and treated with 1.0M tetrabutyl ammonium fluoride in THF (0.100 mL, 0.100 mmol). The mixture was heated to reflux for 12 h, cooled to room temperature, and chromatographed directly (EtOAc as eluant) to give 63 (13 mg, 0.048 mmol, 93%). Recrystallization from CHCl$_3$ yielded a fine, white crystalline solid from which a single crystal x-ray was obtained.

mp=232° C. (dec).

TLC (EtOAc): Rf=0.18.

HRMS m/z (M$^+$) for $C_{14}H_{22}O_5$ calcd. 270.1467, found 270.1478

$^1$H NMR (CDCl$_3$, 400 MHz): ∂4.83 (dd, J=2.9, 9.0 Hz, 1H), 4.46 (d, J=7.6 Hz, 1H), 4.28 (d, J=7.5 Hz, 1H), 3.99-3.89 (m, 4H), 3.50 (m, 1H), 2.44 (quintet, J=8 Hz, 1H), 1.90-1.60 (m, 6H), 1.41-1.29 (m, 2H), 1.25 (s, 3H).

$^{13}$C NMR (CD$_3$OD, 100 MHz): ∂110.1, 89.9, 77.8, 76.8, 74.4, 65.3, 65.2, 47.7, 38.3, 37.6, 37.3, 32.0, 30.7, 9.9.

Synthesis of Compound 64

The ketal 61 (1.320 g, 3.438 mmol) was dissolved in 12 mL of acetone and 1 mL of H$_2$O. To this solution was added collidinium tosylate (0.70 g, 2.4 mmol) and the mixture was heated to reflux. Due to the sluggishness of the deketallization, more collidinium tosylate (0.60 g, 2.0 mmol) and H$_2$O (1 mL) were added over a period of 120 h. The majority of starting ketal was consumed during this period, as monitored by TLC (Rf of 61 with EtOAc eluant=0.52; Rf of 64=0.65). The mixture was cooled to room temperature and concentrated in vacuo to remove most of the acetone. To the crude product was added H$_2$O (10 mL) and EtOAc (50 mL) and the layers were separated. The aqueous phase was repeatedly extracted with EtOAc (5×40 mL) and the combined organic phases were washed with brine, dried over MgSO$_4$, and concentrated in vacuo. Chromatography (40% EtOAc in hexanes) yielded pure 64 as a white solid (0.985 g, 2.897 mmol, 84%). Recrystallization from n-pentane/CH$_2$Cl$_2$ (10/1) gave fine white needles (mp=152° C.).

IR (film): 3375(s), 1710(s), 1253(s), 1083(s), 940(m), 836(s), 772(s) cm$^{-1}$.

HRMS m/z (M$^+$+1) for $C_{18}H_{33}O_4Si$ calcd. 341.2148, found 341.2154.

$^1$H NMR (CDCl$_3$, 400 MHz): ∂4.80 (d, J=7.9 Hz, 1H), 4.55 (d, J=7.8 Hz, 1H), 4.27 (d, J=7.8 Hz, 1H), 3.46 (dd, J=10.6, 7.2 Hz, 1H), 2.48 (td, J=15.2, 6.4 Hz, 1H), 2.38-2.29 (m, 5H), 2.13 (dd, J=13.0, 5.3 Hz, 1H), 1.94 (t, J=13.2 Hz, 1H), 1.72 (dd, J=11.5, 5.9 Hz, 1H), 1.38 (s, 3H), 1.33 (td, J=13.6, 4.5 Hz, 1H), 0.88 (s, 9H), 0.03 (s, 3H), 0.01 (s, 3H).

$^{13}$C NMR (CDCl$_3$, 100 MHz): ∂210.4, 88.0, 76.1, 74.0, 48.7, 38.7, 37.7, 37.6, 37.4, 36.7, 25.8, 17.9, 9.6, −4.0, −4.9.

Synthesis of Compound 65

Freshly distilled diisopropylamine (0.150 mL, 108 mg, 1.07 mmol) was charged to a 10 mL roundbottom flask containing 3 mL anhydrous THF. The solution was cooled to −78° C. and treated with n-BuLi (0.355 mL, 2.5M in hexanes, 0.888 mmol). After 15 min at −78° C., ketone 64 (142 mg, 0.418 mmol) in 2 mL anhydrous THF was transferred via cannula to the lithium diisopropylamide solution. After 1.5 h, chlorotrimethylsilane (0.120 mL, 103 mg, 0.945 mmol) was added and the reaction mixture warmed to room temperature for 1 h, whereupon it was poured into n-pentane/H$_2$O (5 mL/5 mL) and extracted. The aqueous layer was reextracted with n-pentane (3×5 mL). The combined organic layers were washed with brine, dried over MgSO$_4$, and concentrated in vacuo to the crude enol ether, which was redissolved in anhydrous acetonitrile (4 mL) at reflux. After dissolution of the enol ether, Pd(OAc)$_2$ (105 mg, 0.468 mmol) was added and the resulting mixture maintained at reflux for 5 h. At this time, MeOH (3 mL) and K$_2$CO$_3$ powder (200 mg, 1.45 mmol) were added while maintaining reflux for 1 h. After cooling to room temperature, the slurry was filtered through Celite (MeOH wash) and the filtrate concentrated in vacuo to a yellow oil. Chromatography (3% MeOH in CH$_2$Cl$_2$) yielded the desired enone 65 (109 mg, 0.322 mmol, 77%) contaminated with a trace amount of an unidentified byproduct.

TLC (20% EtOAc in hexanes): Rf=0.14 (UV active).

HRMS m/z (M$^+$+1) for $C_{18}H_{31}O_4Si$ calcd. 339.1992, found 339.1986

IR (film): 3413 (s), 1681 (s), 1256 (s), 1069 (s), 837 (s), 776 (s) cm$^{-1}$.

$^1$H NMR (CDCl$_3$, 400 MHz): ∂7.12 (d, J=10.2 Hz, 1H), 5.90 (d, J=10.2 Hz, 1H), 4.83 (dd, J=8.8, 1.6 Hz, 1H), 4.54 (d, J=7.8 Hz, 1H), 4.34 (d, J=7.8 Hz, 1H), 3.65 (dd, J=10.0, 7.6 Hz, 1H), 2.72 (s, 1H), 2.48-2.37 (m, 3H), 2.07 (ddd, J=12.7, 6.0, 0.8 Hz, 1H), 1.93 (ddd, J=15.3, 10.0, 1.9 Hz, 1H), 1.39 (s, 3H), 0.92 (s, 9H), 0.06 (s, 6H).

$^{13}$C NMR (CDCl$_3$, 100 MHz): ∂199.1, 157.2, 126.8, 87.7, 76.7, 73.4, 72.1, 45.6, 37.3, 33.3, 25.8, 18.0, 11.3, −3.9, −5.0.

Synthesis of Compound 66

Alcohol 65 (144 mg, 0.426 mmol) was dissolved in 2 mL anhydrous DMF and the resulting solution treated with imidazole (200 mg, 2.94 mmol) and tert-butyldimethylsilyl chloride (215 mg, 1.43 mmol). The mixture was heated to 80° C. for 12 h, then poured into Et$_2$O (10 mL) and H$_2$O (5 mL) and extracted. The aqueous layer was re-extracted with Et$_2$O (5×10 mL). The combined organic phases were washed with brine, dried over MgSO$_4$, and concentrated in vacuo. Chromatography (5% EtOAc in hexanes) yielded the desired silyl ether 66 (110 mg, 0.243 mmol, 57%) along with starting alcohol 65 (25 mg, 0.074 mmol, 17% recovered).

TLC (5% EtOAc in hexanes): Rf=0.18 (UV active).

HRMS m/z (M+ +1) for C$_{24}$H$_{45}$O$_4$Si$_2$ calcd 453.2857, found 453.2905.

IR (film): 1684(s), 1255(s), 1094(s), 836(s), 775(s) cm$^{-1}$. $^1$H NMR (CDCl$_3$, 400 MHz): ∂7.10 (d, J=10.0 Hz, 1H), 5.89 (d, J=10.1 Hz, 1H), 4.89 (d, J=8.0 Hz, 1H), 4.42 (d, J=7.3 Hz, 1H), 4.37 (d, J=7.2 Hz, 1H), 3.64 (dd, J=9.5, 7.9 Hz, 1H), 2.42–2.34 (m, 3H), 2.02 (t, J=8.0 Hz, 1H), 1.92 (ddd, J=15.5, 9.6, 1.4 Hz, 1H), 1.39 (s, 3H), 0.92 (s, 9H), 0.87 (s, 9H), 0.13 (s, 3H), 0.10 (s, 3H), 0.08 (s, 3H), 0.07 (s, 3H).

$^{13}$C NMR (CDCl$_3$, 100 MHz): ∂198.9, 157.0, 126.7, 86.6, 76.6, 74.7, 72.3, 47.2, 41.3, 37.5, 33.2, 25.7, 25.5, 18.0, 17.9, 11.2, −3.0, −3.1, −3.9, −5.1.

Synthesis of Compound 67

To alcohol 65 (85 mg, 0.251 mmol) in 2 mL anhydrous CH$_2$Cl$_2$ was added anhydrous pyridine (0.026 mL, 25 mg, 0.32 mmol) at 0° C. followed by chlorotrimethylsilane (0.036 mL, 31 mg, 0.28 mmol). The reaction mixture was warmed to room temperature for 1 h, then poured into H$_2$O (5 mL) and extracted with CH$_2$Cl$_2$ (3×15 mL). The combined CH$_2$Cl$_2$ layers were washed with brine, dried over MgSO$_4$, and concentrated in vacuo. Chromatography (5% EtOAc in hexanes) yielded pure 66 (91 mg, 0.222 mmol, 88%).

TLC (40% EtOAc in hexanes): Rf=0.83 (UV active).

$^1$H NMR (CDCl$_3$; 400 MHz): ∂7.09 (d, J=10.1 Hz, 1H), 5.89 (d, J=10.1 Hz, 1H), 4.91 (d, J=7.5 Hz, 1H), 4.43 (dd, J=10.8 Hz, 7.6 Hz, 2H), 3.65 (dd, J=9.5, 8.0 Hz, 1H), 2.43–2.36 (m, 3H), 2.04 (t, J=8.6 Hz, 1H), 1.92 (ddd, J=15.5, 9.6, 1.4 Hz, 1H), 1.39 (s, 3H), 0.92 (s, 9H), 0.16 (s, 9H), 0.07 (s, 3H), 0.06 (s, 3H).

Synthesis of Compound 68

To enone 67 (6 mg, 0.0146 mmol) dissolved in anhydrous THF (1 mL) and cooled to −78° C. was added dropwise potassium bis(trimethylsilyl)amide (0.035 mL of 0.5M solution in toluene, 0.0175 mmol). After 30 min a yellow color developed, and a solution of N-phenylsulfonyl phenyloxiziridine (10 mg, 0.038 mmol) in THF (1 mL) was added slowly down the side of the flask. After 10 min, H$_2$O (1 mL) was added and the mixture was allowed to warm to room temperature for 30 min, whereupon it was poured into EtOAc (5 mL) and brine (5 mL) in a separatory funnel and subsequently extracted. The aqueous phase was re-extracted with EtOAc (6×5 mL). The combined organic phases were washed with brine, dried over MgSO$_4$, concentrated in vacuo, and chromatographed (gradient elution, 20% to 40% EtOAc in CH$_2$Cl$_2$) to give pure diol 68 as a white solid (4 mg, 0.0113 mmol, 77%).

TLC (20% EtOAc in CH$_2$Cl$_2$): Rf=0.13 (UV active).

IR (film): 3461(s), 1691(s), 1255(m), 1157(s), 1100(s), 1045(m), 869(s), 838(s), 776(s) cm$^{-1}$.

$^1$H NMR (CDCl$_3$, 400 MHz): ∂7.20 (d, J=10.1 Hz, 1H), 6.01 (d, J=10.1 Hz, 1H), 4.88 (d, J=8.5 Hz, 1H), 4.61 (d, J=7.2 Hz, 1H), 4.56 (d, J=7.3 Hz, 1H), 4.53 (dd, J=13.0, 1.2 Hz, 1H), 4.03 (s, 1H), 3.76 (d, J=1.3 Hz, 1H), 3.68 (dd, J=9.6, 7.7 Hz, 1H), 2.43 (quintet, J=7.8 Hz, 1H), 2.07 (d, J=13.0 Hz, 1H), 1.93 (ddd, J=15.4, 9.8, 1.4 Hz, 1H), 1.53 (s, 3H), 0.92 (s, 9H), 0.06 (s, 3H), 0.05 (s, 3H).

$^{13}$C NMR (CDCl$_3$, 100 MHz): ∂199.3, 158.9, 123.0, 85.0, 76.8, 72.8, 71.9, 70.4, 52.0, 43.0, 37.2, 25.7, 18.0, 11.7, −3.9, −5.1.

Synthesis of Compound 69

Freshly distilled diisopropylamine (0.018 mL, 13 mg, 0.13 mmol) was charged to a dry 5 mL roundbottom flask containing 1 mL anhydrous THF. The solution was cooled to −78° C. and treated with n-BuLi (0.032 mL of 2.5M in hexanes, 0.080 mmol). After 15 min at −78° C., enone 15 (18.0 mg, 0.0398 mmol), dissolved in 1 mL THF, was transferred into the lithium diisopropylamide solution via cannula. After maintaining at −78° C. for 45 min, chlorotrimethylsilane (0.015 mL, 13 mg, 0.12 mmol) was added and the reaction mixture allowed to come to room temperature for 1 h, whereupon it was poured into n-pentane (5 mL) and H$_2$O (5 mL) and extracted. The aqueous layer was re-extracted with n-pentane (3×5 mL) and the combined organic layers were washed with brine, dried over MgSO$_4$, and concentrated in vacuo. The crude product was dissolved in anhydrous CH$_2$Cl$_2$ (1 mL) and to the resulting solution was added anhydrous NaHCO$_3$ powder (20 mg, 0.24 mmol). The slurry was cooled to −78° C. and purged with ozone until a light blue color persisted, whereupon excess ozone was purged with N$_2$. Triphenylphosphine (27 mg, 0.12 mmol) was added and the mixture was allowed to come to room temperature for 1.5 h, at which time it was filtered through cotton and concentrated in vacuo to a yellow oil. Chromatography (CH$_2$Cl$_2$ as eluant) yielded dialdehyde 69 (6.3 mg, 0.014 mmol, 36%).

TLC (CH$_2$Cl$_2$): Rf=0.27.

HRMS m/z (M+ +1) for C$_{22}$H$_{43}$O$_5$Si$_2$ calcd 443.2650, found 443.2613.

IR (film) 2723(w), 1728(s), 1472(m), 1257(s), 1174(m), 1098(s), 837(s), 777(s) cm$^{-1}$.

$^1$H NMR (CDCl$_3$, 400 MHz): ∂9.66 (s, 1H), 9.60 (d, J=0.4 Hz, 1H), 4.90 (dd, J=8.3, 2.0 Hz, 1H), 4.63 (dd, J=7.4, 1.0 Hz, 1H), 4.36 (d, J=7.4 Hz, 1H), 4.00 (dd, J=9.2, 6.6 Hz, 1H), 2.97 (s, 1H), 2.31 (ddd, J=15.1, 8.2, 6.6 Hz, 1H), 1.94 (ddd, J=15.3, 9.2, 2.2 Hz, 1H), 1.52 (s, 3H), 0.89 (s, 9H), 0.85 (s, 9H), 0.19 (s, 3H), 0.18 (s, 3H), 0.03 (s, 3H), −0.02 (s, 3H).

$^{13}$C NMR (CDCl$_3$, 100 MHz): ∂206.4, 200.2, 87.1, 79.1, 73.2, 71.7, 62.0, 51.5, 36.0, 25.5, 17.8, 10.8, −2.9, −4.2, −5.3.

Discussion

This disclosure presents a synthesis of a potential C,D-ring fragment of 1, starting from the Wieland-Miescher ketone (27), with appendages for the potential elaboration of the remaining A and B rings.

Figure 13:
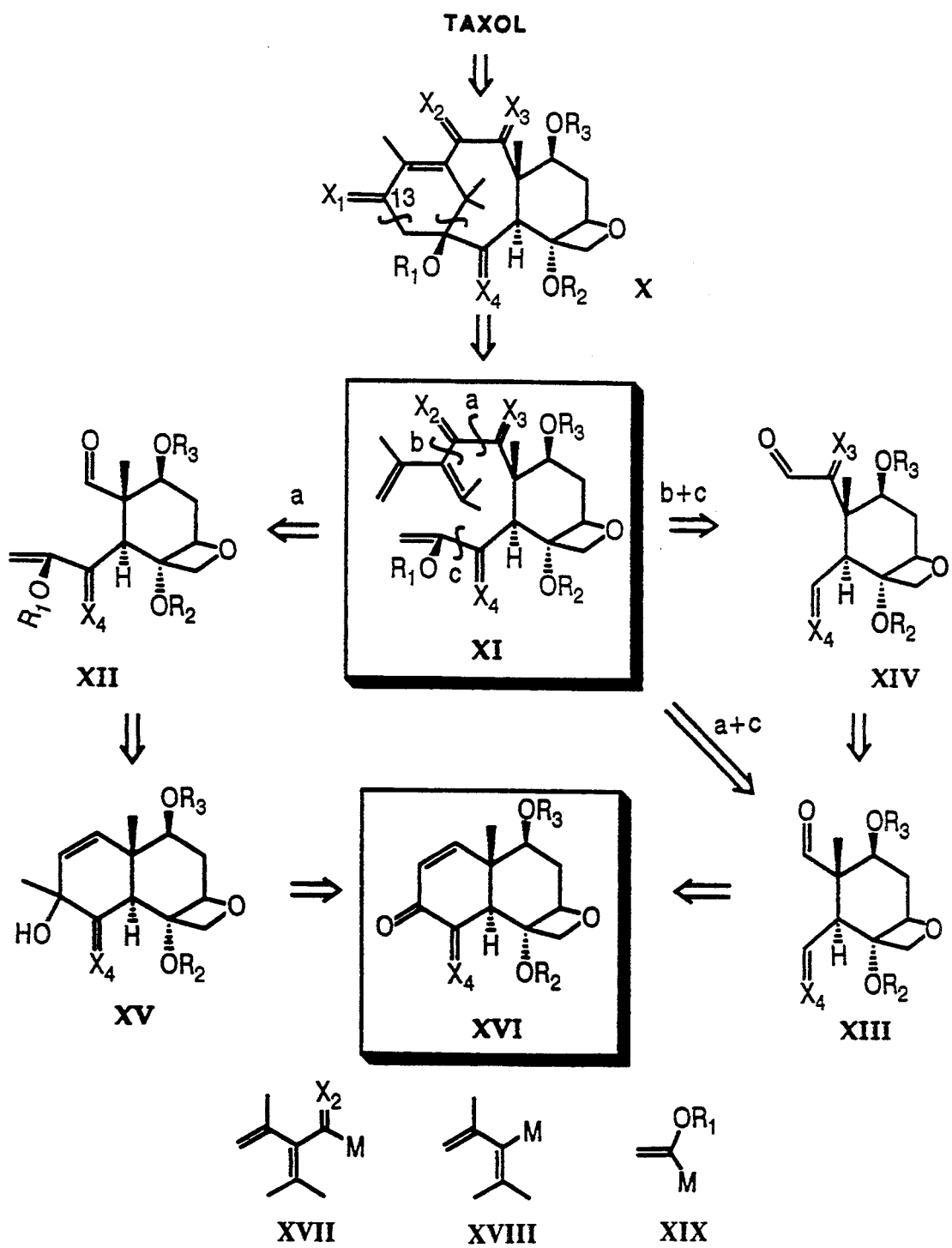
FIG. 13. Retrosynthetic analysis of Route 2(a) total synthesis of taxol.

A retrosynthetic analysis of 1 is given in FIG. 13. Functional group interchange yields the general structure I which is the product of an intra-molecular Diels-Alder cycloaddition of II for the simultaneous construction of rings A and B (28). Cycloaddition precursor II is assembled by three main pathways as designated by bond cleavages given in the Figure, i.e. pathway a, b+c, or a+c.

KEY: For all $R_a$, a=1, 2, 3 ..., R=H, acyl, alkyl, aryl, TBS, TES, TMS, and/or TBDPS unless otherwise specified. For all $X_a$, a=1, 2, 3 ..., X=H,H; H,OR; O,O; OCH$_2$CH$_2$O; and/or SCH$_2$CH$_2$CH$_2$S unless otherwise specified.

Bond a would result from a nucleophilic attack of VIII (M=metal; $X_2$=SCH$_2$CH$_2$CH$_2$S; H,H) (29) upon aldehyde III, which in turn is derived from degradation of olefin VI. The degradation precursor VI is the product of methyllithium addition to the central intermediate, enone VII. Bond b is formed by addition of the known metallated diene IX to the aldehyde function in V, which is the homologation product derived from aldehyde IV. Introduction of the dienophile (bond c) results from addition of a two carbon acyl-anion equivalent such as X.

Figure 14:
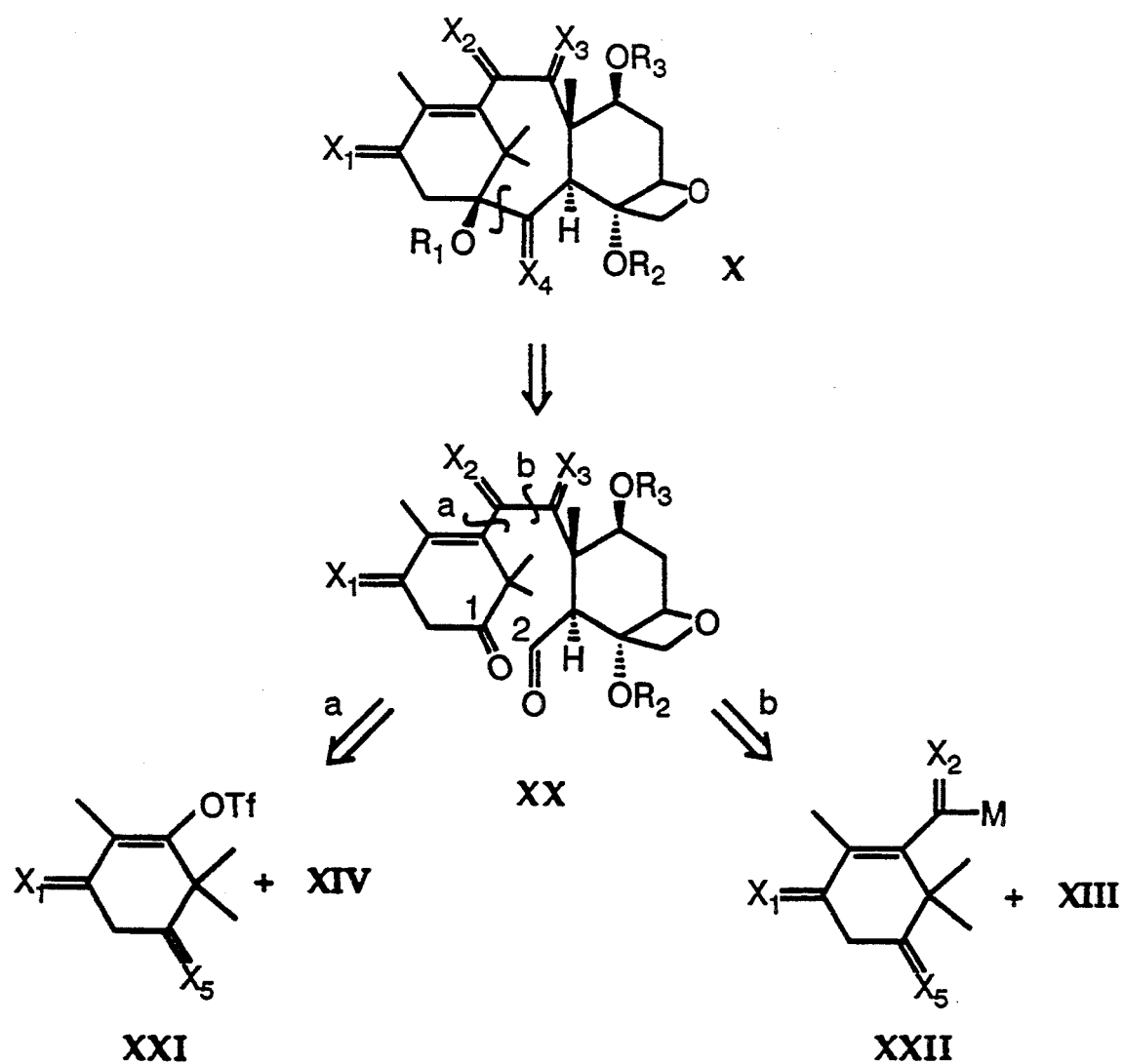
FIG. 14. Retrosynthetic analysis of Route 2(b) total synthesis of taxol.

An alternative route invokes an entirely different construction of the general tetracyclic intermediate I in which the B-ring is formed via a reductive coupling of the dicarbonyl intermediate XI (FIG. 14). Assembly of the cyclization precursor XI is achieved by coupling a pre-formed A-ring synthons XII or XIII (30). Pathway a represents Nozaki-Kishi (13, 14) coupling of enol triflate with aldehyde V. Alternatively, pathway b is possible by nucleophilic addition of XIII (M=metal; $X_1$=H,H; $X_2$=SCH$_2$CH$_2$CH$_2$S; $X_5$=OCH$_2$CH$_2$O) to aldehyde IV.

All of the aforementioned routes require the synthesis of intermediates containing C,D-ring system and equipped with appropriate functionality to elaborate the remaining A and B rings.

Results

Figure 15:
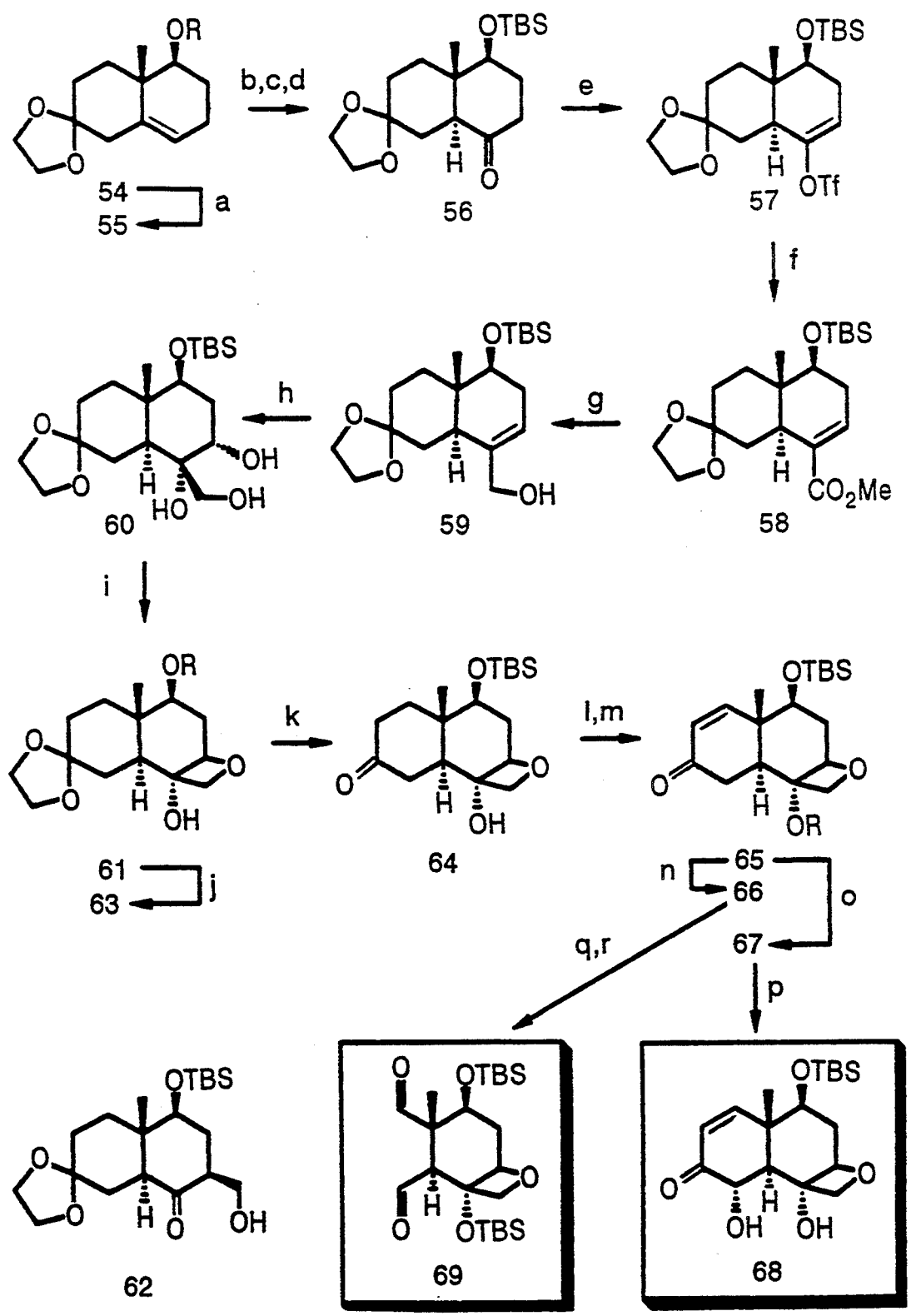
FIG. 15. Preparation of compounds 68 and 69. (a) TBSOTf/2,6-lutidine/CH₂Cl₂/0° C.;97%; (b) i) BH₃-THF ii) H₂O₂/NaOH; (c) 10 mol % TPAP/NMO/-powdered 4 Å molecular sieves/CH₂Cl₂; (d) 3% NaOMe in MeOH; 76% overall for steps b–d; (e) i) KHMDS/THF/−78° C./30 min ii) PhNTf₂/−78° C./1 h; 81%; (f) DMF/3 eq. Hünig's base/40 eq. anh. MeOH/8 mol % Pd(OAc)₂/16 mol % Ph₃P/2 psi CO/4 h; 73%; (g) DIBAH/hexanes/−78% °C.; 99%; (h) 5 mol % OsO₄/NMO/acetone/H₂O; 66%; (i) i) TMSCl/pyr/CH₂Cl₂/−78° C. to rt ii) Tf₂O/−78° C. to rt iii) ethylene glycol/40° C./12 h; 69% overall; (j) TBAF/THF/reflux/10 h; 93%; (k) 1 eq. collidium tosylate/acetone:H₂O (12:1)/reflux/120 h; 84%; (l) i) 2 eq. LDA/THF/−78° C./1.5 h ii) 2.3 eq. TMSCl/−78° to rt; (m) i) 1.1 eq. Pd(OAc)₂/MeCN/reflux ii) MeOH/K₂CO₃; 77% overall; (n) TBSCl/imidazole/DMF/80° C.; 57%; (o) TMSCl/pyr/CH₂Cl₂; 88%; (p) i) KHMDS/THF/−78° C. ii) N-phenylsulfonyl phenyloxaziridine iii) H₂O/−78° C. to rt; 77%; (q) i) LDA/THF/−78° C. ii) TMSCl/−78° C. to rt (r) i) O₃/CH₂Cl₂/−78° C. ii) Ph₃P/−78° C. to rt; 36%.

We began on the assumption that the ketone (27) offered a viable substrate for the construction of the C,D portion of 1, given its ready conversion to 54 (FIG. 15) (for ketone production, see (31, 32); for deconjugative ketalization and hydroboration/oxidation, see (33), and its availability in optically active form, see (34, 35, 36, 37)). The equatorial secondary alcohol of 54 (a pro C-7 hydroxyl in the C-ring of 1) was protected as the t-butyldimethylsilyl (TBS) ether (38) to give 55. The olefin of 55 was hydroborated and oxidized according to the reported protocol (33) to give a mixture of diastereomeric alcohols. Tetrapropylammonium perruthenate catalyzed oxidation (39, 40) gave the cis and trans-fused ketones which converged to the trans 56 after base catalyzed equilibration. For the purpose of one carbon homologation, 56 was converted to the enol triflate 57 by O-sulfonylation of its potassium enolate with N-phenyltrifluoromethane sulfonimide (41, 42, 43). Palladium catalyzed carbomethoxylation (44) of 57 yielded the unsaturated ester 58, which was readily reduced with DIBAH to the corresponding allylic alcohol 59. Osmylation of 59 under catalytic conditions yielded a 4:1 diastereomeric ratio of triols, 60 being the major product.

After isolation by flash chromatography (8), triol 60 was converted in one pot to oxetane 61 (45). Careful silylation of the primary alcohol was achieved with TMSCl/pyridine in CH$_2$Cl$_2$ (−78° C. to rt) as monitored by TLC; the solution was cooled back to −78° C. and treated with trifluoromethanesulfonic anhydride. After warming to rt, TLC indicated that the secondary alcohol had been converted to its triflate. While fluoride treatment tended to promote the migration of the hydroxymethyl function to give 62, it was observed that alcoholic desilylation yielded oxetane 61 as the major product, the best result being achieved with ethylene glycol (analysis of the crude $^1$H NMR spectrum indicated a ca. 6:1 ratio of 61:63). The desired oxetane 61 was isolated in 69% overall yield from triol 60. Removal of the TBS ether with tetrabutylammonium fluoride gave diol 63, of which a single crystal x-ray was obtained confirming the structure. It will be noted that compounds 61 and 63 are the first synthesized subunits containing the full complement of oxygens corresponding to the C,D section of taxol 1.

Having constructed pro C and D rings of 1, we sought to unravel appendages useful to the introduction of rings A and B. To this end, the ketal of 61 was removed under mildly acidic conditions (collidinium tosylate) to maintain the integrity of both the TBS ether and the oxetane ring. Ketone 64 was subsequently converted to the corresponding enone 65 by way of its silyl enol ether (46) with Pd(OAc)$_2$ (47, 48). The tertiary alcohol of 65 was protected as the TBS ether, though only under forcing conditions (DMF/imidazole/80° C./12 h), with an excess of TBSCl to give 66. Degradation of 66 to dialdehyde 69 was accomplished by ozonolysis of the silyl dienol ether, albeit in low isolated yield (36%).

With a view to obtaining the needed oxygenation at C-2, and in the interest of exploring alternative degradative pathways, we studied the oxidation of the enone system. The tertiary alcohol of 65 was readily converted to the corresponding TMS ether 68. The potassium dienolate of 68 was generated with potassium bis(trimethylsilyl)amide and subsequently treated with the Davis oxaziradine to give diol 69 after aqueous workup. Formally, C-4 of 69 can be viewed as corresponding in stereochemistry to C-2 of 1.

Figure 16:
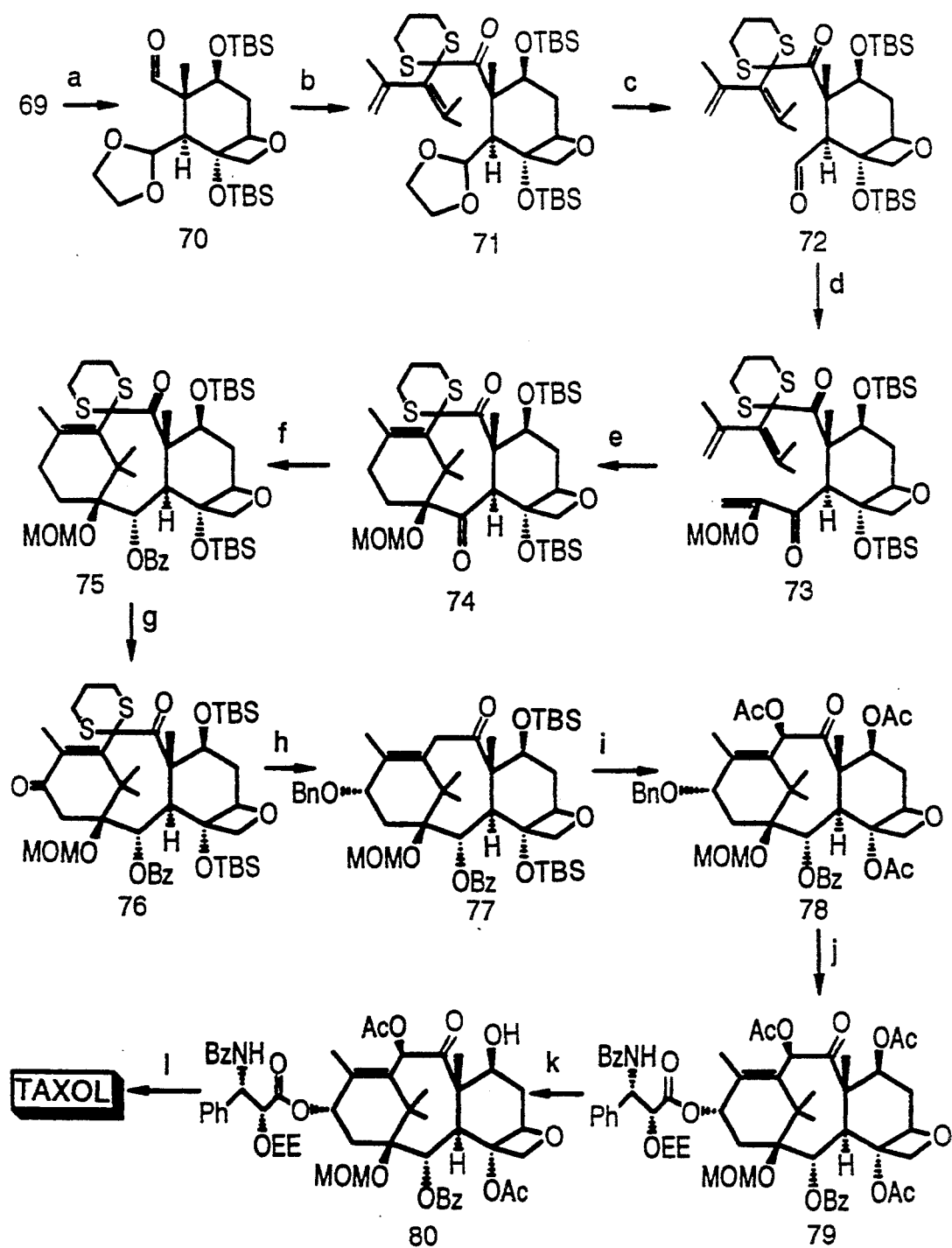
FIG. 16. Total synthesis of taxol from dialdehyde 69. (a) ethylene glycol, PPTS; (b) i) XVII (X₂=SCH₂CH₂CH₂S; M=Li); ii) Swern; (c) acetone, PPTS; (d) i) X (R₁=MOM; M=Li); ii) Swern; (e) xylene, reflux; (f) i) NaBH₄; ii) BzCl/pyr; (g) i) SeO₂/dioxane; ii) Swern; (h) i) L-selectride; ii) BnBr/NaH; iii) Raney Ni; (i) i) KHMDS; then N-phenyl phenylsulfonyloxaziridine; ii) TBAF; iii) Ac₂O/pyr/DMAP; (j) i) H₂/Pd-C; ii) See (49); (k) LiOH/H₂O/THF; (l) dilute acid/H₂O.

Total Synthesis of Taxol from Dialdehyde 18 (FIG. 16)

Selective ketalization of the less hindered aldehyde of 69 gives 70. Addition of the lithiodithiane VII ($X_2$=SCH$_2$CH$_2$CH$_2$S; M=Li) followed by Swern oxidation yields 71. Release of the ketal of 71 to aldehyde 72 followed by addition of the vinyllithium X ($R_1$=MOM; M=Li) produces the Diels-Alder precursor 73. Upon heating, 73 will cyclize to the tricyclic 74. Stereoselective reduction of the less hindered ketone of 74 yields 75 after benzoylation of the newly generated (α) secondary alcohol. Allylic oxidation in the A-ring of 75, followed by Swern oxidation if necessary, gives enone 76. The A-ring carbonyl reduces to the α configuration using a bulky borohydride. Subsequent benzyl protection and Raney nickel reduction of the thioketal produces 77. Franklin Davis hydroxylation of the potassium enolate of ketone 77 gives the corresponding hydroxy ketone in which the oxaziridine approaches from the convex face. After fluoride induced desilylation with TBAF, peracetylation yields 78. Hydrogenolysis of the benzyl ether and subsequent side chain coupling produces 79. The acetate at C-7 is selectively removed to 80, which in turn is doubly deprotected by simultaneous removal of the MOM and EE groups to give taxol.

Simple Mimics of Taxol

Figure 17:
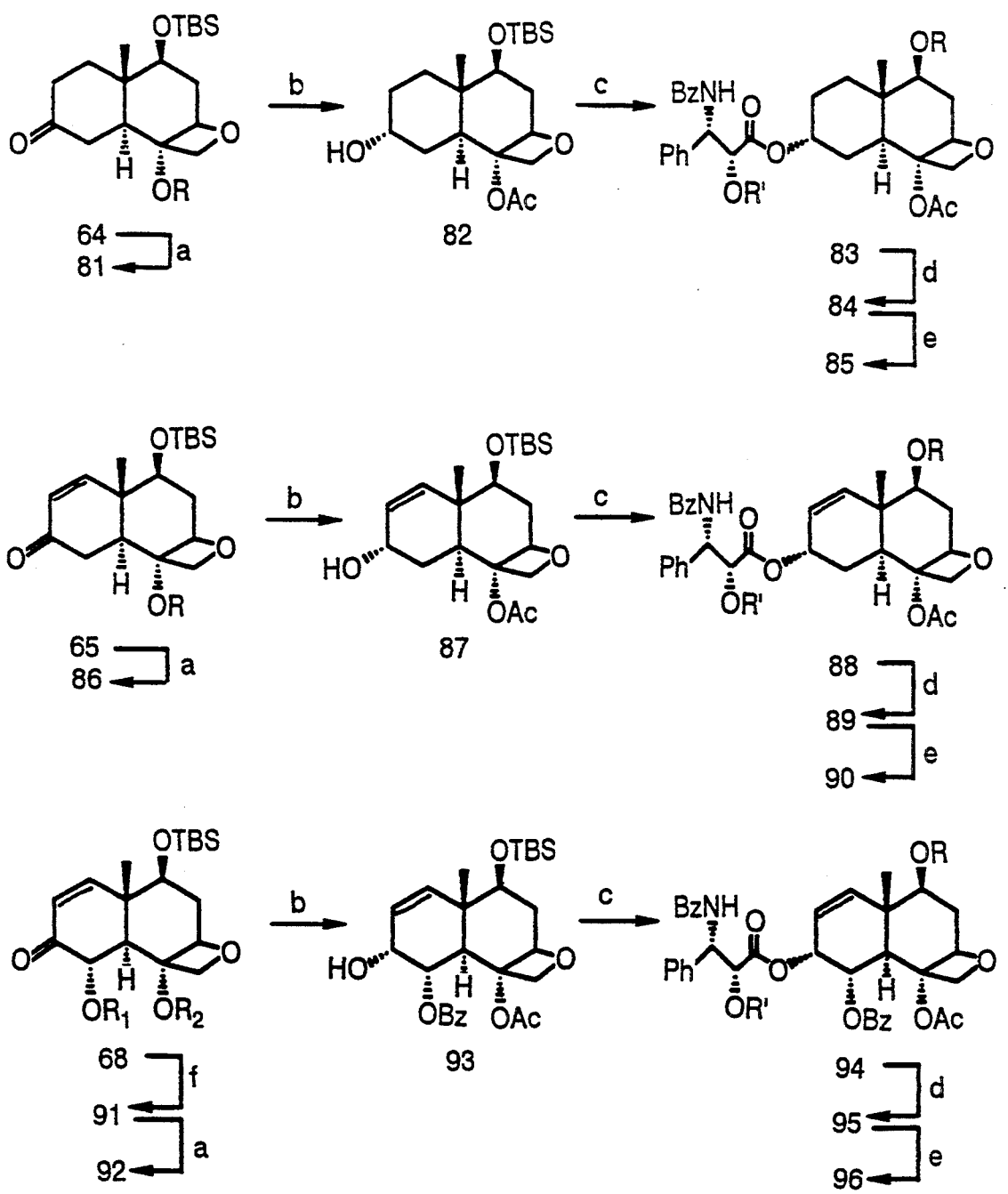
FIG. 17. Mimics of taxol. (a) Ac₂O/Pyr; (b) L-selectride/THF/78° C.; (c) See (49); (d) TBAF/THF; (e) dilute acid/H₂O; (f) BzCl/pyr.

In FIG. 17 are given syntheses of simple taxol mimics which contain two critical features of taxol itself, namely the side chain and the acetoxyoxetane.

Acetylation of 64 gives 81. Reduction of the ketone of 81 with a bulky hydride (L-selectride) produces alcohol 82. Coupling of the side-chain using the method of Denis et al. (49) yields mimic 85 after removal of the TBS and EE groups. The procedures are the same for the unsaturated series (65 to 90).

Diol 68 is benzoylated at the less hindered secondary alcohol to give 91, leaving the tertiary position open to subsequent acetylation, yielding 92. The same reduction/coupling/deprotection sequence described above is applied to 92 giving mimic 96.

References

1. Wani, M. C.; Taylor, H. L.; Wall, M. E.; Loggan, P.; McPhail, A. T. *J. Am. Chem. Soc.* 1971, 93, 2325.
2. Swindell, C. S. *Org. Prep. Procedures Int.* 1991, 23, 465–543.
3. Blechert, S.; Guenard, D. *The Alkaloids*, Academic Press, 1990, 39, 195–238.
4. Rowinsky, E. K.; Cazenave, L. A.; Donehower, R. C. *J. Natl. Cancer Inst.* 1990, 82, 1247.
5. Chabner, B. A. *Princ. Prac. Oncol.* 1991, 5, 1.
6. Deutsch, H. M.; Glinski, J. A.; Hernandez, M.; Haugwitz, R. D.; Narayanan, V. L.; Suffness, M.; Zalkow, L. H. *J. Med. Chem.*, 1989, 32, 788.
7. Yadav, J. S.; Ravishankar, R. *Tetrahedron Letters*, 1991, 32, 2629.
8. Still, W. C.; Kahn, M.; Mitra, A. *J. Org. Chem.* 1978, 43, 2923.
9. Ketoketal 1 was prepared following procedure given in ref. 16 from the corresponding diketone obtained by condensation of the enamine of 2-methyl-3-pentanone with acryloyl chloride. Hargreaves, J. R.; Hickmott, P. W.; Hopkins, B. J. *J. Chem. Soc.* 1968, 2599.
10. Kende, A. S.; Johnson, S.; Sanfilippo, P.; Hodges, J. C.; Jungheim, L. N. *J. Am. Chem. Soc.* 1986, 108, 3513.
11. Ettouati, L.; Ahond, A.; Poupat, C.; Potier, P. *Tetrahedron*, 1991, 47, 9823.
12. Magee, T. V., personal communication.
13. Takai, K.; Tagashira, M.; Kuroda, T; Oshima, K.; Utimoto, K.; Nozaki, H. *J. Am. Chem. Soc.* 1986, 108, 6048.
14. Jin, H.; Uenishi, J.-I.; Christ, W. J.; Kishi, Y. *J. Am. Chem. Soc.* 1986, 108, 5644.
15. Scott, W. J.; Stille, J. K. *J. Am. Chem. Soc.* 1986, 108, 3033.
16. Detering, J.; Martin, H.-D. *Angew. Chem. Int. Ed. Eng.* 1988, 27, 695.
17. Griffith, W. P.; Ley, S. V.; Whitcombe, G. P.; White, A. D. *J. Chem. Soc., Chem. Commun.* 1987, 1625.
18. Danishefsky, S.; Kitahara, T.; Yan, C. F.; Morris, J. *J. Am. Chem. Soc.* 1979, 101, 6996.
19. Nagata, W.; Yoshioka, M.; Hirai, S. *J. Am. Chem. Soc.* 1972, 93, 4635.
20. Omura, K.; Sharma, A. K.; Swern, D. *J. Org. Chem.* 1976, 41, 957.
21. Huang, S. L.; Omura, K.; Swern, D. *Synthesis* 1978, 297.
22. Davis, F. A.; Vishwakarma, L. C.; Billmers, J. M.; Finn, J. *J. Org. Chem.* 1984, 49, 3241.
23. Vishwakarma, L. C; Stringer, O. D.; Davis, F. A. *Org. Synth.* 1987, 66, 203.
24. Böhm, I.; Schulz, R.; Reissig, H.-U. *Tetrahedron Lett.* 1982, 23, 2013.
25. Larcheveque, M.; Perriot, P.; Petit, Y. *Synthesis* 1983, 297.
26. Salmond, W. G.; Barta, M. A.; Havens, J. L. *J. Org. Chem.* 1978, 43, 2057.
27. Wieland, P.; Miescher, K. *Helv. Chim. Acta* 1950, 33, 2215.
28. As presented here, the cycloaddition product would require an allylic oxidation step for the introduction of the oxygenation at C-13 ($X_1$), though it may be desirable to have it in the diene prior to cycloaddition.
29. An obvious precursor to this nucleophile has been synthesized in these laboratories by Dr. Richard C. A. Isaacs; specifically VIII (M=H; $X_2$=O,O).
30. Syntheses of XII ($X_1$=H,H; $X_5$=OCH$_2$CH$_2$O and O,O and XIII (M=H; $X_1$=H,H; $X_5$=OCH$_2$CH$_2$O) have been achieved in these laboratories by Dr. Yves Queneau.
31. Boyce, C. B. C.; Whitehurst, J. S. *J. Chem. Soc.* 1960, 2680.
32. Ward, D.; Rhee,·C. K.; Zoghaib, W. M. *Tetrahedron Lett.* 1988, 29, 517.
33. Heathcock, C. H.; Ratcliffe, R. *J. Am. Chem. Soc.* 1971, 93, 1746.
34. Gutzwiller, J.; Buchschacher, P.; First, A. *Synthesis* 1977, 167.
35. Hajos, Z. G.; Parrish, D. R. *Org. Synth.* 1985, 63, 26.
36. Jung, M. E.; Hatfield, G. L. *Tetrahedron Lett.* 1983, 24, 3175.
37. Toda, F.; Tanaka, K. *Tetrahedron Lett.* 1988, 29, 551.
38. Corey, E. J.; Cho, H.; Ricker, C.; Hua, D. H. *Tetrahedron Lett.* 1981, 22, 3455.
39. Griffith, W. P.; Ley, S. V.; Whitcombe, G. P.; White, A. D. *J. Chem. Soc., Chem. Commun.* 1987, 1625.
40. Aldrichimica Acta 1989, 22, 53.
41. Scott, W. J.; McMurry, J.E. *Acc. Chem. Res.* 1988, 21, 47.
42. Corey, E. J.; Houpis, I. N. *J. Am. Chem. Soc.* 1990, 112, 8997.
43. Tius, M. A.; Kannangara, G. S. K. *J. Org. Chem.* 1990, 55, 5711.
44. Cacchi, S.; Morera, E.; Ortar, G. *Tetrahedron Lett.* 1985, 26, 1109.
45. Ettouati, L.; Ahond, A.; Poupat, C.; Potier, P. *Tetrahedron* 1991, 47, 9823.
46. The free tertiary hydroxyl served, as the lithium alcoholate, to direct the lithium enolate formation to the regiochemically desired position. (When the alcohol was silylated, a significant amount of the undesired enone was formed). The lithio-dianion was subsequently trapped with excess TMSCl to give the disilyl enol ether. During the course of subsequent oxidation, the majority of the tertiary silyl ether was concomitantly removed. After consumption of starting material (TLC), MeOH and $K_2CO_3$ were added to complete the desilyation process to give 65.
47. Ito, Y.; Hirao, T.; Saegusa, T. *J. Org. Chem.* 1987, 43, 1011.
48. Shirai, R.; Tanaka, M.; Koga, K. *J. Am. Chem. Soc.* 1986, 108, 543.
49. Denis, J.-N. et al *J. Am. Chem. Soc.* 1988, 110, 5917.

What is claimed is:

1. A compound having the structure:

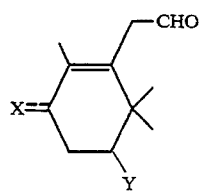

wherein X is H, OH, O or OSiR$_3$; Y is —OCH$_2$CH$_2$O—; and R is an alkyl or aryl group.

2. A compound having the structure:

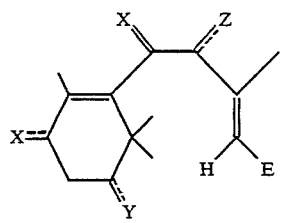

wherein each X is independently the same or different and is H, OH, O or OSiR$_3$; Y is —OCH$_2$CH$_2$O—; Z is OH, O or OTMS; E is H, CN, CO$_2$R, CHO or CH$_2$OR'; R' is H, COR, R or SiR$_3$; and R is an alkyl or aryl group.

3. A compound having the structure:

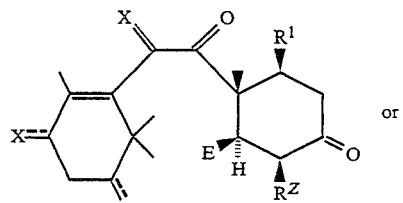

or

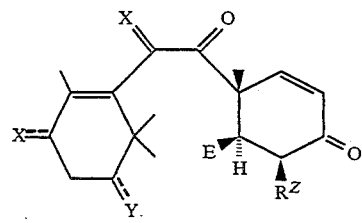

wherein each X is independently the same or different and is H, OH, O or OSiR$_3$; Y is —OCH$_2$CH$_2$O—; and E is H, CN, CO$_2$R, CHO or CH$_2$OR'; R$^1$ is H, OH, OCOR, OR or OSiR$_3$; R$^2$ is H, CH$_2$OSiR$_3$, CH$_2$SR or CH$_2$SOR; R' is H, COR, R or SiR$_3$; and R is an alkyl or aryl group.

* * * * *